(12) United States Patent  (10) Patent No.: US 8,444,692 B2
Michelson  (45) Date of Patent: *May 21, 2013

(54) INSTRUMENTATION WITH INWARDLY MOVEABLE EXTENSIONS FOR INSERTING AN EXPANDABLE INTERBODY SPINAL FUSION IMPLANT

(75) Inventor: Gary K. Michelson, Venice, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 2992 days.

This patent is subject to a terminal disclaimer.

(21) Appl. No.: 10/911,919

(22) Filed: Aug. 4, 2004

(65) Prior Publication Data

US 2005/0015149 A1    Jan. 20, 2005

Related U.S. Application Data

(62) Division of application No. 10/061,236, filed on Feb. 4, 2002, now Pat. No. 7,118,579.

(60) Provisional application No. 60/266,426, filed on Feb. 4, 2001, provisional application No. 60/277,890, filed on Mar. 21, 2001.

(51) Int. Cl.
*A61F 2/44* (2006.01)
*A61B 17/58* (2006.01)

(52) U.S. Cl.
USPC .......................... 623/17.11; 606/99

(58) Field of Classification Search
USPC .................... 623/17.11–17.16; 606/99, 86 A
See application file for complete search history.

(56) References Cited

U.S. PATENT DOCUMENTS

| | | | |
|---|---|---|---|
| 3,875,595 | A | 4/1975 | Froning |
| 4,309,777 | A | 1/1982 | Patil |
| 4,349,921 | A | 9/1982 | Kuntz |
| 4,401,112 | A | 8/1983 | Rezaian |
| 4,501,269 | A | 2/1985 | Bagby |
| 4,553,273 | A | 11/1985 | Wu |
| 4,554,914 | A | 11/1985 | Kapp et al. |
| 4,636,217 | A | 1/1987 | Ogilvie et al. |
| 4,657,550 | A | 4/1987 | Daher |
| 4,714,469 | A | 12/1987 | Kenna |
| 4,759,769 | A | 7/1988 | Hedman et al. |
| 4,863,476 | A | 9/1989 | Shepperd |
| 4,877,020 | A | 10/1989 | Vich |
| 4,932,975 | A | 6/1990 | Main et al. |
| 4,961,740 | A | 10/1990 | Ray et al. |
| 5,015,247 | A | 5/1991 | Michelson |
| 5,026,373 | A | 6/1991 | Ray et al. |
| 5,055,104 | A | 10/1991 | Ray |

(Continued)

FOREIGN PATENT DOCUMENTS

| | | |
|---|---|---|
| CA | 2 151 481 | 3/1995 |
| DE | 39 22 203 | 7/1989 |

(Continued)

OTHER PUBLICATIONS

U.S. Appl. No. 60/272,381, filed Mar. 2001, Michelson.

(Continued)

*Primary Examiner* — Ellen C Hammond
(74) *Attorney, Agent, or Firm* — Martin & Ferraro, LLP

(57) ABSTRACT

An implant holder for inserting an interbody spinal implant.

49 Claims, 34 Drawing Sheets

U.S. PATENT DOCUMENTS

| | | | |
|---|---|---|---|
| 5,059,193 A | 10/1991 | Kuslich |
| 5,062,850 A | 11/1991 | MacMillan et al. |
| 5,120,322 A | 6/1992 | Davis et al. |
| 5,123,926 A | 6/1992 | Pisharodi |
| 5,147,402 A | 9/1992 | Bohler et al. |
| 5,171,278 A | 12/1992 | Pisharodi |
| 5,192,327 A | 3/1993 | Brantigan |
| 5,236,460 A | 8/1993 | Barber |
| 5,258,031 A | 11/1993 | Salib et al. |
| 5,263,953 A | 11/1993 | Bagby |
| 5,290,312 A | 3/1994 | Kojimoto et al. |
| 5,306,310 A | 4/1994 | Siebels |
| 5,314,477 A | 5/1994 | Marnay |
| 5,336,223 A | 8/1994 | Rogers |
| 5,390,683 A | 2/1995 | Pisharodi |
| 5,397,364 A | 3/1995 | Kozak et al. |
| 5,439,684 A | 8/1995 | Prewett et al. |
| 5,455,231 A | 10/1995 | Constantz et al. |
| 5,464,439 A | 11/1995 | Gendler |
| 5,484,437 A | 1/1996 | Michelson |
| 5,507,813 A | 4/1996 | Dowd et al. |
| 5,507,816 A | 4/1996 | Bullivant |
| 5,522,899 A | 6/1996 | Michelson |
| 5,540,697 A | 7/1996 | Rehmann et al. |
| 5,549,679 A | 8/1996 | Kuslich |
| 5,554,191 A | 9/1996 | Lahille et al. |
| 5,593,409 A | 1/1997 | Michelson |
| 5,605,938 A | 2/1997 | Roufa et al. |
| 5,609,635 A * | 3/1997 | Michelson ................. 623/17.16 |
| 5,630,843 A | 5/1997 | Rosenberg |
| 5,649,931 A | 7/1997 | Bryant et al. |
| 5,653,763 A | 8/1997 | Errico et al. |
| 5,665,122 A | 9/1997 | Kambin |
| 5,669,909 A | 9/1997 | Zdeblick et al. |
| 5,683,399 A | 11/1997 | Jones |
| 5,693,100 A | 12/1997 | Pisharodi |
| 5,702,391 A | 12/1997 | Lin |
| 5,702,446 A | 12/1997 | Schenek et al. |
| 5,702,455 A | 12/1997 | Saggar |
| 5,713,904 A | 2/1998 | Errico et al. |
| 5,716,415 A | 2/1998 | Steffee |
| 5,749,916 A | 5/1998 | Richelsoph |
| 5,766,253 A | 6/1998 | Brosnahan, III |
| 5,776,199 A | 7/1998 | Michelson |
| 5,782,830 A | 7/1998 | Farris |
| 5,782,832 A | 7/1998 | Larsen et al. |
| 5,785,710 A | 7/1998 | Michelson |
| 5,797,909 A | 8/1998 | Michelson |
| 5,800,550 A | 9/1998 | Sertich |
| 5,827,328 A | 10/1998 | Buttermann |
| 5,860,973 A | 1/1999 | Michelson |
| 5,865,848 A | 2/1999 | Baker |
| 5,866,113 A | 2/1999 | Hendriks et al. |
| 5,885,299 A | 3/1999 | Winslow et al. |
| 5,885,982 A | 3/1999 | Dolynchuk et al. |
| 5,888,224 A | 3/1999 | Beckers et al. |
| 5,910,141 A | 6/1999 | Morrison et al. |
| 5,928,242 A | 7/1999 | Kuslich et al. |
| 5,928,284 A | 7/1999 | Mehdizadeh |
| 5,968,098 A | 10/1999 | Winslow |
| 5,976,187 A | 11/1999 | Richelsoph |
| 5,980,522 A | 11/1999 | Koros et al. |
| 5,989,290 A | 11/1999 | Biedermann et al. |
| 5,997,474 A | 12/1999 | Batchelor |
| 6,015,436 A | 1/2000 | Schonhoffer |
| 6,019,792 A | 2/2000 | Cauthen |
| 6,039,761 A | 3/2000 | Li et al. |
| 6,045,579 A | 4/2000 | Hochshuler et al. |
| 6,059,829 A | 5/2000 | Schlapfer et al. |
| 6,066,174 A * | 5/2000 | Farris ................... 606/206 |
| 6,080,155 A | 6/2000 | Michelson |
| 6,080,193 A | 6/2000 | Hochshuler et al. |
| 6,083,225 A | 7/2000 | Winslow et al. |
| 6,083,228 A | 7/2000 | Michelson |
| 6,087,555 A | 7/2000 | Dunstan et al. |
| 6,093,207 A | 7/2000 | Pisharodi |
| 6,102,934 A | 8/2000 | Li |
| 6,102,950 A | 8/2000 | Vaccaro |
| 6,106,558 A | 8/2000 | Picha |
| 6,117,174 A | 9/2000 | Nolan |
| 6,126,689 A | 10/2000 | Brett |
| 6,129,763 A | 10/2000 | Chauvin et al. |
| 6,143,031 A | 11/2000 | Knothe et al. |
| 6,159,214 A | 12/2000 | Michelson |
| 6,159,244 A | 12/2000 | Suddaby |
| 6,174,311 B1 | 1/2001 | Branch et al. |
| 6,174,334 B1 | 1/2001 | Suddaby |
| 6,176,882 B1 | 1/2001 | Biedermann et al. |
| 6,179,873 B1 * | 1/2001 | Zientek ................. 623/17.11 |
| 6,183,517 B1 | 2/2001 | Suddaby |
| 6,190,414 B1 | 2/2001 | Young et al. |
| 6,190,880 B1 | 2/2001 | Israel et al. |
| 6,193,757 B1 | 2/2001 | Foley et al. |
| 6,201,039 B1 | 3/2001 | Brown et al. |
| 6,210,412 B1 | 4/2001 | Michelson |
| 6,217,579 B1 | 4/2001 | Koros |
| 6,224,607 B1 | 5/2001 | Michelson |
| 6,319,257 B1 | 11/2001 | Carignan et al. |
| 6,332,895 B1 | 12/2001 | Suddaby |
| 6,371,988 B1 | 4/2002 | Pafford et al. |
| 6,375,683 B1 | 4/2002 | Crozet et al. |
| 6,409,766 B1 | 6/2002 | Brett |
| 6,417,173 B1 * | 7/2002 | Roufa et al. ................. 514/54 |
| 6,419,705 B1 | 7/2002 | Erickson |
| 6,436,140 B1 * | 8/2002 | Liu et al. ................. 623/17.11 |
| 6,443,989 B1 | 9/2002 | Jackson |
| 6,454,806 B1 | 9/2002 | Cohen et al. |
| 6,485,517 B1 | 11/2002 | Michelson |
| 6,491,724 B1 | 12/2002 | Ferree |
| 6,500,205 B1 | 12/2002 | Michelson |
| 6,562,074 B2 | 5/2003 | Gerbec et al. |
| 6,582,431 B1 | 6/2003 | Ray |
| 6,652,584 B2 | 11/2003 | Michelson |
| 6,692,501 B2 | 2/2004 | Michelson |
| 6,706,070 B1 | 3/2004 | Wagner et al. |
| 6,709,458 B2 | 3/2004 | Michelson |
| 6,716,247 B2 | 4/2004 | Michelson |
| 6,743,255 B2 | 6/2004 | Ferree |
| 6,793,679 B2 | 9/2004 | Michelson |
| 6,808,537 B2 | 10/2004 | Michelson |
| 6,814,756 B1 | 11/2004 | Michelson |
| 6,821,298 B1 | 11/2004 | Jackson |
| 6,835,206 B2 | 12/2004 | Jackson |
| 6,905,512 B2 | 6/2005 | Paes et al. |
| 6,923,810 B1 | 8/2005 | Michelson |
| 6,962,606 B2 | 11/2005 | Michelson |
| 6,972,035 B2 | 12/2005 | Michelson |
| 7,008,453 B1 | 3/2006 | Michelson |
| 7,118,579 B2 | 10/2006 | Michelson |
| 7,118,598 B2 | 10/2006 | Michelson |
| 7,147,665 B1 | 12/2006 | Bryan et al. |
| 7,608,107 B2 | 10/2009 | Michelson |
| 7,655,027 B2 | 2/2010 | Michelson |
| 7,892,286 B2 | 2/2011 | Michelson |
| 7,922,729 B2 | 4/2011 | Michelson |
| 8,007,534 B2 | 8/2011 | Michelson |
| 8,075,621 B2 | 12/2011 | Michelson |
| 8,097,034 B2 | 1/2012 | Michelson |
| 2002/0068977 A1 | 6/2002 | Jackson |
| 2007/0032871 A1 | 2/2007 | Michelson |
| 2011/0137420 A1 | 6/2011 | Michelson |

FOREIGN PATENT DOCUMENTS

| | | |
|---|---|---|
| DE | 44 16 605 C1 | 6/1995 |
| EP | 0 836 457 | 9/2004 |
| FR | 2 717 068 | 9/1995 |
| FR | 2 771 282 | 5/1999 |
| FR | 2 782 632 | 3/2000 |
| SU | 1225561 A | 4/1986 |
| SU | 1424826 A1 | 9/1988 |
| WO | WO 96/27348 | 9/1996 |
| WO | WO 97/00054 | 12/1997 |
| WO | WO 98/34552 | 8/1998 |
| WO | WO 98/34568 | 8/1998 |
| WO | WO 98/48739 | 11/1998 |
| WO | WO 99/02108 | 1/1999 |
| WO | WO 99/26562 | 6/1999 |

| | | | | | | |
|---|---|---|---|---|---|---|
| WO | WO 99/42062 | 8/1999 | | WO | WO 00/78253 | 12/2000 |
| WO | WO 99/63891 | 12/1999 | | WO | WO 01/56513 | 8/2001 |
| WO | WO 00/12033 | 3/2000 | | | | |
| WO | WO 00/35388 | 6/2000 | | | | |
| WO | WO 00/35389 | 6/2000 | | | | |
| WO | WO 00/66045 | 11/2000 | | | | |
| WO | WO 00/74605 | 12/2000 | | | | |

OTHER PUBLICATIONS

U.S. Appl. No. 60/274,869, filed Mar. 2001, Michelson.

* cited by examiner

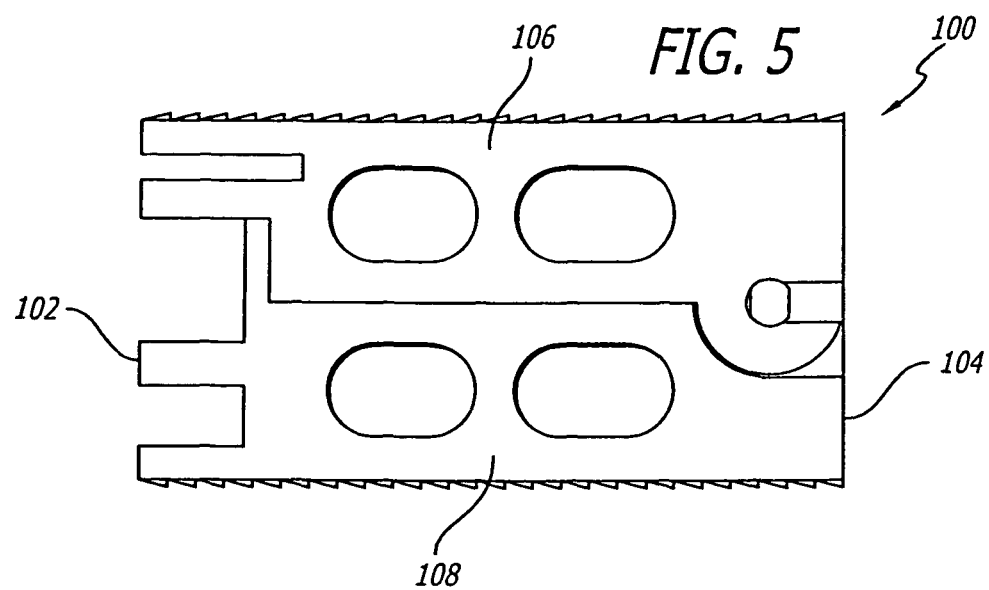
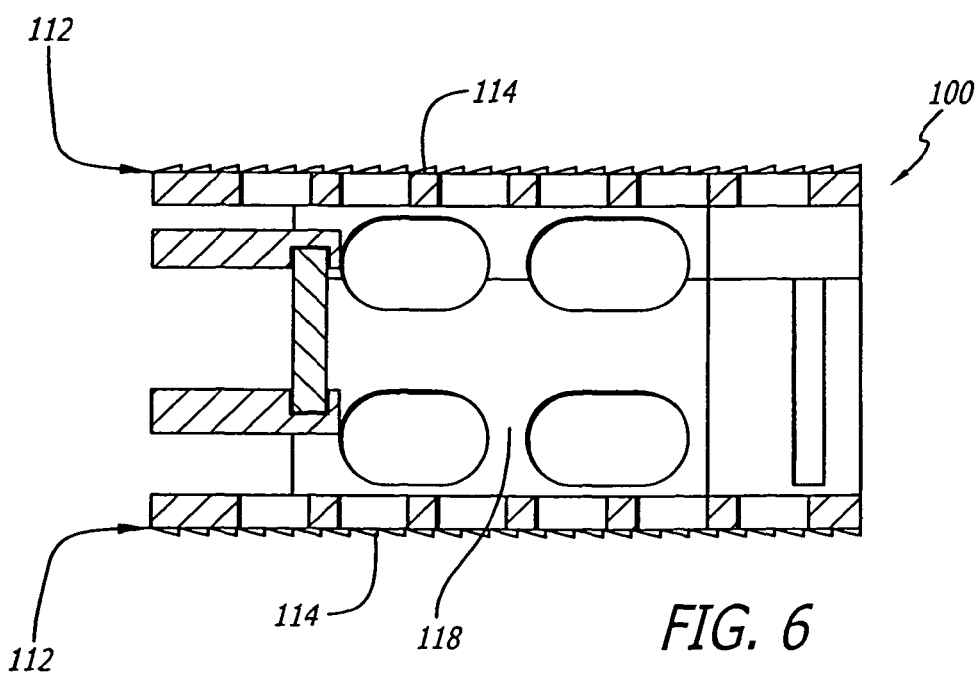

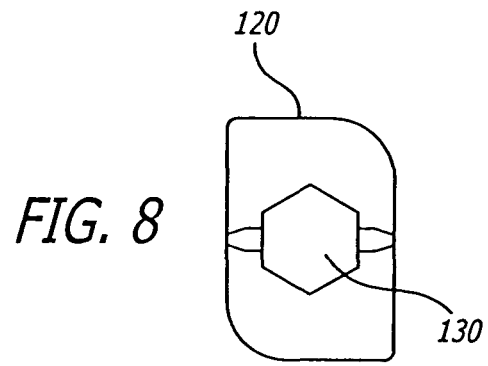
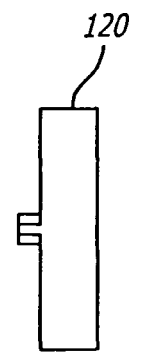
FIG. 8    FIG. 9
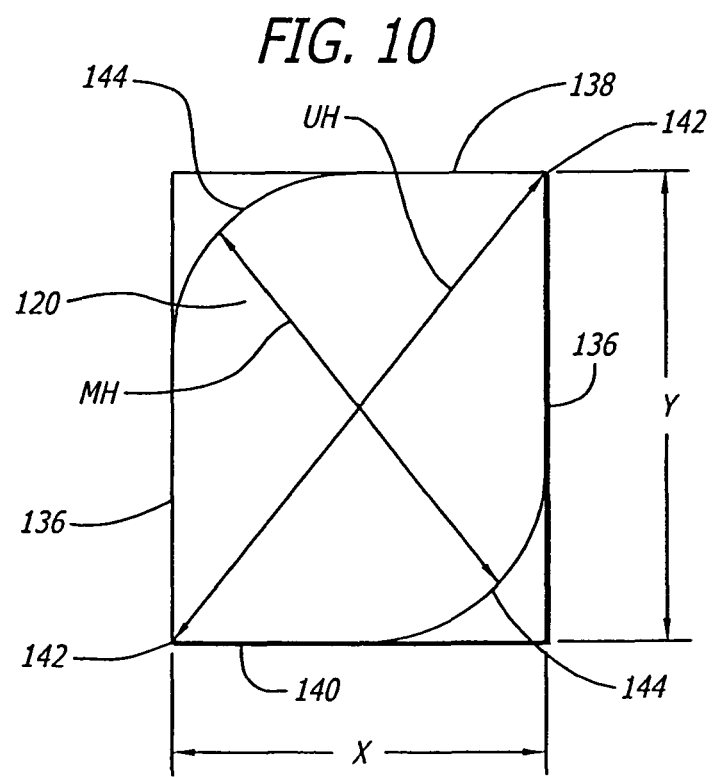
FIG. 10

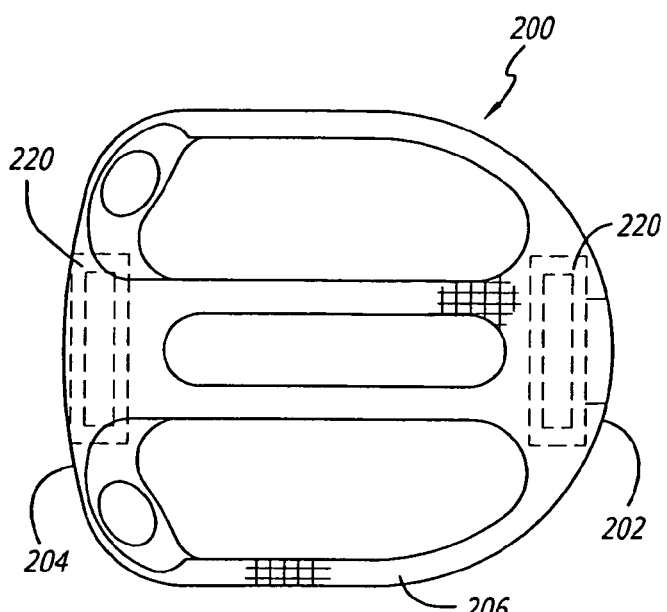
FIG. 11
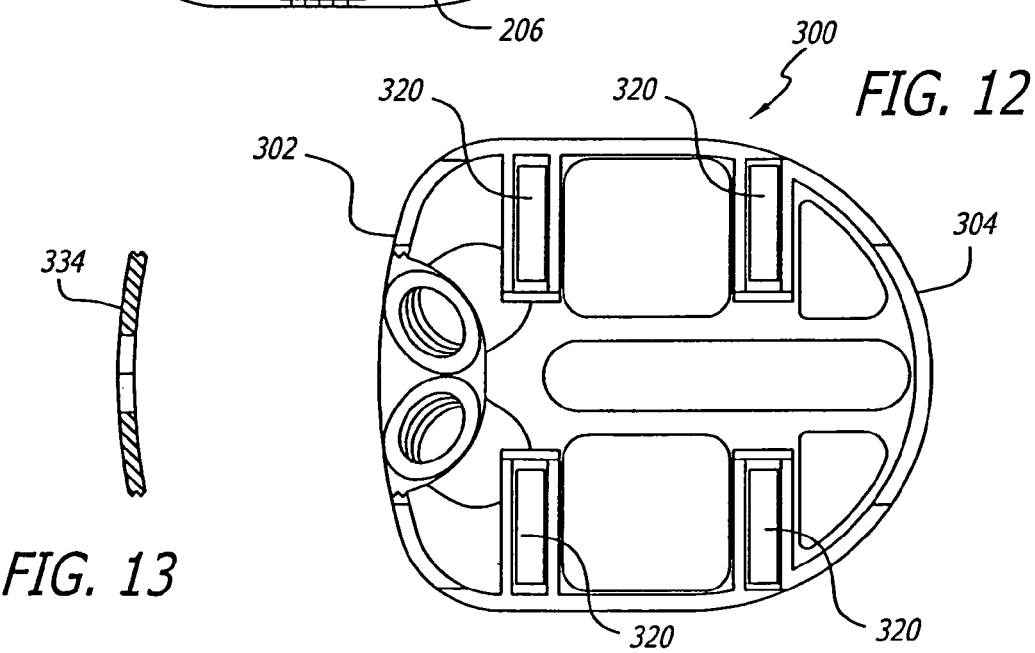
FIG. 13
FIG. 12
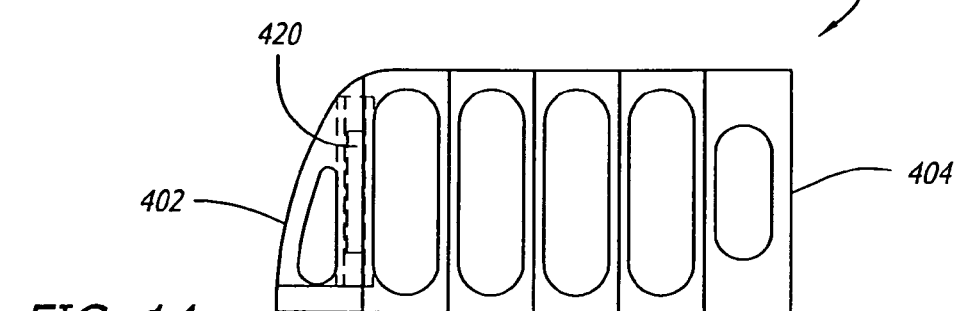
FIG. 14

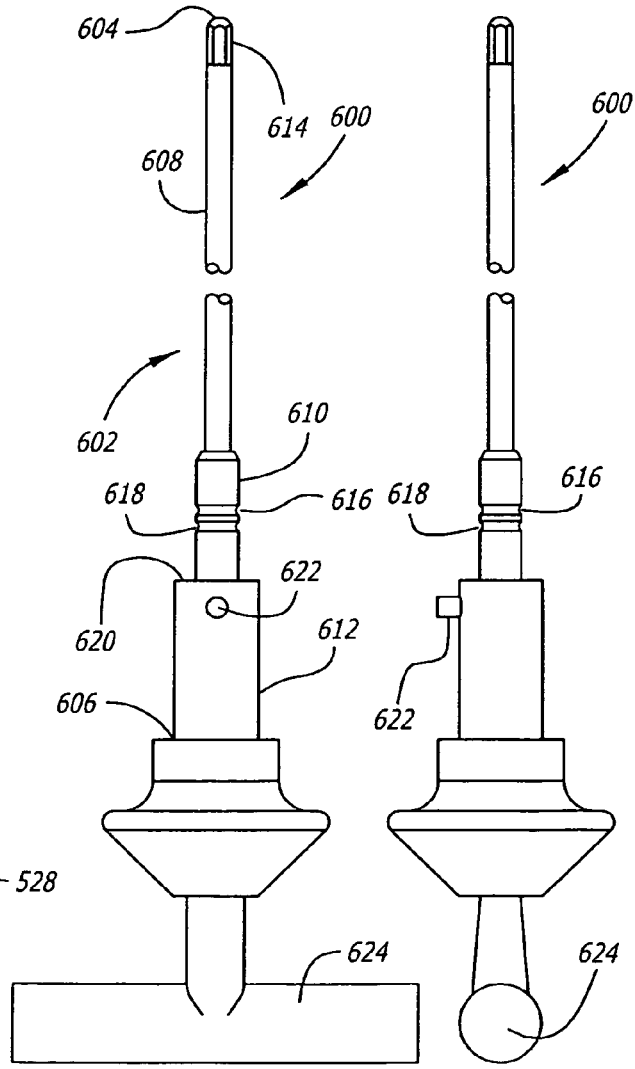

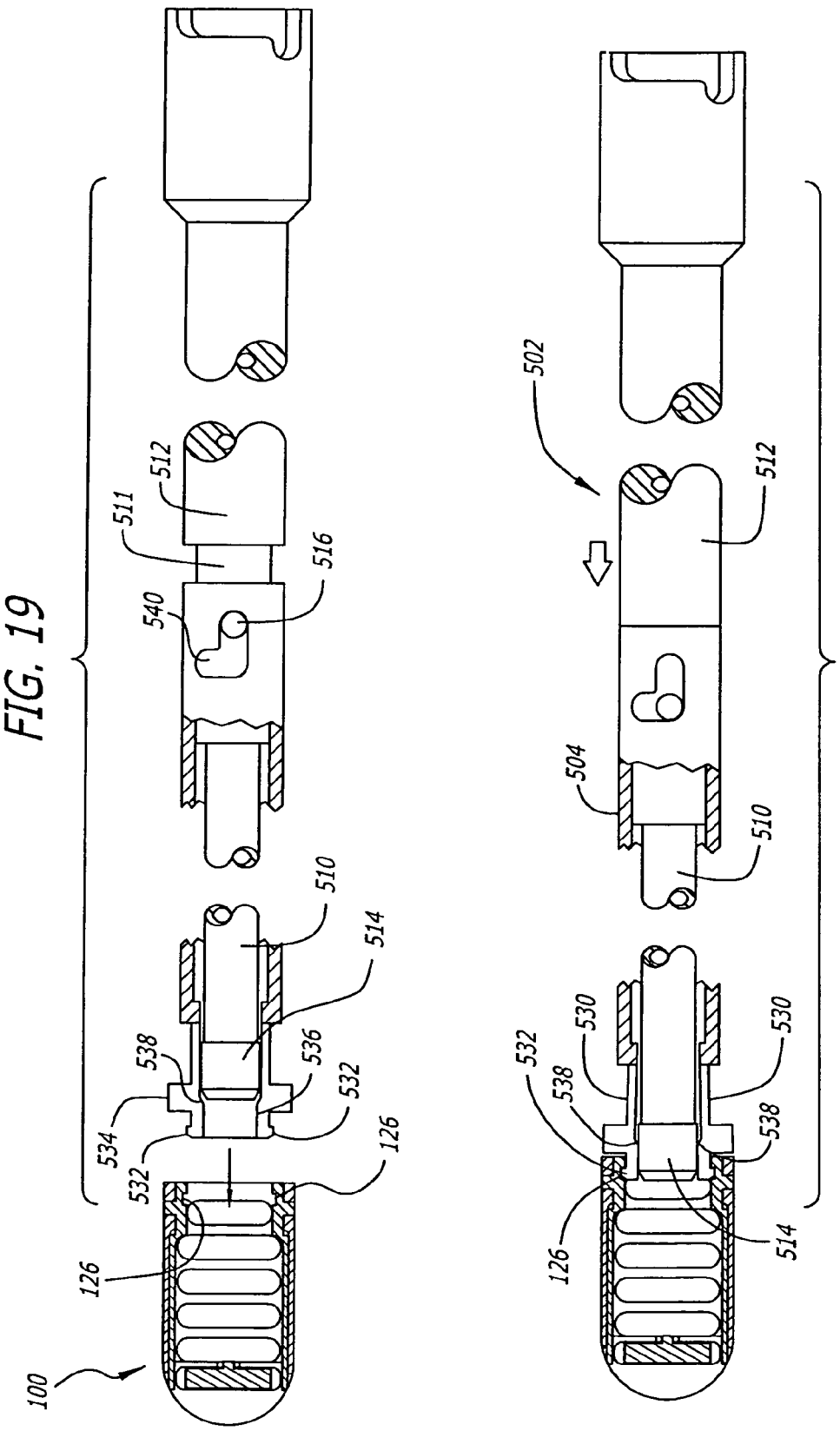

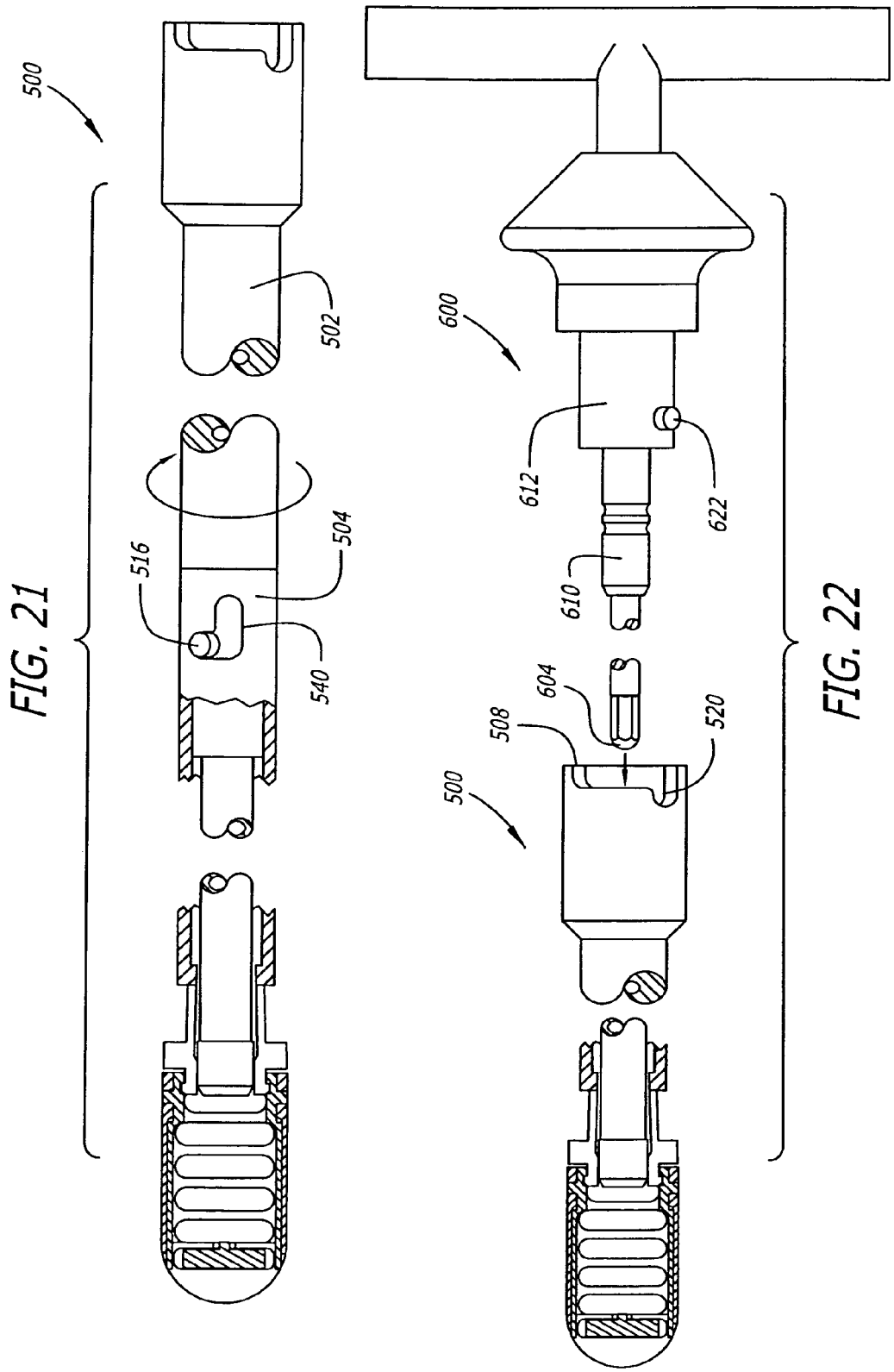

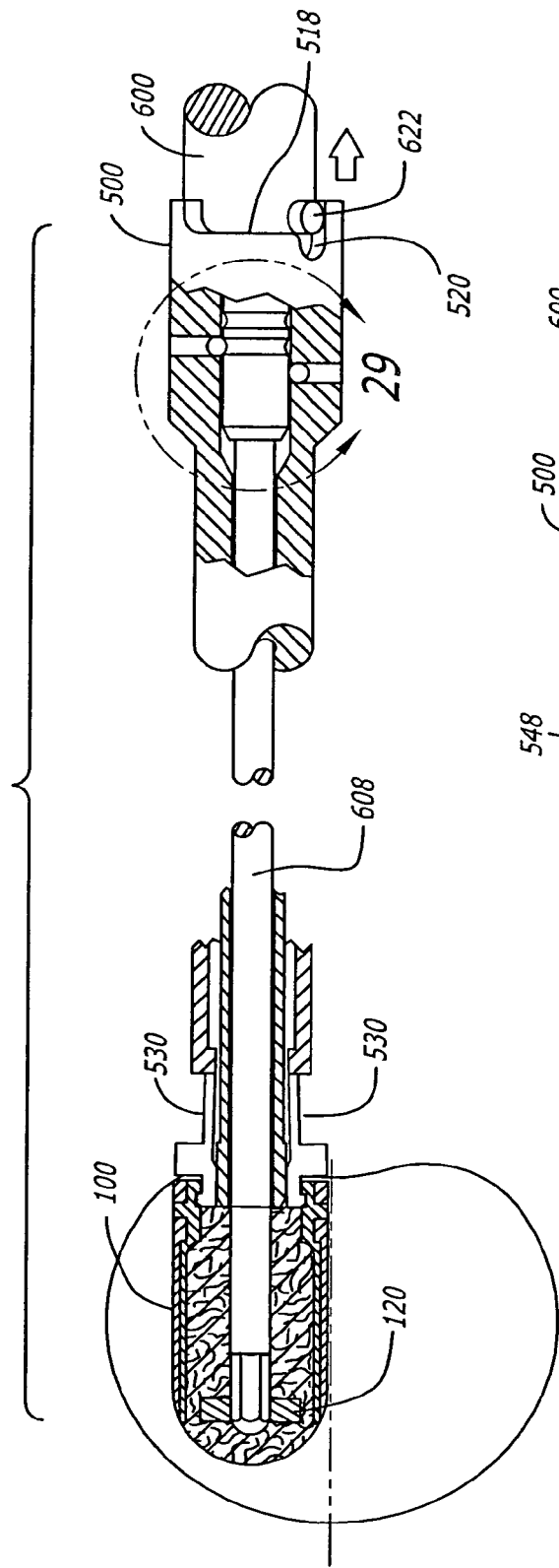
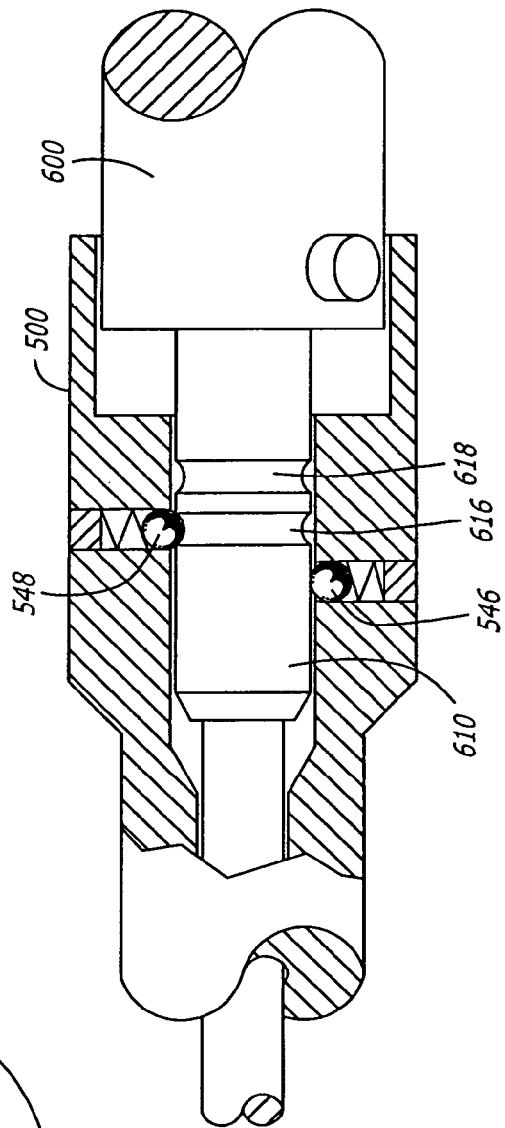
FIG. 28
FIG. 29

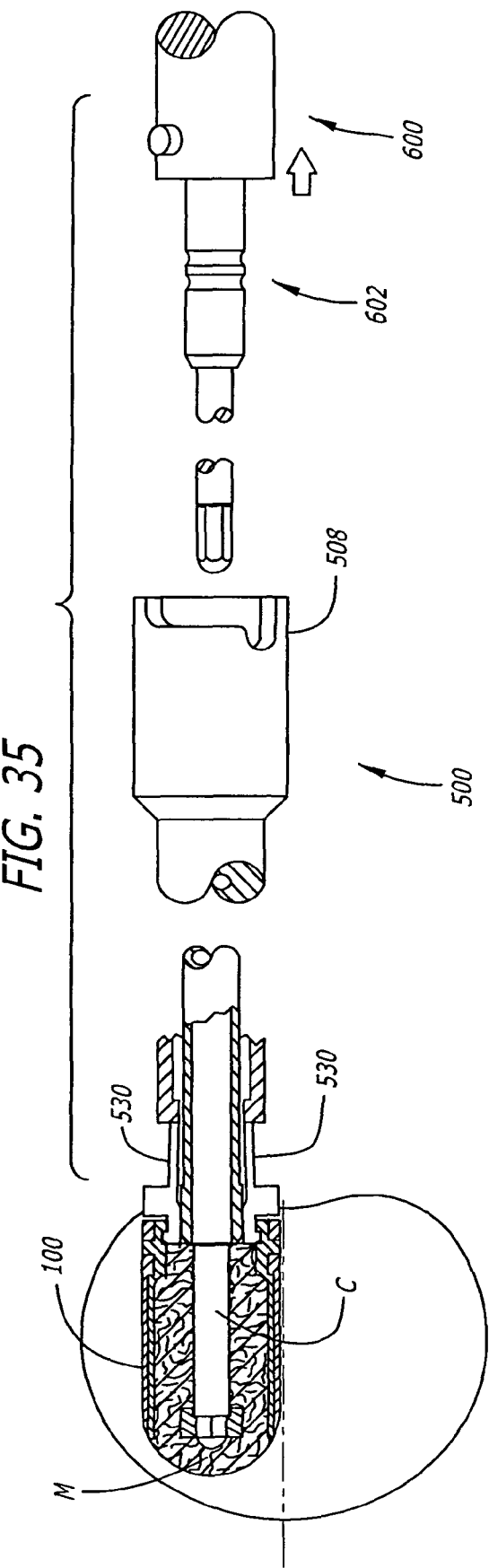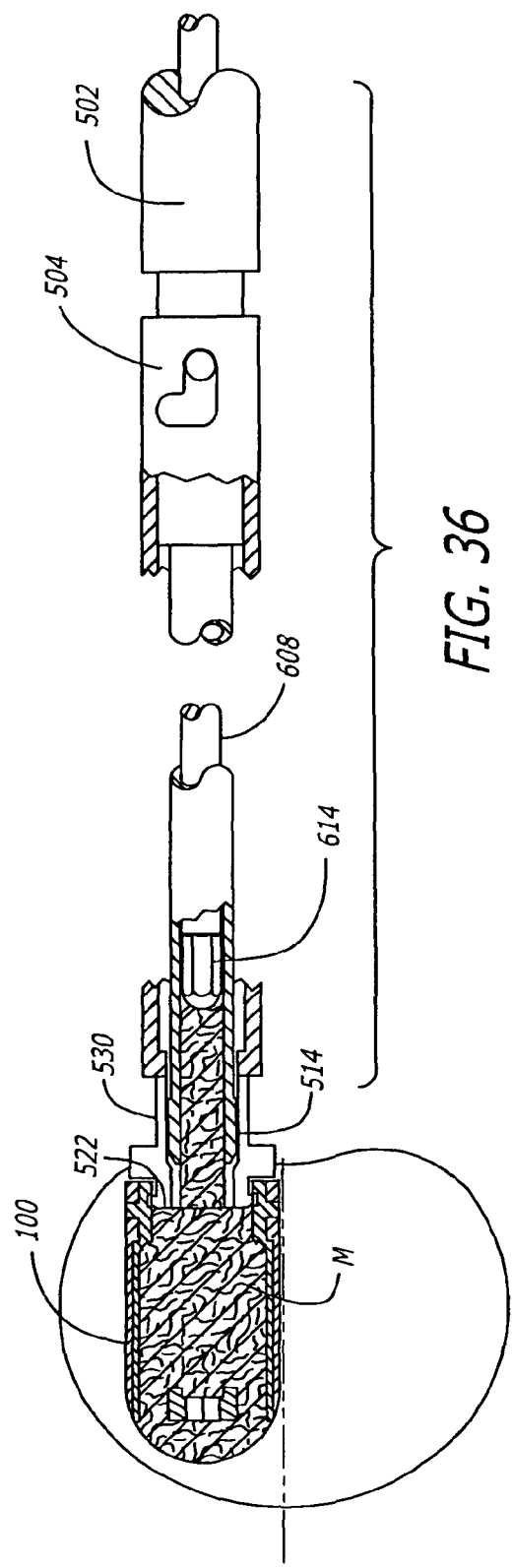

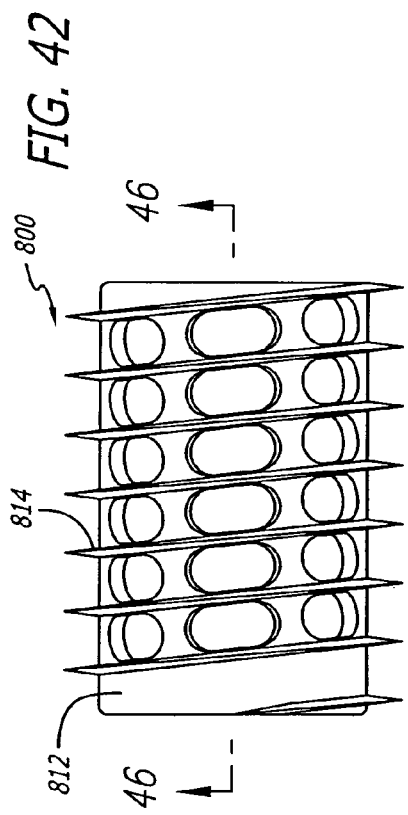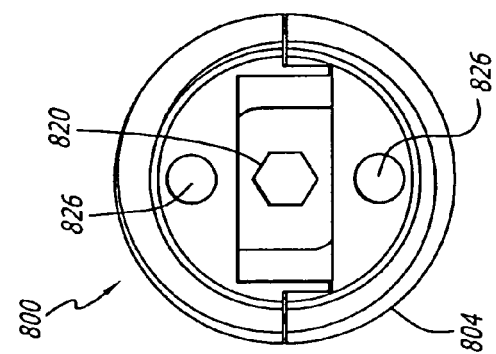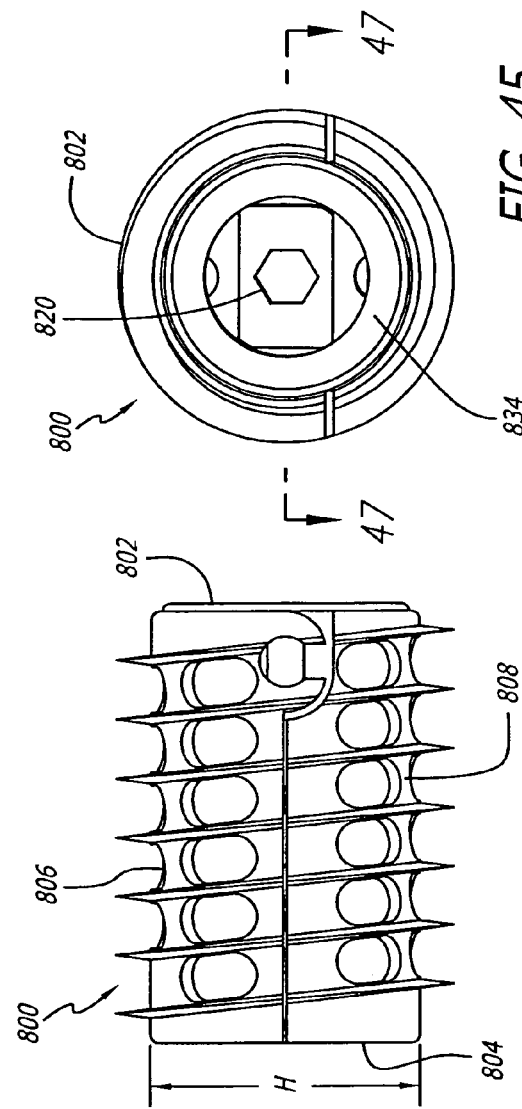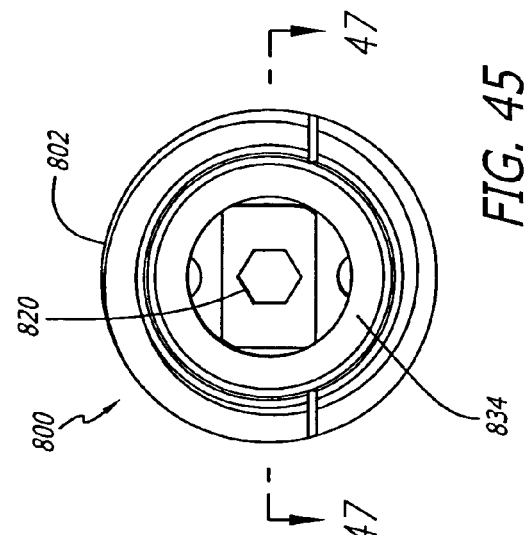

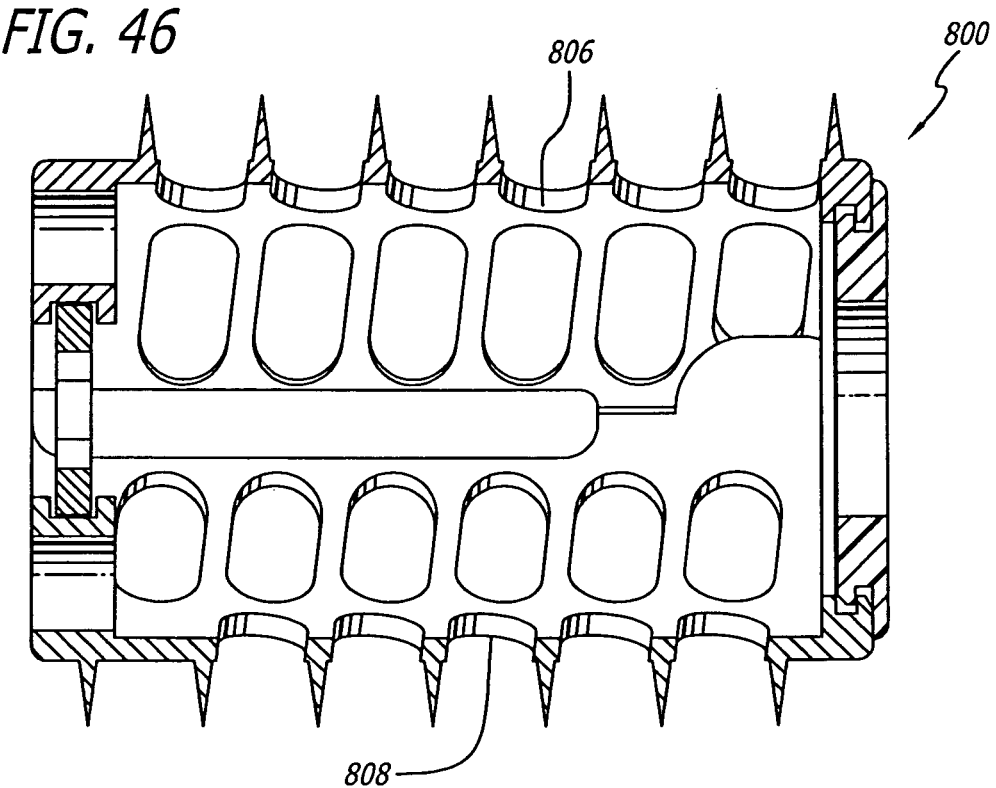

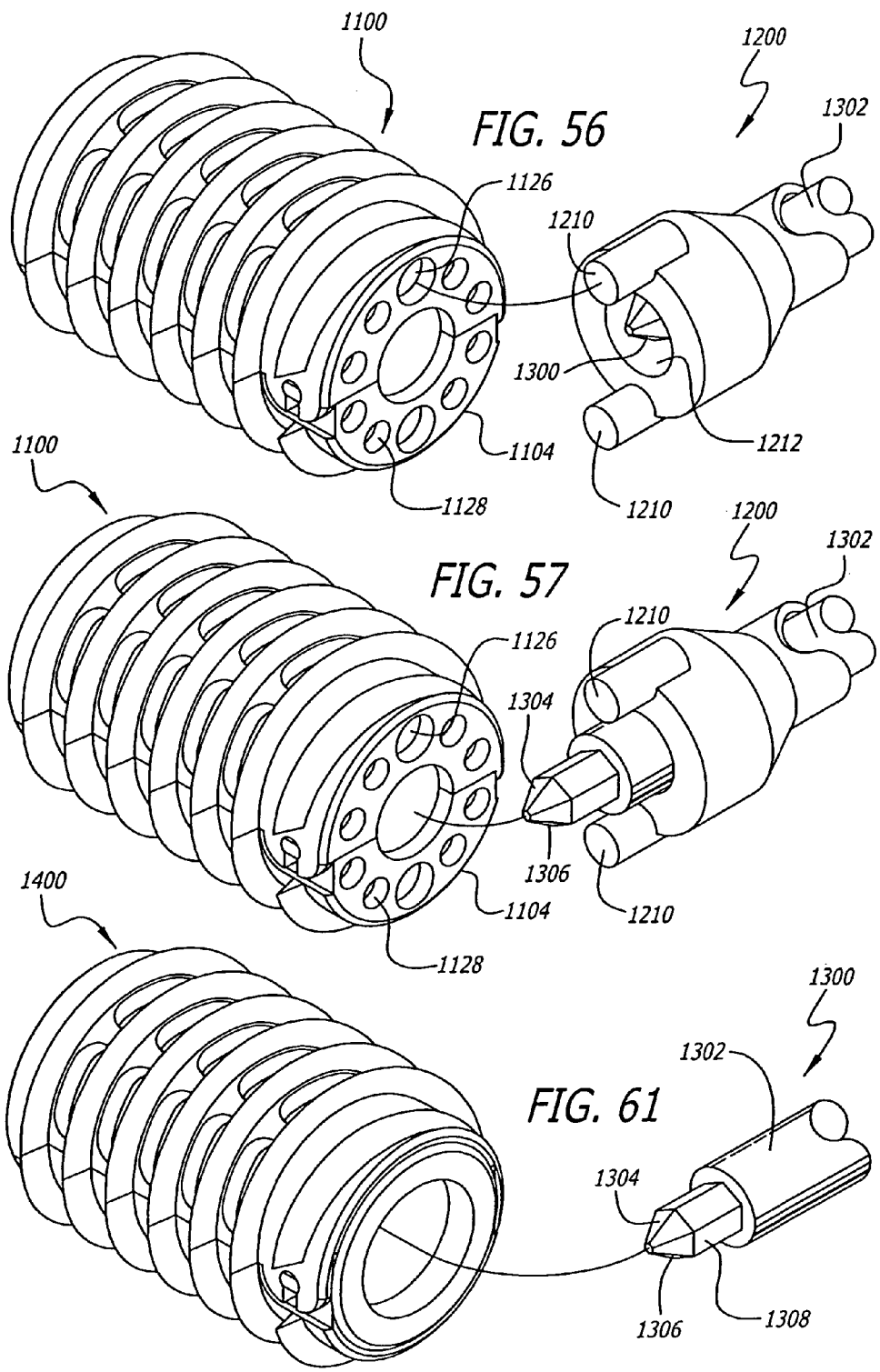

FIG. 64
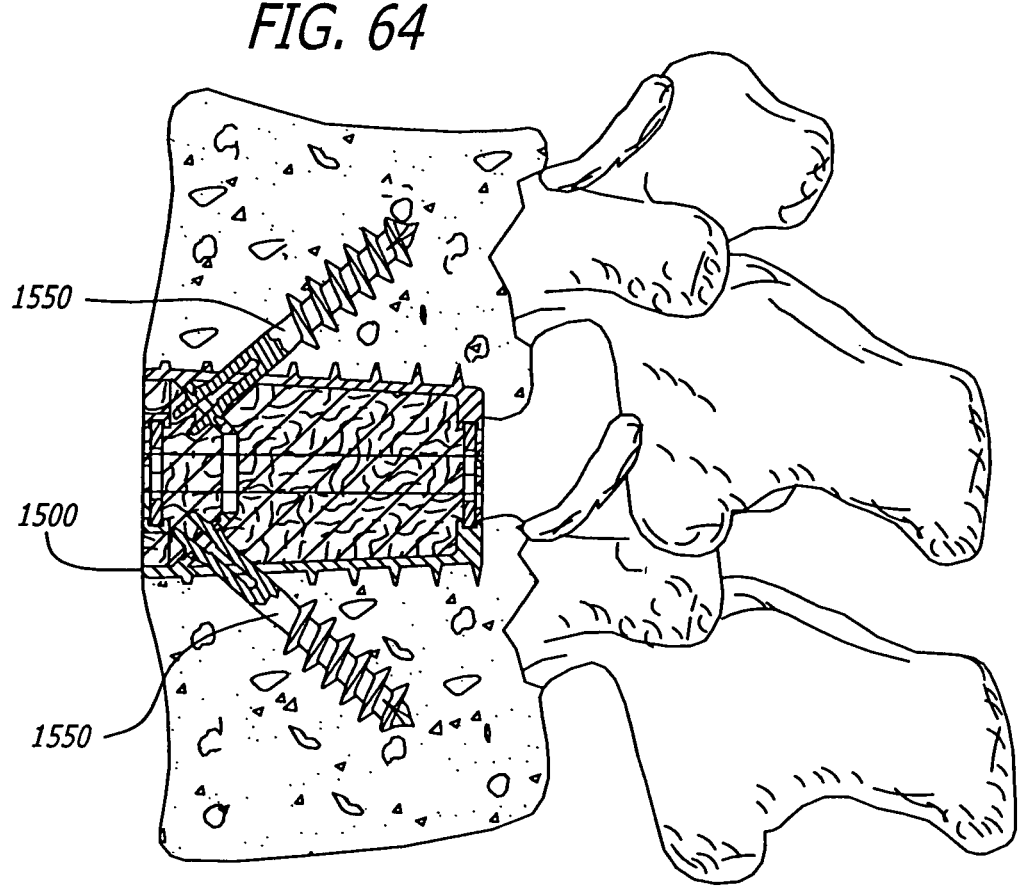
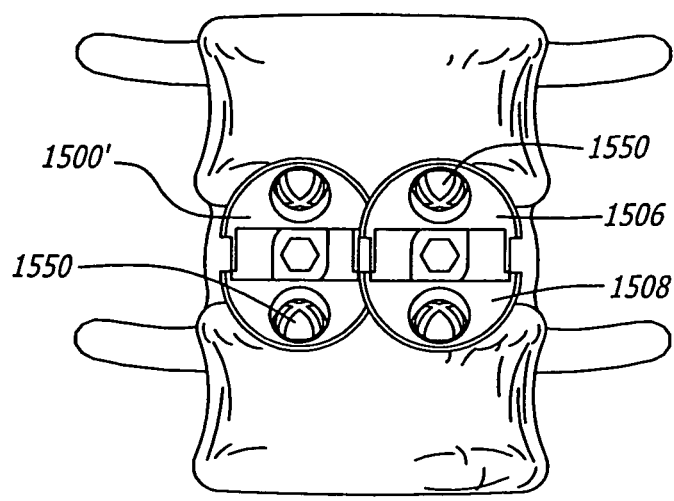
FIG. 65

INSTRUMENTATION WITH INWARDLY MOVEABLE EXTENSIONS FOR INSERTING AN EXPANDABLE INTERBODY SPINAL FUSION IMPLANT

RELATED APPLICATIONS

This application is a divisional of application Ser. No. 10/061,236, filed Feb. 4, 2002 now U.S. Pat. No. 7,118,579; which claims the benefit of provisional Application No. 60/266,426, filed Feb. 4, 2001, and provisional Application No. 60/277,890, filed Mar. 21, 2001; all of which are incorporated by reference herein.

BACKGROUND OF THE INVENTION

1. Field of the Invention

The present invention relates generally to instruments and methods for inserting interbody spinal implants into an implantation space in the spine, and more particularly for use with expandable interbody (for placement at least in part between adjacent vertebral bodies in the space previously occupied by disc material) spinal fusion implants for the immobilization of vertebrae.

2. Description of the Related Art

Expandable spinal fusion implants have height raising capabilities that are utilized once the implant is initially positioned. Such height raising capability may be utilized within the spine anteriorly, posteriorly, or both and to various extents, respectively so as to raise the front, back, or both of the implant by the same or various amounts. More particularly, such implants have upper and lower surfaces of upper and lower members that in a first or insertion position are collapsed relative to one another and in a second or deployed position are adapted to contact the adjacent vertebral bodies.

Expandable fusion implants offer the advantage of allowing for the placement of a potentially larger implant through a smaller opening in a patient's body. Selective expansion along a single direction, (e.g. vertically only when correctly installed) offers the advantage of increasing the height of the implant and therefore the distraction of the disc space, but without a concomitant increase in the width of the implant.

Expandable fusion implants are known in the related art. The first expandable spinal fusion (allowing for the growth of bone from vertebral body to vertebral body through the implant) implant was invented by Michelson and also is disclosed in U.S. Pat. No. 5,776,199, filed Jun. 28, 1988, which is hereby incorporated by reference herein.

Push-in spinal fusion implants having upper and lower non-arcuate surfaces adapted for placement in contact with adjacent vertebral bodies are known in the related art. Such a push-in spinal fusion implant was invented by Michelson and is disclosed in U.S. Pat. No. 5,776,199, incorporated by reference above.

Push-in spinal fusion implants having upper and lower arcuate portions oriented toward the adjacent vertebral bodies and designed to engage the vertebral bodies along arcuate cuts therein typically formed by a drill are known in the related art. Such a push-in spinal fusion implant was invented by Michelson and is disclosed in U.S. Pat. No. 5,593,409, filed Feb. 17, 1995, which is hereby incorporated by reference. Push-in spinal fusion implants offer the advantage of being easily positioned in the implantation space and of having excellent fastening or holding features.

Threaded spinal fusion implants requiring rotation for insertion into the implantation space in the spine are known in the related art. The first artificial threaded spinal fusion implant was invented by Michelson and is disclosed in U.S. Pat. No. 5,015,247, which is hereby incorporated by reference. Threaded spinal fusion implants offer the advantage of being easily positioned in the implantation space and of having excellent fastening or holding features. Examples of instruments and methods of inserting spinal implants are taught by Michelson in U.S. Pat. No. 5,484,437 and U.S. Pat. No. 6,080,155, the disclosures of which are hereby incorporated by reference herein.

Lordotic or tapered, push-in spinal fusion implants are also known in the art. By way of example, Michelson has invented such implants as disclosed in U.S. Pat. No. 5,609,635, filed Jun. 7, 1995, which is hereby incorporated by reference. Lordotic, frusto-conical, or tapered, threaded spinal fusion implants are also known in the art. By way of example, Michelson has invented such implants as disclosed in U.S. Pat. No. 6,210,412, which is hereby incorporated by reference. Lordotic, frusto-conical, or tapered, push-in spinal fusion implants are also known in the art. By way of example, Michelson has invented such implants as disclosed in U.S. Application Ser. No. 08/484,928, filed Jun. 7, 1995, which is hereby incorporated by reference. Lordotic or tapered, spinal fusion implants have the advantage of restoring or enhancing spinal lordosis.

Expandable interbody spinal fusion implants preferably may be inserted from an anterior approach to the spine, an approach posterior to the vertebral transverse processes, to either side of the spinal midline in pairs, or from an anterior lateral approach to the spine. Such expandable implants are adapted to be capable of increasing in height anteriorly (at their leading ends) or posteriorly (at their trailing ends) from a first collapsed state, to a second expanded state for the purpose of increasing spinal lordosis at that interspace, or may be capable of increasing in height both anteriorly and posteriorly. During installation of expandable interbody spinal fusion implants, it is desirable that the surgeon have the ability to precisely control the implant with the appropriate instruments and methods to load the implant with appropriate bone growth promoting material, to insert the implant into the implantation space, to deploy the implant to a final expanded state, and to further load the implant with bone growth material if so desired.

There exists a need for instruments and methods for use with expandable interbody spinal fusion implants providing for all of the aforementioned needs individually or in combination.

SUMMARY OF THE INVENTION

In accordance with the purposes of the present invention, as embodied and broadly described herein, an implant holder of this invention is provided for inserting an interbody spinal implant into the spine of a human; the implant holder includes an outer sleeve having a longitudinal axis, a passage along the longitudinal axis, and a distal end with an implant engagement area adapted to cooperatively engage the implant. The implant holder also includes a shaft having a passage. The shaft is adapted to move along at least a portion of the passage of the outer sleeve. The passage of the shaft is adapted to permit the passage of an instrument or fusion promoting substances therethrough.

In accordance with the purposes of another embodiment of the present invention, as embodied and broadly described herein, an apparatus of this invention is provided for inserting an expandable spinal implant having an expander adapted to increase the height of the implant; the apparatus including an implant holder having a longitudinal axis, a passage along the longitudinal axis, and a distal end with an implant engagement area adapted to cooperatively engage the implant. The implant holder also includes an expander driver adapted to engage the expandable implant. The expander driver has a shaft adapted to pass through the passage of the implant holder. The shaft of the expander driver has a distal end adapted to engage the expander of the expandable implant.

In accordance with the purposes of another embodiment of the present invention, as embodied and broadly described herein, an implant holder is provided for inserting an expandable spinal implant, the implant holder remaining attached to the spinal implant while the spinal implant is expanded from an unexpanded position to an expanded position within an implantation space prepared for receiving the spinal implant.

In accordance with the purposes of yet another embodiment of the present invention, as embodied and broadly described herein, an implant holder of this invention is provided for inserting an interbody spinal implant having a trailing end; the implant holder including a body having a distal end, a proximal end, and a length therebetween. The implant holder also includes at least two extensions extending from the distal end of the body. The extensions have an interior surface and an exterior surface opposite the interior surface. The extensions are adapted to be moved toward one another by an inward force applied to the exterior surface to permit the extensions of the implant holder to pass into the trailing end of the implant and for the exterior surface to cooperatively engage the trailing end of the implant after the inward force is removed.

In accordance with the purposes of a further embodiment of the present invention, as embodied and broadly described herein, a method of this invention is provided for expanding an expandable spinal implant having an expander adapted to increase the height of the implant. The method includes the steps of providing an implant holder having a passage therethrough adapted to receive an expander driver; attaching the implant holder to the implant; inserting the expander driver having a shaft through the passage of the implant holder to engage the expander of the implant; and rotating the expander driver to expand the expandable implant.

In accordance with the purposes of another embodiment of the present invention, as embodied and broadly described herein, a method, of this invention is provided for loading a spinal implant with fusion promoting substances. The method includes the steps of providing an implant holder having a passage therethrough; attaching the implant holder to the implant; and passing fusion promoting substances through the passage of the implant holder into the implant.

In accordance with the purposes of yet another embodiment of the present invention, as embodied and broadly described herein, a method of this invention is provided for inserting an interbody spinal implant into an implantation space, the method including the steps of providing an implant holder having a body having a distal end, the implant holder having extensions extending from the distal end of the body, the extensions having an exterior surface, the extensions being adapted to be moved toward one another by an inward force applied to the extensions to permit the extensions of the implant holder to pass into the trailing end of the implant and for the exterior surface to cooperatively engage the implant after the inward force is removed; passing the extensions of the implant holder into the trailing end of the implant; and cooperatively engaging the exterior surface of the extensions of the implant holder to the implant.

The accompanying drawings, which are incorporated in and constitute a part of this specification, are by way of example only and not limitation, and illustrate several embodiments of the invention, which together with the description, serve to explain the principles of the invention. The scope of the invention is limited only by the scope of the claims as from the present teachings other embodiments of the present invention shall be apparent to those skilled in the art.

BRIEF DESCRIPTION OF THE DRAWINGS

FIG. 5 is a side view of the implant of FIG. 1;

FIG. 6 is a cross-sectional side view along the mid-longitudinal axis of the implant of FIG. 1;

FIG. 8 is a front view of one embodiment of an expander of FIG. 1;

FIG. 9 is a side elevation view of the expander of FIG. 8;

FIG. 10 is a schematic representation of a geometric configuration of a cross-section of an embodiment of an expander for use with the instrumentation and method of the present invention;

FIG. 11 is a top plan view of an anterior lumbar expandable non-arcuate impacted interbody spinal fusion implant having two expanders shown in dashed line for use with the instrumentation and method of the present invention from the anterior approach to the spine;

FIG. 12 is a top plan view of the bottom member of another preferred embodiment of an anterior lumbar expandable non-arcuate interbody spinal fusion implant having a set of two expanders positioned on both sides of the implant mid-longitudinal axis for use with the instrumentation and method of the present invention from the anterior approach to the spine;

FIG. 13 is a side view of an implant end cap shown in partial cross section for use with the implant of FIG. 12;

FIG. 14 is a top plan view of another preferred embodiment of a posterior lumbar expandable non-arcuate interbody spinal fusion implant for use preferably in pairs with the instrumentation and method of the present invention from the posterior approach to the spine;

FIG. 15 is a top plan view in partial cross section of one embodiment of an implant holder instrument of the present invention shown in a retracted state for inserting an implant, such as for example the implant of FIG. 1;

FIG. 16 is a side elevation view in partial cross section of the holder instrument of FIG. 15;

FIG. 17 is a top plan view of one embodiment of an expander driver instrument of the present invention for rotating an expander, such as for example the expander of FIG. 1;

FIG. 18 is a side elevation view of the expander driver instrument of FIG. 17;

FIG. 19 is a top plan view of the implant of FIG. 1 in partial cross section in a non-expanded state and a top plan view in partial cross section of the holder instrument of FIG. 15 in a retracted state being positioned to engage with the implant;

FIG. 20 is a top plan view in a partial cross section of the holder instrument of FIG. 15 in an extended state, with the side extension members moved apart and engaging the flanges into complementary slots in the trailing end of the implant of FIG. 1 shown in partial cross section;

FIG. 21 is a top plan view of the holder instrument of FIG. 15 in partial cross section being rotatively locked in the extended state to keep the side extension members in engagement with the trailing end of the implant of FIG. 1 shown in partial cross section;

FIG. 22 is an exploded top plan view of the expander driver instrument of FIG. 17 being inserted into the holder instrument of FIG. 15 and into the implant of FIG. 1 shown in partial cross section;

FIG. 28 is a top plan view of a lower vertebral body and the implant of FIG. 1 in partial cross section implanted in an implantation site formed posteriorly across a disc space and the expander driver instrument of FIG. 17 being locked into a retracted position by the second spring lock of the holder instrument of FIG. 15 shown in partial cross section in engagement with the first detent of the expander driver instrument;

FIG. 29 is an enlarged fragmentary top plan view along line 29 of FIG. 28 showing the relationship between the first and second spring locks of the holder instrument and the complementary first and second detents of the expander driver instrument while the expander driver instrument is in the retracted position;

FIG. 35 is a top plan view of the expander driver instrument of FIG. 17 being withdrawn from the implant of FIG. 1 shown in an implantation site and holder instrument of FIG. 15;

FIG. 36 is a top plan view of the holder instrument of FIG. 15 and implant of FIG. 1 shown in an implantation site after the expander driver instrument of FIG. 17 has been used to pack the space in the implant left unoccupied by the removal of the expander driver instrument with bone growth promoting materials;

FIG. 42 is a top plan view of the implant of FIG. 41;

FIG. 43 is a trailing end view of the implant of FIG. 41;

FIG. 44 is a side elevation view of the implant of FIG. 41;

FIG. 45 is a leading end view of the implant with the end cap of FIG. 41 attached thereto;

FIG. 46 is a cross-sectional view along line 46-46 of FIG. 42;

FIG. 56 is a trailing end perspective view of the implant, and a leading end perspective view of the implant holder and expander driver of FIG. 55, the expander driver being shown in a retracted position within the implant holder;

FIG. 57 is a trailing end perspective view of the implant, and a leading end perspective view of the implant inserter and expander driver of FIG. 55, the expander driver being shown in a partially extended state;

FIG. 61 is a trailing end perspective view of another embodiment of an implant for use with the instrumentation and method of the present invention and the expander driver of FIG. 55;

FIG. 64 is a cross-sectional side view of the implantation site formed across the space between two adjacent vertebral bodies and the implant of FIG. 62 installed into the implantation space and anchored to the spine with bone screws;

FIG. 65 is a trailing end view of the anterior aspect of two adjacent vertebral bodies and the implant of FIG. 62 implanted therebetween in an expanded position as well as another embodiment of an implant designed to be used as a side-by-side pair;

DETAILED DESCRIPTION OF THE DRAWINGS

Figure 1A:
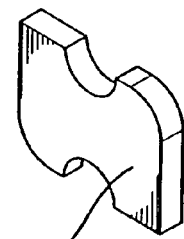
FIG. 1A is a perspective view of an alternative embodiment of a blocker in the form of an expander for use with the implant of FIG. 1.

Reference will now be made in detail to the present preferred embodiments (exemplary embodiments) of the invention, examples of which are illustrated in the accompanying drawings.

The instrumentation and method of the present invention may be used for a posterior, anterior, lateral, or posterolateral approach to the spine. The present invention in one preferred embodiment is an integrated set of instruments allowing for the performance of a method for inserting expandable non-arcuate impacted interbody spinal fusion implants, from an approach posterior to the vertebral transverse processes, to either side of the spinal midline and preferably in pairs, where the implants are adapted to be capable of increasing in height anteriorly (at their leading ends) from a first collapsed state, to a second expanded state for the purposes of inducing interspace distraction and/or of increasing spinal lordosis at that interspace. In other preferred embodiments, the instruments and methods of the present invention are used to insert expandable non-arcuate impacted interbody spinal fusion implants from an anterior approach to the spine, where the implants are adapted to be capable of increasing in height anteriorly, and if desired, both anteriorly and posteriorly including anteriorly more than posteriorly (at their leading ends). With little modification, the taught methods and instruments can also be utilized to insert such implants in a lateral orientation.

FIGS. 1-14 show preferred embodiments of an expandable interbody spinal fusion implant such as those described by Michelson in International Application No. PCT/US01/03657, entitled "Expandable Impacted Interbody Spinal Fusion Implant," the disclosure of which is incorporated by reference herein, and instruments for use therewith in accordance with the present invention. To better understand the structure and interrelationship of the instruments and the associated methods for their use, the structure and associated characteristics for one embodiment of an implant adapted to be inserted via these instruments and methods will be described first.

As shown in FIGS. 1-7, a preferred embodiment of an expandable non-arcuate impacted interbody spinal fusion implant for use with the instruments and method of the present invention is generally referred to by the number 100. Implant 100 preferably has a leading end 102, a trailing end 104, an upper member 106, and a lower member 108. Upper and lower members 106, 108 are each preferably non-arcuate and adapted for placement toward and at least in part within the upper and lower of two adjacent vertebral bodies, respectively.

As used herein the term "non-arcuate" is intended to describe the upper and lower surfaces of the implant as having (1) no curvature, as in a planar surface, (2) slight or mild curvature from the leading end to the trailing end of the implant, and/or (3) slight or mild curvature across the implant width. Slight or mild curvature does not include the curvature associated with the upper and lower surfaces of implants for insertion into a disc space having a circular cross section formed across a spinal disc and into the adjacent vertebral bodies. While the upper and lower surfaces of this one preferred embodiment of an expandable non-arcuate implant may have some curvature, in comparison to an implant having a circular cross section, the curvature is minimal. For implants having a circular cross section such as threaded implants the curvature of the upper and lower surfaces contacting the adjacent vertebral bodies is a radius of half the width of the implant. If there is a curvature to the upper and lower surfaces of the non-arcuate implant described above, the curvature is that of a circle much greater than the width of the implant; thus, it has a slight curvature that may correspond to an anatomical curvature of a disc or the surface of the vertebral endplate. Conversely, the surface may have surface protrusions that are in part arcuate but the implant itself still being generally non-arcuate.

Each of upper and lower members 106, 108 preferably have at least one opening 110 in communication with one another for permitting for the growth of bone from adjacent vertebral body to adjacent vertebral body through implant 100.

On an exterior surface 112 of each of opposed upper and lower members 106, 108 is at least one bone-engaging projection 114 adapted for linear insertion, which in one preferred embodiment is a ratchet. Alternatively, bone engaging projection 114 can be a surface roughening, knurling, spline, or any other configuration suitable for the intended purpose of resisting expulsion of the implant from the disc space after implantation.

Upper and lower members 106, 108 are moveable relative to one another and have a first position that allows for a collapsed implant height and a second position that allows for an increased height. In the first position, upper and lower members 106, 108 may be parallel to one another, but also can be angled if desired. Upper and lower members 106, 108 are preferably articulated at an articulation point proximate trailing end 104 of implant 100. Upper and lower members 106, 108 are articulated to one another so one of the respective ends of upper and lower members 106, 108 remain articulated while the other of the respective ends of upper and lower members 106, 108 are free to move away from one another As shown in FIG. 1, by way of example, upper and lower members 106, 108 preferably have a cooperating rotational articulation or pivot point 116 between upper and lower members 106, 108. The cooperating rotational articulation 116 preferably is proximate one of the proximal end and the distal end of upper and lower members 106, 108 at an end opposite to an expanding mechanism or expander 120.

Figure 7:
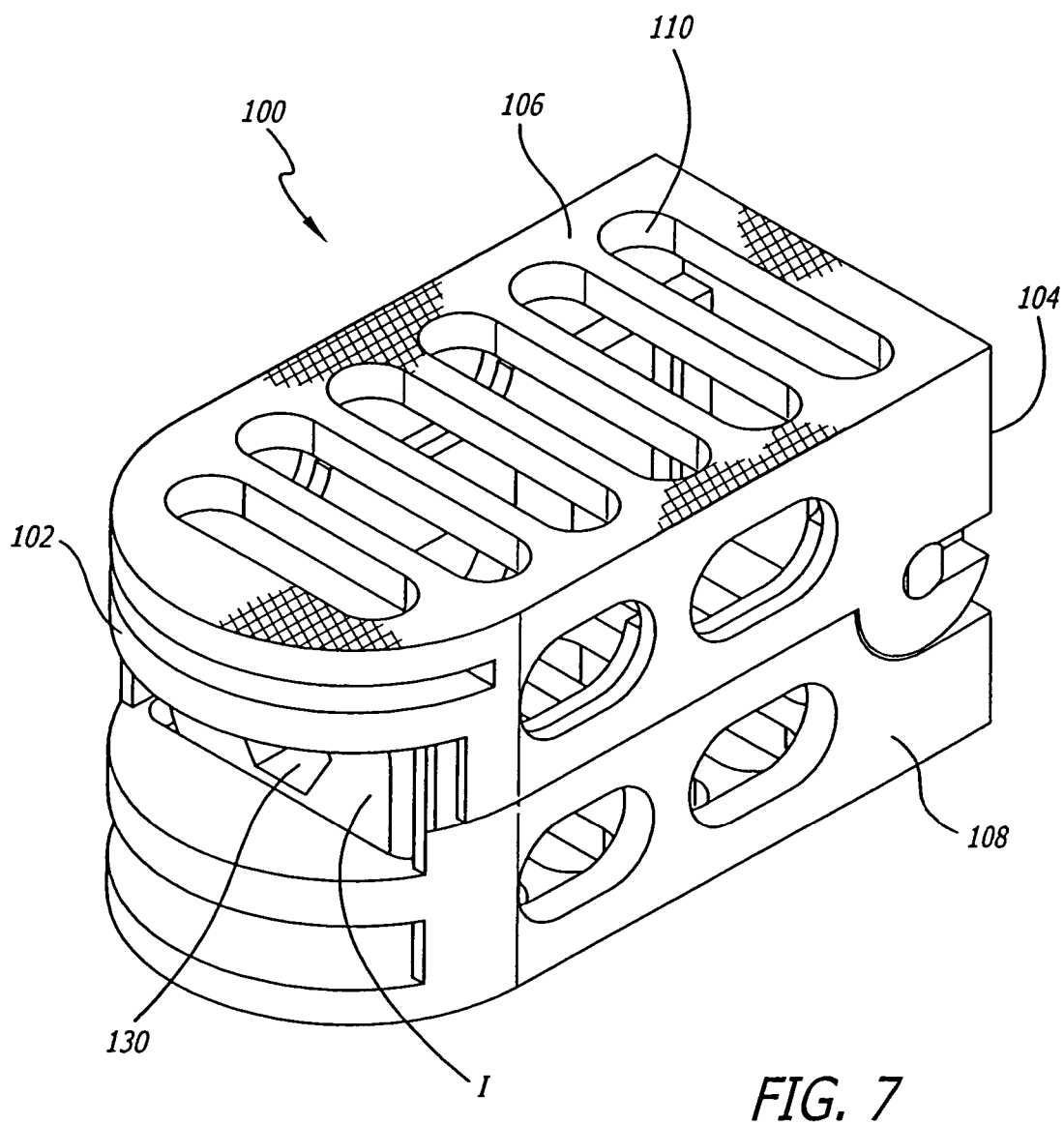
FIG. 7 is a leading end perspective view of the implant of FIG. 1.

Each of upper and lower members 106, 108 of the implant of FIG. 1 preferably has a track 122, 124 within which expander 120 rotates. As best shown in FIGS. 1 and 7 track 122, 124 is configured to permit expander 120 to rotate therein and then to move from side to side within track 122, 124.

A slot 126 on implant 100 is adapted to cooperatively engage and may lockably attach to an implant holder 500 (described below) and to thereafter, if so desired by the surgeon, receive a cap that snaps into slot 126.

FIGS. 8-10 show various views of an expander element for use with expandable spinal fusion implants adapted for use with the instruments and methods of the present invention.

Figure 1B:
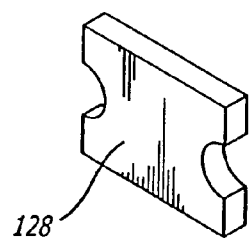
FIG. 1B is a perspective view of another alternative embodiment of a blocker for use with the implant of FIG. 1.
Figure 1C:
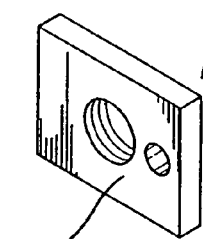
FIG. 1C is a perspective view of yet another alternative embodiment of a blocker for use with the implant of FIG. 1.
Figure 1:
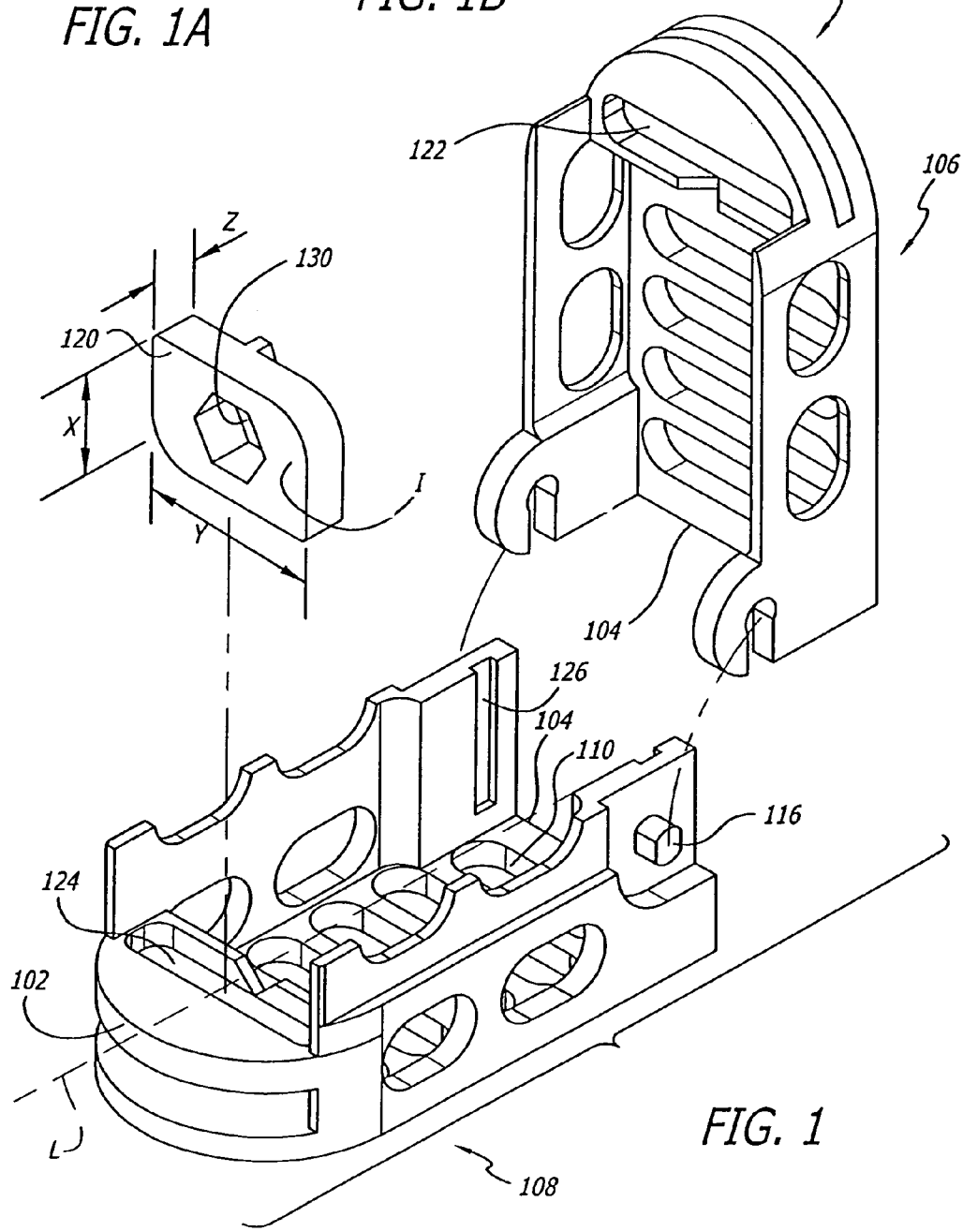
FIG. 1 is an exploded perspective view of an embodiment of a posterior lumbar expandable non-arcuate impacted interbody spinal fusion implant for use with the instrumentation and method of the present invention.
Figure 2:
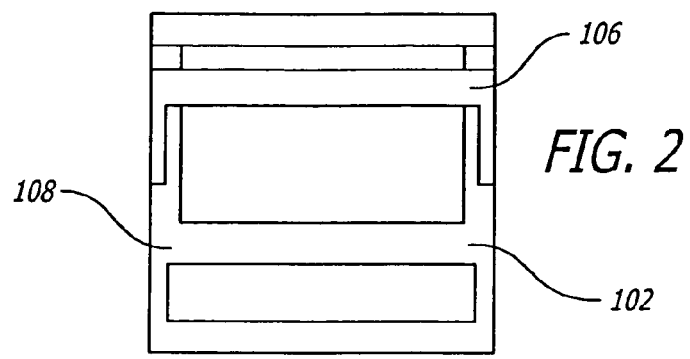
FIG. 2 is a leading end view of the implant of FIG. 1.
Figure 3:
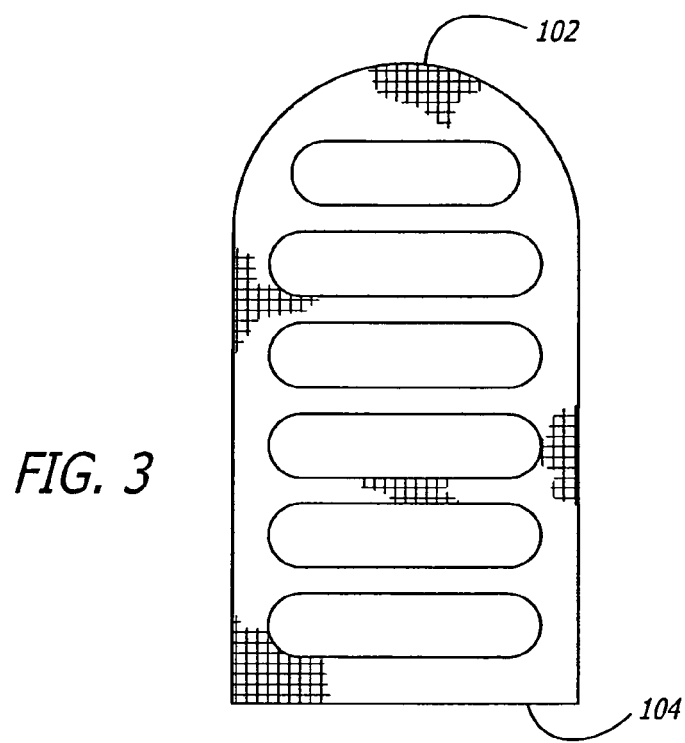
FIG. 3 is a top view of the implant of FIG. 1.
Figure 4:
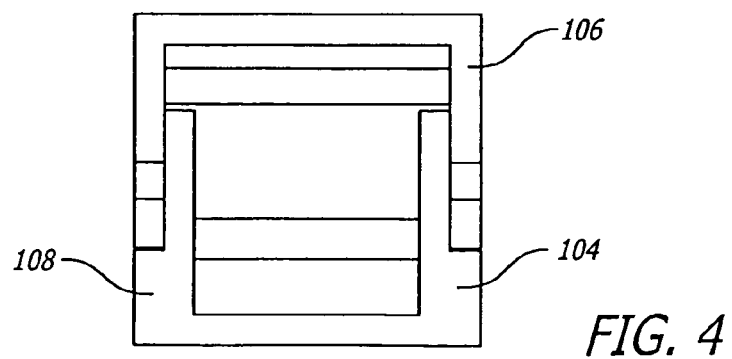
FIG. 4 is a trailing end view of the implant of FIG. 1.

While a specialized form of a blocker 128, such as shown in FIGS. 1B and 1C, is described in detail below with reference to expander 120, blocker 128 need not be in contact with upper and lower members 106, 108 when implant 100 is initially inserted into the implantation space. Blocker 128 may be a block or any type of spacer that is inserted between the articulated upper and lower members 106, 108 after implant 100 is positioned so as to hold portions of the upper and lower members 106, 108 spaced apart at the optimal height and angulation relative to one another. That is the implant may be expanded with an expander driver 600, described in more detail below, and then the expanded portions held apart in the second position by a third body blocker placed therebetween. Further, a physician may be able to select from a series of blockers having different heights usable with the same implant.

Blocker 128 that is preferably in the form of expander 120 is located proximate at least one of the ends of implant upper and lower members 106, 108 and holds at least a portion of upper and lower members 106, 108 apart so as to maintain the increased height of implant 100 and resist the collapse of implant 100 to the collapsed implant height. Expander 120 in the present embodiment increases the implant height as measured in a plane passing through the mid-longitudinal axis of implant 100 and upper and lower members 106, 108 during positioning of expander 120 and as may be desirable is capable of selectively increasing the height of the implant only.

Figure 34:
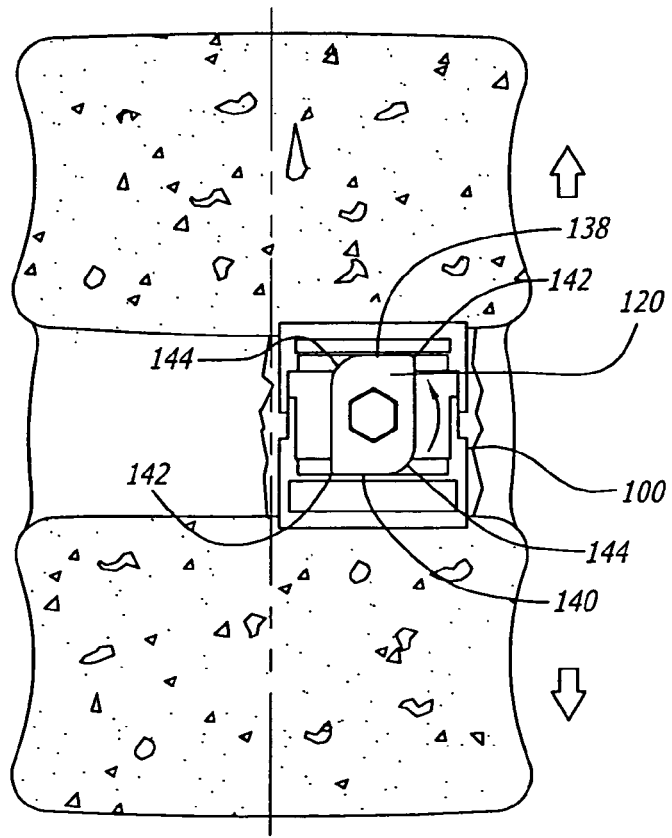
FIG. 34 is a partial cross-sectional leading end view of the implant of FIG. 1 implanted between adjacent vertebral bodies with the expander in the final deployed position.

Expander 120 in the present embodiment is adapted to rotate in a single direction approximately 90 to move from an initial (first) insertion position I, as best shown in FIGS. 1 and 7, to a final (second) deployed or expanded position F, as best shown in FIG. 34, to increase the maximum height H of implant 100.

Expander 120 has an opening 130 adapted to cooperatively engage expander driver 600 used to rotate expander 120 to increase height H of implant 100. Expander driver 600 preferably rotates about an axis parallel to the longitudinal axis L of implant 100 to rotate expander 120 to increase height H of implant 100. Opening 130 also may be used as a passageway to pass fusion-promoting materials through expander 120 and into implant 100.

In rotating the expander, the longer dimension of the expander is substituted for the lesser dimension of the expander thus correspondingly increasing the maximum height of the implant from the first to the second position.

As best shown in FIG. 10, the schematic representation of a geometric configuration of a cross-section of an expander 120 in accordance with one embodiment of the present invention, includes: a first dimension X corresponding to the height of expander 120 when implant 100 is initially inserted into the spine and to the width of expander 120 when expander 120 is rotated to increase height H of implant 100; and a second dimension Y corresponding to the width of expander 120 when implant 100 is initially inserted into the spine and to the height of expander 120 when expander 120 is rotated to increase height H of implant 100. Second dimension Y is greater than first dimension X. Preferably, expander 120 offers a surgeon multiple sensory advantages including: the tactile feel of expander 120 going over center and locking into place; the visual of the handle of a tool rotating expander 120 such that the tool handle goes from perpendicular to parallel, the reverse, or other, to the disc space into place; and auditory from the sound of expander 120 snapping into place.

As shown in FIGS. 1 and 7, in one preferred embodiment of the present invention for posterior insertion, expander 120 is located proximate the leading end 102 of upper and lower members 106, 108. It is appreciated that depending on the intended results, the expander also may be located at trailing end 104 of upper and lower members 106, 108 or anywhere else within the implant. Moreover, multiple expanders may be used in contact with upper and lower members 106, 108 at any location within implant 100.

FIGS. 11-14 show various views of other embodiments of expandable interbody spinal fusion implants adapted for use with the instrumentation and methods of the present invention. As shown in FIGS. 11 and 12, implants 200 and 300 are similar to implant 100 except that they are designed for insertion from an anterior to posterior direction and to fill more than half the width of the disc space. Implants similar to 200 and 300 may have a pivot at the leading end and an expander or expanders at the trailing end as with the earlier described posterior insertion implant, such that the implants will get taller at their trailing ends instead of their leading ends to restore lordosis.

As actually shown in FIG. 11, implant 200 has two expanders 220 for moving at least a portion of the upper and lower members away from one another to increase the height of implant 200. All of the features described herein for the single expander 120 of implant 100 of FIGS. 1-7 may also be applicable to both expanders 220 of implant 200. Additionally, second expander 220 may be located proximate an end of implant 200 opposite other expander 220, thereby providing implant 200 the capability of being expanded at both ends 202, 204 of implant 200. The increased height of implant 200 resulting from moving two expanders 220 may be constant or varied along the length of implant 200 according to the desired configuration of implant 200. Implant 200 may also be embodied to have a single expander at its trailing end and a pivot point at its leading end.

FIG. 12 shows another preferred embodiment of an expandable non-arcuate interbody spinal fusion implant for use from the anterior approach with the instrumentation and methods of the present invention generally referred to by the number 300. In implant 300 two sets of expanders 320 are used, each set being located on one side of the mid-longitudinal axis of implant 300. Depending upon the type of articulation used, expanders 320 may be rotated to confer a transverse angulation as well as longitudinal angulation to upper and lower members 306, 308 in situations where such angulation is desired. All four expanders 320 may be used to expand upper and lower members 306, 308 by the same or different amount relative to one another. This can be done to permit the surgeon to expand the leading and trailing ends or sides by varying degrees.

As shown in FIG. 13, a cap 334 having an exterior surface and an interior surface may be used to close trailing end 302 of implant 300. As may be appreciated by those skilled in the art, cap 334 may be adapted for attachment to implant 300 in a number of ways. For example, the interior surface of cap 334 may have spaced slots about its circumference to facilitate a snap fit between cap 334 and the implant 300, or the rim of cap 334 may be threaded for rotational engagement with trailing end 302 of implant 300. Further, cap 334 may be solid or perforate and made of a surgical quality plastic that may be resorbable or of any other suitable material. Cap 334 may also be adapted to prevent over-expansion of implant 300. Examples of caps for preventing over-expansion of implants are taught by Michelson in U.S. Provisional Application No. 60/274,869, the disclosure of which is hereby incorporated by reference herein.

FIG. 14 shows another preferred embodiment of an implant for use from a posterior approach with the instrumentation and methods of the present invention generally referred to by the number 400. Implant 400 has an expander 420 at its leading end 402. Leading end 402 is shaped to generally conform to the anatomical configuration of the anterior aspect of the vertebral body to prevent the anterior lateral aspect of the implant from protruding from the spine. Implant 400 with little modification is also useful for bilateral anterior hemi (half width) implant insertion such as might be desirable for laproscopic insertion.

Though described in relation to posterior and anterior approaches, the push-in implant of the present invention also may be used for insertion from the translateral aspect of the spine as disclosed by Michelson in U.S. Pat. No. 5,860,973, which is incorporated herein by reference. In which case, the implants would expand at least anteriorly to increase the disc space height and/or restore lordosis.

FIGS. 15-18 show various views of instruments adapted for inserting and expanding spinal fusion implants such as those previously described. Unless otherwise noted, the instruments and their use will be described in relation to implant 100 and other expandable implants.

FIGS. 15 and 16 show a preferred embodiment of an implant holder 500 for inserting implant 100 into a disc space. Implant holder 500 has a shaft 502 and an outer sleeve 504. Shaft 502 has a distal end 506, a proximal end 508, a reduced portion 510 extending towards distal end 506, an intermediate reduced portion 511, and an enlarged portion 512 between intermediate reduced portion 511 and proximal end 508. The transition from enlarged portion 512 and intermediate reduced portion 511 preferably forms a shoulder adapted to abut proximal end 524 of outer sleeve 504. Shaft 502 is preferably hollow and is adapted to permit the passage of other instruments therethrough as described below. Reduced portion 510 has a shoulder 514 at distal end 506 sized and shaped to cooperatively engage with the distal end of outer sleeve 504 to lock implant holder 500 to implant 100 in order to hold and manipulate the implant during insertion into the disc space. As used herein, the term "lock" is intended to describe the securing of an implant to the implant holder such that the implant holder may rotate, push, pull, or otherwise orient the implant into the implantation space without the inadvertent disassociation of the implant from the implant holder. Extending from intermediate reduced portion 511 is a peg 516 proximate the leading edge of enlarged portion 512 for insertion into a slot 540 of outer sleeve 504. Proximal end 508 of enlarged portion 512 has an increased diameter adapted to receive enlarged portion 612 of an expander driver 600. Proximal end 508 has a cutout 518 for receiving a peg 622. Cutout 518 has a slot 520 for receiving peg 622 of expander driver 600 to prevent expander driver 600 from rotating relative to implant holder 500.

Outer sleeve 504 has a distal end 522 and proximal end 524. Distal end 522 has upper and lower extensions 526, 528, and side extensions 530 adapted to cooperatively engage trailing end 104 of implant 100. Side extensions 530 each have a flange 532 to cooperatively engage slot 126 of implant 100 and a stop 534 for limiting further advancement of implant holder 500 into trailing end 104 of implant 100.

As shown in FIGS. 15, 19, and 20, side extensions 530 each have an interior surface 536 with a ramp portion 538. Ramp portion 538 interacts with the nose of shoulder 514 of shaft 502, which is preferably beveled to facilitate spreading apart side extensions 530 and engaging flanges 532 with slots 126 of implant 100.

FIGS. 17 and 18 show a preferred embodiment of expander driver 600 for engaging and rotating expander 120. Expander driver 600 has a shaft 602 with a distal end 604, a proximal end 606, a reduced portion 608, an implant holder engagement portion 610, and an enlarged portion 612. Shaft 602 has a generally circular cross section and is adapted to preferably coaxially engage the interior of shaft 502 of implant holder 500 to maintain vertical alignment between expander driver 600 and implant holder 500. Distal end 604 has a tip 614 adapted to cooperatively engage opening 130 of expander 120. In a preferred embodiment, tip 614 is hex-shaped, but may be of any shape suitable to engage expander 120.

Implant holder engagement portion 610 has a first, distal detent 616 and a second, proximal detent 618 for lockable engagement with implant holder 500, described in more detail below with reference to FIGS. 23, 24, 28, and 29. Enlarged portion 612 is preferably sized and shaped to fit into and rotate within proximal end 508 of implant holder 500. Enlarged portion 612 has a shoulder 620 and a peg 622 for cooperating with cutout 518 and slot 520 of implant holder 500 to limit the rotation of expander driver 600 while engaged with implant holder 500. Proximal end 606 has a T-shaped handle 624 for manual rotation of expander driver 600. Handle 624 may be removable such as a quick release handle. In instances where two expander drivers 600 are to be used simultaneously, it may be preferable to have each of two separate expander drivers 600 use an "L" shaped handle so that both implants may be expanded simultaneously without the handles hitting each other. Other handles, such as handles oriented in different planes, could also be used, and any combination of handles suitable for the purpose as would be readily apparent to one of ordinary skill in the art is within the scope of the present inventive teaching.

FIGS. 19-38 show various steps of a preferred method for inserting implant 100 and using associated instrumentation disclosed herein from a posterior approach to the spine.

The surgeon first identifies the correct disc space to be operated upon by direct inspection or by radiographic means such as a radiopaque marker and an x-ray or image intensifier. The disc is then surgically accessed from a position posterior to the transverse processes of the vertebrae to be fused. Sufficient laminar bone is removed to allow sufficient access to the posterior aspect of the disc space. The surgeon may then remove disc material that is at least sufficient to create the discal portion of an implant receiving space. Alternatively, the surgeon may first insert a guard and then with the use of the guard remove at least sufficient disc material to create the discal portion of an implant receiving space. With the dural sac safely retracted and protected to the side opposite the insertion, and with the proximate nerve roots protected as necessary, the surgeon may elect to insert a guard such as set forth in Applicant's copending U.S. Patent Application Ser. No. 60/272,381 entitled "Dynamic Lordotic Guard with Movable Extensions for Creating an Implantation Space Posteriorly in the Lumbar Spine and Method for use Thereof", incorporated by reference herein. The dynamic guard is a pivotable extended outer sleeve to protect adjacent delicate neurological structures and induce lordosis to the adjacent vertebral bodies. Although the dynamic guard is preferred for its use in restoring lordosis to adjacent vertebral bodies, it will be appreciated by those of ordinary skill in the art that other guards may be used to protect the dural sac in instances where it is desired to use a guard to protect the dural sac.

The disc space is then prepared by a bone removal instrument to receive a correctly sized implant 100. Preferred instruments and methods of preparing the disc space are disclosed and taught by Michelson in U.S. patent application Ser. No. 09/972,560 entitled "Spinal Interspace Shaper"; U.S. Pat. No. 6,083,228 entitled "Device and Method for Preparing a Space Between Adjacent Vertebrae to Receive an Insert"; U.S. Pat. No. 6,224,607 entitled "Instrument And Method For Creating An Intervertebral Space For Receiving An Implant"; and WIPO publication WO 99/63891 entitled "Device for Preparing a Space Between Adjacent Vertebrae to Receive an Insert," the disclosures of which are all herein incorporated by reference. Where it is desirable to leave a guard for protecting adjacent delicate neurological structures in place after the preparation of the disc space, the described operation can be performed through the guard and be removed at its completion. It is generally preferred that the procedure be performed on both sides of the spinal midline and that two implants 100, each having a width less than half the width of the disc space be inserted from a posterior to anterior approach either generally parallel, or alternatively from a generally posterior to anterior approach in a "toed-in" configuration.

Preferably prior to insertion, implant 100 may be loaded with fusion promoting materials including any of, or any combination of, bone in any of its forms, materials derived from bone, bone morphogenetic proteins, mineralizing proteins, hydroxyapatite, genetic materials coding for the production of bone or any substance capable of inducing the formation of bone or useful for achieving fusion for the intended purpose. Implant 100 may also be combined with an antimicrobial material. In order to best accommodate the presence of fusion promoting materials, implant 100 preferably has a hollow 118, as shown in FIG. 6, between the ends that is unobstructed by an expander 120 so as to allow for the unimpeded loading of the interior of the implant. Further, this preferred configuration of implant 100 makes available all of the volume of the hollow to contain fusion-promoting materials and so as to permit for the growth of bone directly through the hollow unobstructed by any expansion mechanism, to adjacent vertebral bodies. The method and instrument of the present invention may also be useful for expandable implants that are not so unobstructed. The fusion promoting materials may be loaded or preferably compressively loaded into implant 100 by use of an instrument such as, for example, a tamp, press, or piston at any time during the procedure as desired by the surgeon.

As shown in FIGS. 19 and 20, the distal end of implant holder 500 is inserted into trailing end 104 of implant 100 such that flanges 532 of outer sleeve 504 are positioned for engagement with slots 126 of implant 100. In FIG. 20, shaft 502 is moved to an extended position within outer sleeve 504 by linearly advancing reduced portion 510 of shaft 502 through outer sleeve 504. This allows shoulder 514 to contact ramp portion 538 of each side extension 530 and force apart each side extension 530 until flanges 532 engage slots 126 of implant 100 to engage outer sleeve 504 to implant 100. It will be appreciated that instead of forcing side extensions 530 away from one another, the implant holder may be adapted so that the side extensions may be forced toward one another to lock the implant to the implant holder. Such an embodiment is described below with relation to FIG. 67.

In FIG. 21, shaft 502 is rotated relative to outer sleeve 504 such that peg 516 moves to a locked position within L-shaped slot 540 of outer sleeve 504, thereby locking shaft 502 into an extended position within outer sleeve 504. With implant holder 500 lockably engaged to implant 100, the surgeon can manipulate implant 100 (i.e., push or pull) without the danger of implant 100 and implant holder 500 being disconnected. When implant holder 500 is connected to trailing end 104 of implant 100, the material within implant 100 may be further compressed and/or extruded into and through the opening(s) in the vertebrae engaging surfaces of implant 100 by, for example, using an instrument such as expander driver 600 to push bone growth promoting materials through implant holder 500.

Figure 23:
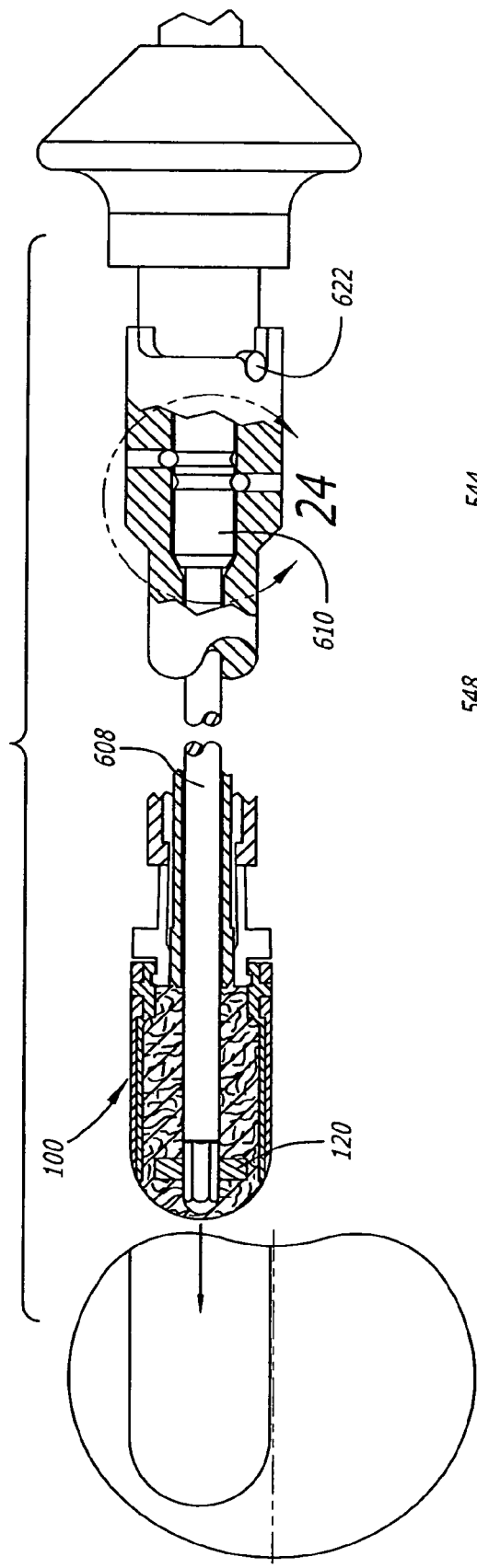
FIG. 23 is a top plan view of the expander driver instrument of FIG. 17 locked into an extended position by first and second spring locks of the holder instrument of FIG. 15 shown in partial cross section, each spring lock adapted to engage with complementary first and second detents on a shaft of the expander driver instrument and about to insert an implant into an implantation space.
Figure 24:
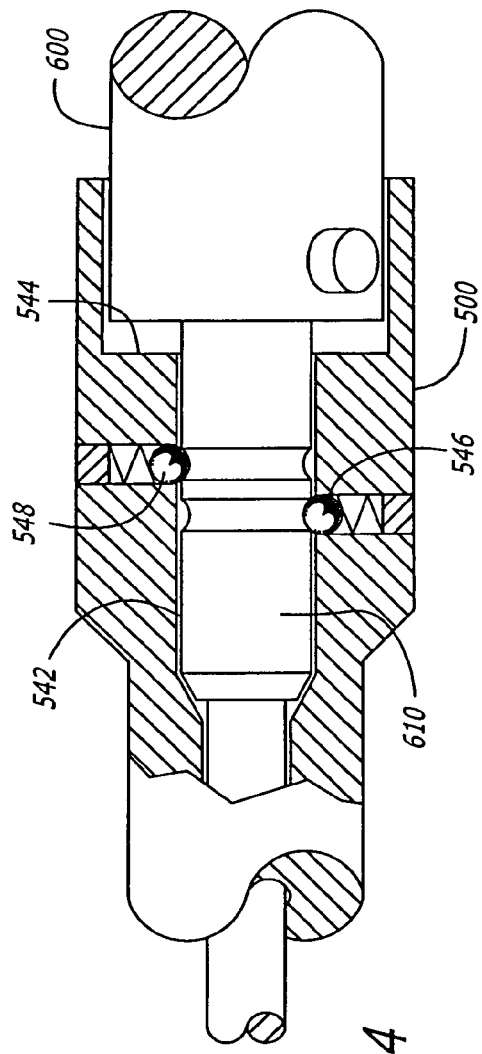
FIG. 24 is an enlarged fragmentary top plan view along line 24 of FIG. 23 showing the relationship between the first and second spring locks of the holder instrument and the complementary first and second detents of the expander driver instrument while the expander driver instrument is in the extended position.

As shown in FIGS. 22-24, distal end 604 of expander driver 600 is introduced into proximal end 508 of shaft 502 and advanced through implant holder 500 into implant 100. The leading end of tip 614 of expander driver 600 is shaped to facilitate the instrument being advanced by a rotational movement through the implant packing material in implant 100 until it reaches and is advanced into engagement with expander 120. The depth of penetration of expander driver 600 into and through expander 120 is stopped out by the larger cross sectional dimensions of implant holder engagement portion 610 and enlarged portion 612 of expander driver 600. Expander driver 600 is then locked to implant holder 500 in a first locked position to prevent any further rotation of expander driver 600 relative to implant holder 500. This is accomplished by positioning peg 622 of expander driver 600 into receiving slot 520 at proximal end 508 of implant holder 500, and by positioning first and second spring locks 546, 548 of interior surface 542 of shaft 502 within first and second detents 616, 618 of implant holder engagement portion 610. Locking expander driver 600 to implant holder 500 in the first locked position allows handle 624 of expander driver 600 to control the manipulation of the implant itself and allows for the driving forward of implant holder 500 and implant 100 into the disc space without movement of the expander so that the implant remains in the collapsed position during insertion.

Figure 25:
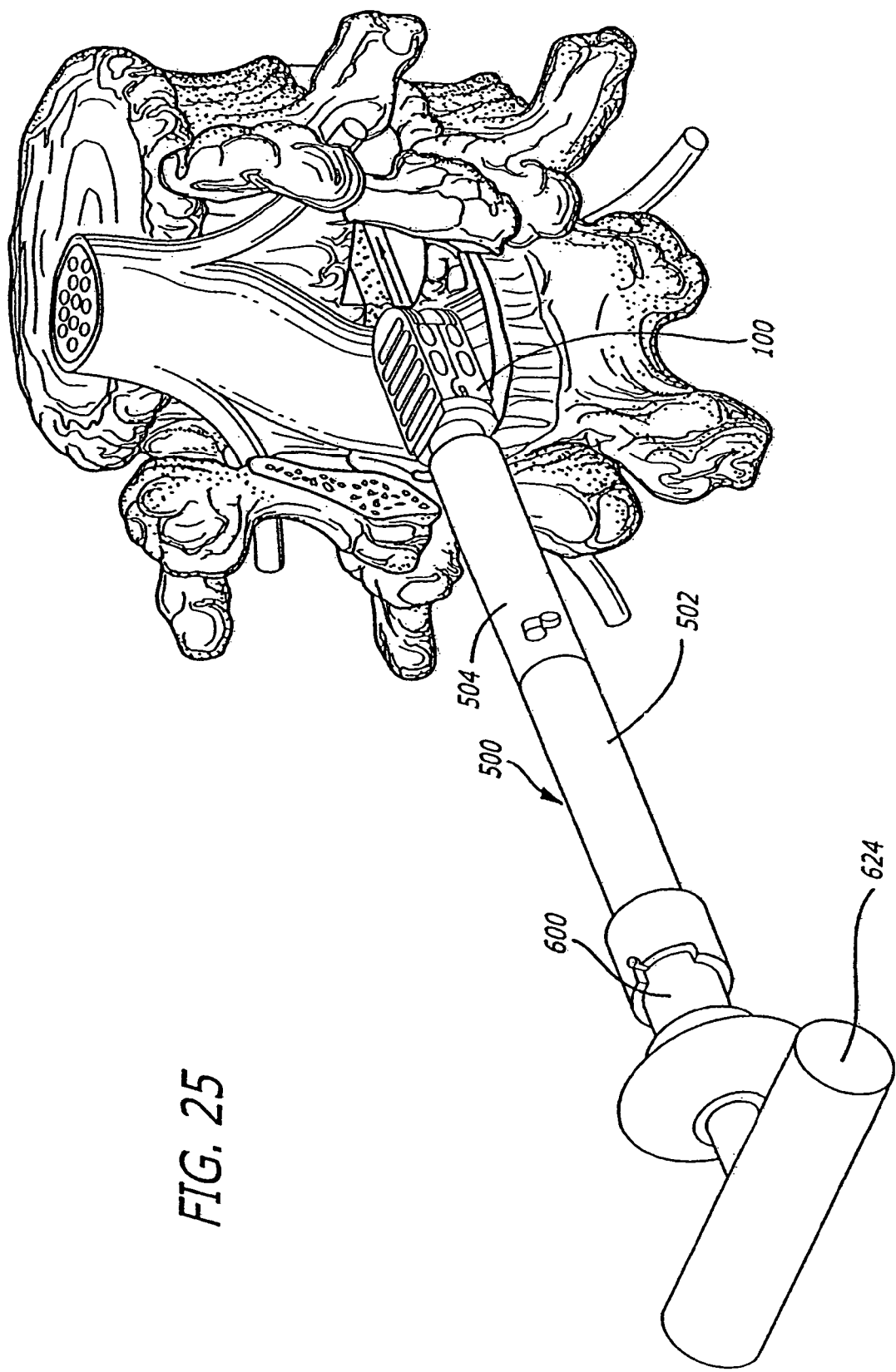
FIG. 25 is a rear perspective view of a lumbar segment of a spine with the dural sac retracted to the left showing a prepared recipient implantation site and the holder instrument of FIG. 15 with the expander driver instrument of FIG. 17 inserted therein approaching the disc space between the adjacent vertebral bodies with the implant of FIG. 1 attached thereto.
Figure 26:
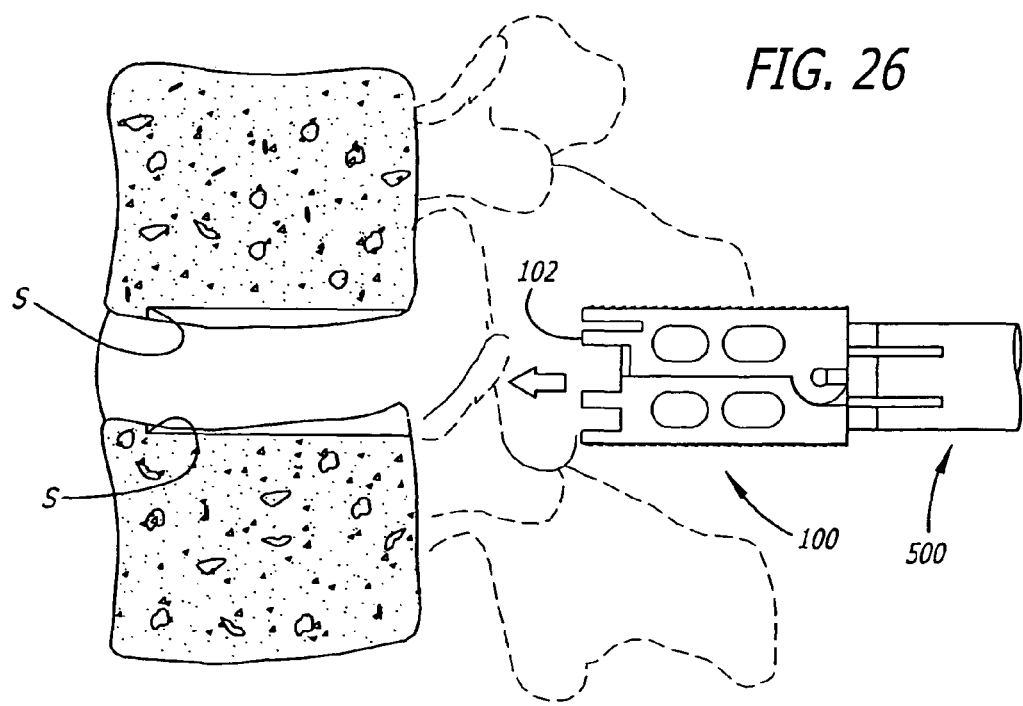
FIG. 26 is a fragmentary side view of the implant of FIG. 1 being inserted by the holder instrument of FIG. 15 through a guard from a generally posterior approach to the spine into an implantation site formed across a disc space and into two adjacent vertebral bodies of the spine shown in partial cross-section.

In FIGS. 25 and 26, implant 100 is advanced into the prepared recipient disc space by a pushing movement, an impaction force, or a combination thereof with implant holder 500. In a preferred method for preparing a recipient site, the vertebral endplates are worked upon and at least the outermost cell layers of bone are removed from the adjacent vertebral bodies to allow for fusion. But bone of the endplate region may be preserved as would otherwise be desirable to the surgeon. A preferred guard has a shaft adapted to permit the insertion therethrough of instruments used in the preparation and implantation of spinal implants, a distal end, and a proximal end. The proximal end has upper and lower members adapted for movable engagement with one another. The distal end has upper and lower disc penetrating extensions and a pivot point configured so that upon collapsing the proximal end, the upper and lower disc penetrating extensions spread apart and induce lordosis to the adjacent vertebral bodies when inserted into the disc space. Other guards serving any of the same purposes may alternatively be employed. Implant 100 is inserted to the appropriate depth which may by preference be such that trailing end 104 of implant 100 does not protrude beyond the posterior aspects of the adjacent vertebral bodies, and such that no substantial portion of implant 100 protrudes from the outer perimeter of the adjacent vertebral bodies between which implant 100 is installed. It may be desirable to "countersink" or "recess" implant trailing end 104 inside the posterior perimeter of the adjacent vertebral bodies. Implant 100 may be inserted so that it is between two adjacent vertebral bodies or at least in part within the adjacent vertebral bodies. Although use of a guard is preferred, the invention is not so limited, such that the implant may be inserted directly into the disc space as shown in FIG. 26.

Figure 27:
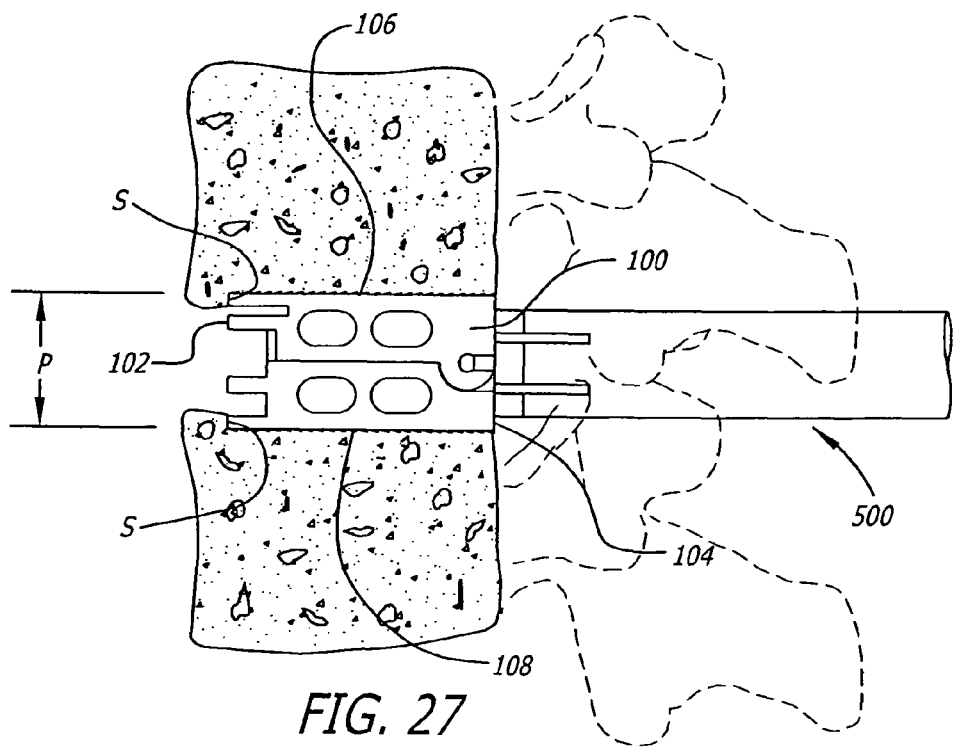
FIG. 27 is a fragmentary side view of the implant of FIG. 1 inserted by the implant holder of FIG. 15 in an implantation site formed across the disc space and into two adjacent vertebral bodies of the spine shown in partial cross section.
Figure 30:
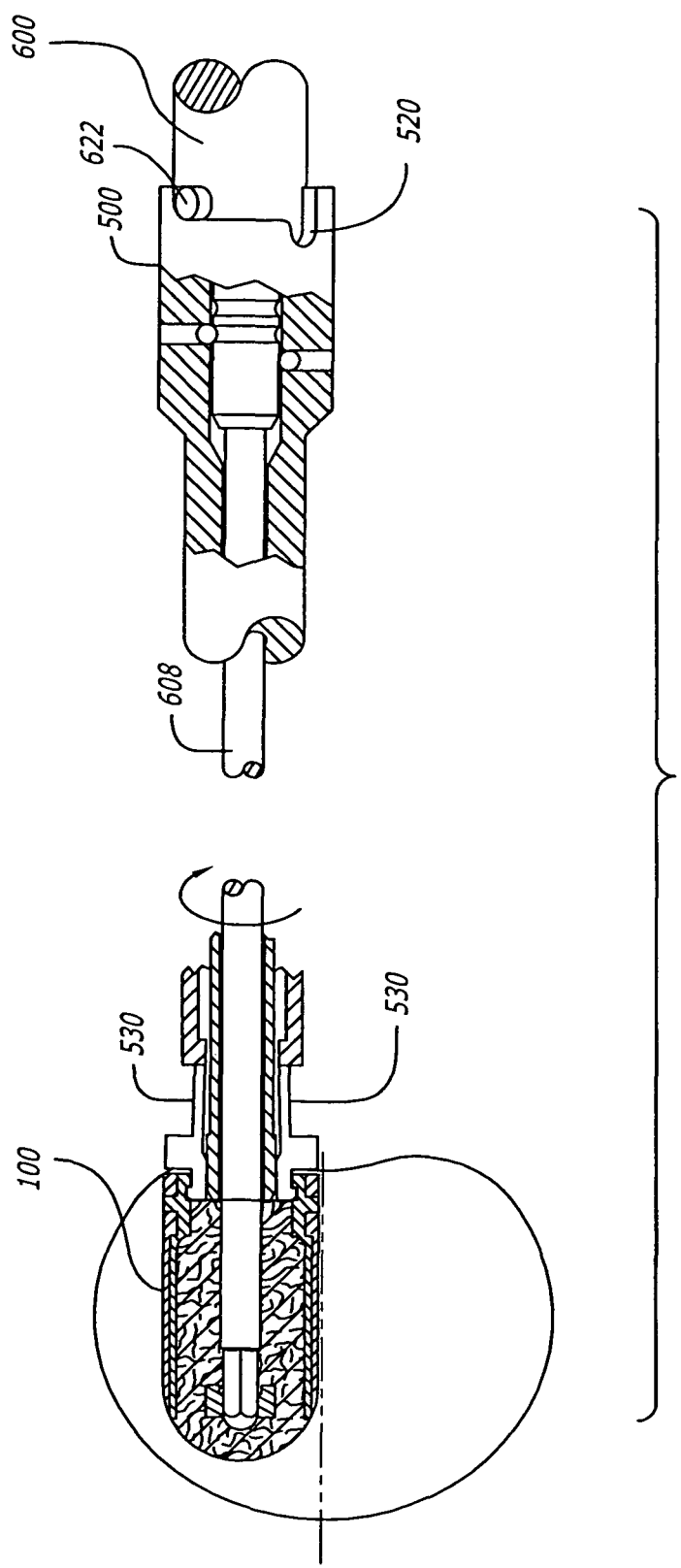
FIG. 30 is a top plan view of a lower vertebral body and the implant of FIG. 1 shown in partial cross section implanted via the holder instrument of FIG. 15 shown in partial cross section in an implantation site formed posteriorly across a disc space and the expander driver instrument of FIG. 17 moving the expander of FIG. 1 to expand the implant.

As shown in FIGS. 26 and 27, it is appreciated that the adjacent vertebral bodies need not be in an angular relationship to each other prior to insertion of implant 100. For example, implant 100 may be inserted into the disc space in a parallel orientation with the vertebral bodies in a parallel relationship to each other as shown in FIGS. 26 and 27. The advancement of implant 100 would then continue into the disc space in a parallel orientation P until leading end 102 of implant 100 encounters upper and lower shoulders S.

At this point the surgeon has a number of options for completing the procedure, two of which are preferred and described below.

One option is to complete the procedure on one of either the left or right side of the spine before repeating the procedure on the other side of the spine. Another option is to implant two implants in an unexpanded state and then expand each one, preferably simultaneously. Though both methods will be described, attention will first be directed to the method by which the implantation and expansion are performed on a first side prior to implant implantation on the second or other side.

In FIGS. 28 and 29, expander driver 600 is partially retracted from the first locked position to a second locked position such that second spring lock 548 of implant holder 500 engages first detent 616 of expander driver 600. Expander driver 600 in this position is rotatable relative to implant holder 500, so that peg 622 of expander driver 600 exits slot 520 and is free to rotate within cutout portion 518 of implant holder 500. Preferably, cutout portion 518 is shaped and sized such that after exiting slot 520, the travel of peg 622 is limited to approximately 90 degrees in a clock-wise direction from the top of slot 520. This configuration of cutout portion 518 facilitates a properly guided rotation of expander 120, which is configured for clock-wise rotation only when expanding the implant.

Figure 31:
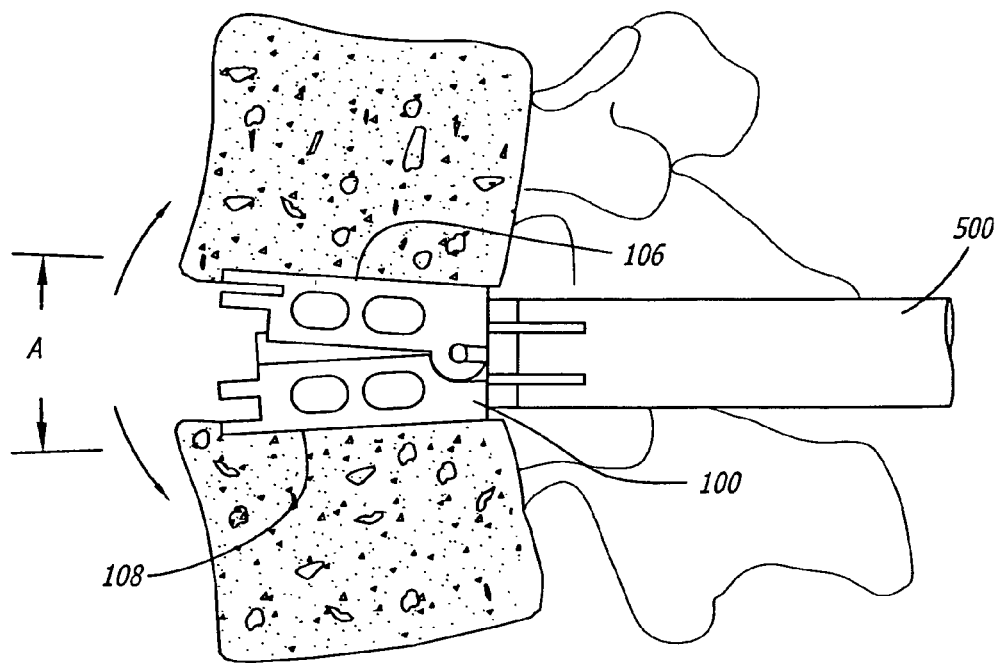
FIG. 31 is a partial side view of the implant of FIG. 1 and the holder instrument of FIG. 15 with the implant in an expanded position inserted in an implantation site formed across the disc space and into two adjacent vertebral bodies of the spine shown in partial cross section.
Figure 32:
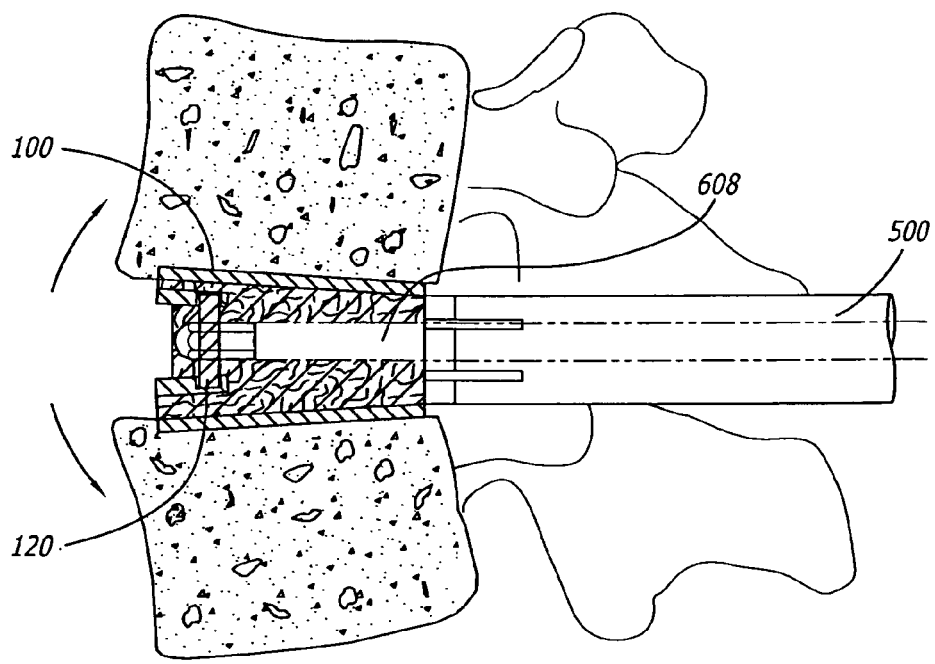
FIG. 32 is a side view of the implant of FIG. 1 in partial cross section and holder instrument of FIG. 15 with the expander driver instrument of FIG. 17 engaging the expander of FIG. 1.

As shown in FIGS. 30-34, after implant 100 is properly seated in the disc space, expander driver 600 is rotated to move expander 120 so that at least leading end 102 of implant 100 is expanded so as to increase the maximum implant height which is proximate leading end 102. One purpose of expanding implant 100 is to place the adjacent vertebral bodies in angulation to another, or in lordosis in this example. During rotation of expander 120, upper and lower members 106, 108 move from parallel orientation P, as shown in FIG. 27 where implant 100 is in a first position, to an angled orientation A, as shown in FIG. 31 where implant 100 is in a second position.

Figure 33:
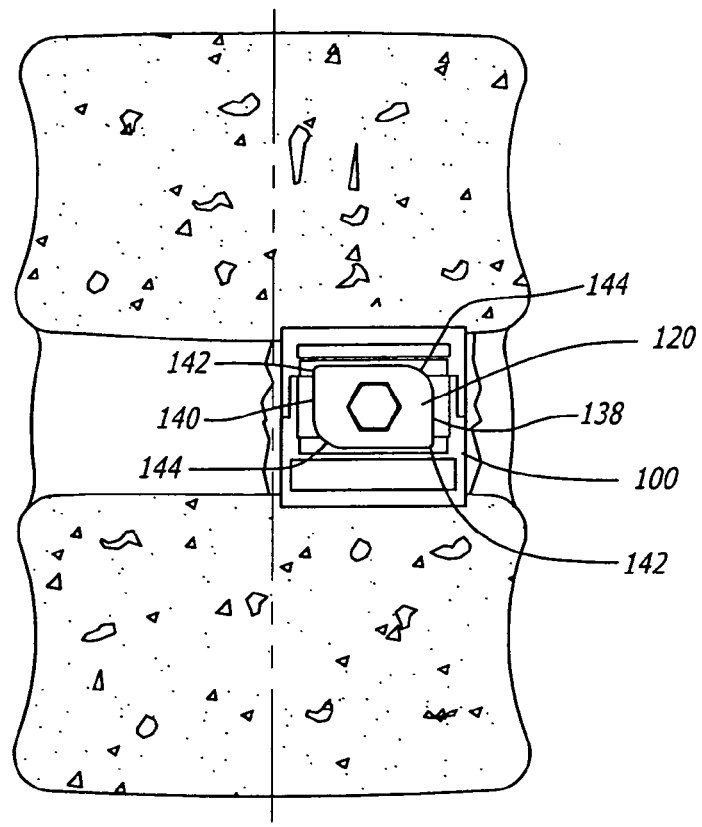
FIG. 33 is a partial cross-sectional leading end view of the implant of FIG. 1 implanted between adjacent vertebral bodies with the expander in the initial insertion position.

As shown in FIGS. 10, 33, and 34, expander 120 in one embodiment of the present embodiment has a cross-section with side surfaces 136 intersecting upper and lower surfaces 138, 140 at two junctions which may be diametrically opposed corners 142 and two diametrically opposed arcs 144. Arcs 144 are preferably each of the same radius and a modified hypotenuse MH between opposed arcs 144 generally approximates the distance between upper and lower surfaces 138, 140 such that, when expander 120 is rotated from an initial insertion position toward a final deployed position, no substantial over-distraction occurs between adjacent vertebral bodies. By "without substantial over-distraction" what is meant is that the modified hypotenuse MH length is closer to the expander dimension Y than to the unmodified hypotenuse UH; and is selected to allow the implant to preferably operate in the range of elastic deformation of the tissues about the operated disc space. It is appreciated that the expander also may move upper and lower members 106, 108 from a first height at each end to a second and greater height at each end. For example, expander 120 may be used to expand an implant having an angled orientation upon insertion to either a parallel or greater angled orientation upon expansion, or expand an implant having a parallel orientation upon insertion to an expanded parallel orientation upon expansion.

A given implant may be able to receive an expander selected by the surgeon at the time of surgery from a graduated series of sizes of expanders so as to allow the surgeon to select the further distraction and/or maximum height of the implant.

When said methods and instrumentation are used to install such implants posteriorly, the technique may further include the application of scar tissue inhibiting substances posterior to the implant trailing end and at the floor of the spinal canal.

As shown in FIG. 35, after implant 100 is positioned in an expanded state, expander driver 600 is removed from implant driver 500. During this portion of the surgical procedure, proximal end 508 of implant holder 500 will generally be facing upward as the patient typically will be face down on the operating table. Proximal end 508 of implant holder 500 is preferably funnel-shaped or otherwise shaped to receive an implant packing material M, for example only, morselized bone graft, bone paste, gels or putties of bone with or without minerals, or any other fusion promoting substance or combination thereof. Shaft 602 of expander driver 600 occupies a volume along the mid-longitudinal axis of implant 100 that extends substantially the length of the graft holding portion of implant 100 from and through trailing end 104 of implant 100. After implant 100 is expanded, a cleft C in the packed graft that is generally wedged shape and greater at the leading end than at the distal end is formed through and to each side of the expander driver track.

As shown in FIG. 36, bone growth promoting materials are pushed through implant holder 500 by use of expander driver 600 or another instrument such as a piston or impactor. Cleft C and the track may then be filled with fusion promoting materials from leading end 102 to trailing end 104 of implant 100. When desired, fusion promoting materials or graft may be compressively loaded into implant 100 so as to urge it towards the vertebral bodies. Further loading may be accomplished with or without implant holder 500 attached. Shaft 502 of the implant holder 500 is then rotated relative to outer sleeve 504 to move peg 516 into an unlocked position in L-shaped slot 540. Shaft 502 can then be partially retracted from outer sleeve 504 moving shoulder 514 from distal end 522 of outer sleeve 504 and allowing side extensions 530 to collapse inward so that implant holder 500 can be separated from implant 100.

Figure 37:
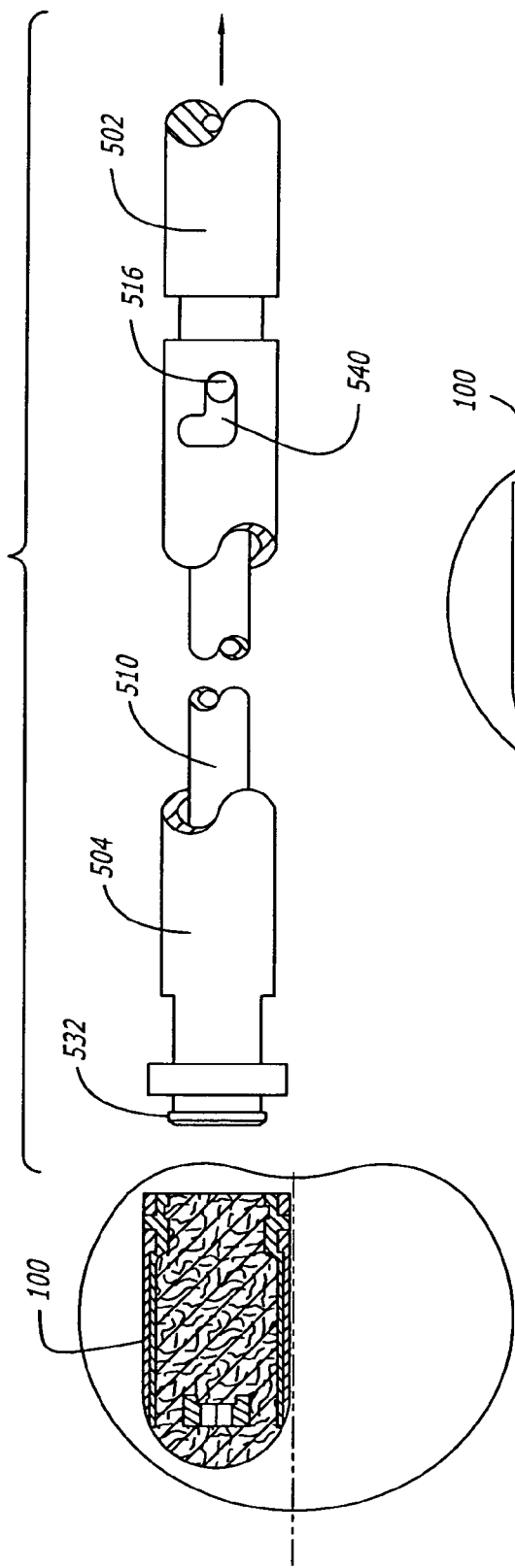
FIG. 37 is a top plan view showing the withdrawal of the holder instrument of FIG. 15 from the implant of FIG. 1 shown in an implantation space.

As shown in FIG. 37, implant holder 500 is detached from implant 100 and removed. At the surgeon's discretion, a cap may be installed to close off at least part of the implant's trailing end to prevent bone from growing into the spinal canal, or to limit adhesions of the neurological structures at the canal floor, or to otherwise protect the neurological structures. Additionally, scar tissue-inhibiting materials may be applied to the disc space and/or implant. The method includes the use of various materials including membranes and gels which may be suitable for this purpose. These materials may be used at any time after the implant(s) are inserted. One of the purposes for a cap includes restricting the passage of fusion-promoting materials so that they remain loaded within the implant. Another purpose for a cap may be to add structural support to the implant.

Figure 38:
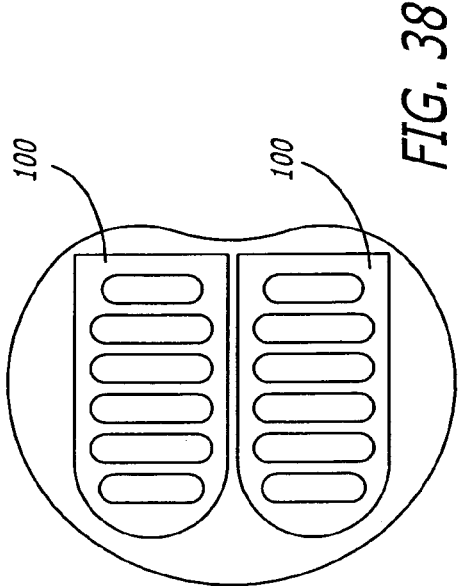
FIG. 38 is a top plan view of a lower vertebral body and two implants of FIG. 1 implanted in a final position into an implantation site formed posteriorly across a disc space.

Having completed the procedure on a first side, the procedure is then repeated as already described on the opposite side of the same disc space leading to the implantation of two implants 100 in the same disc space as shown in FIG. 38.

In summary, a preferred method of the present invention from the posterior approach to the spine includes: identifying the correct disc space to be fused; retracting and protecting the dural sac; performing at least a partial laminectomy sufficient for access to the disc space; performing at least a partial discectomy, which more preferably provides sufficient space to receive the depth of the implant; inserting a guard into the disc space; preferably inducing lordosis to the adjacent vertebral bodies prior to drilling, but alternatively after by use of the implant; and inserting a bone removal device through the guard to a desired insertion depth to create an implantation space. The depth of insertion may be monitored by x-ray.

After creation of the implantation site, the method may be continued by loading the implant with bone growth promoting materials; assembling the implant, implant holder, and expander driver together so that the expander driver is in the first locked position relative to implant holder; inserting the implant into the implantation space; retracting the expander driver to the second locked position; rotating the expander driver to move the expander and expand the implant The procedure may be continued by removing the expander driver from the implant and the implant holder; inserting fusion promoting material into the implant holder; using the expander driver as a piston to move bone growth promoting material into the interior of the implant; removing the expander driver from the implant holder; unlocking the implant holder from the implant; and removing the implant holder from the implant.

Thereafter, an end cap may be attached and scar tissue-inhibiting materials may be applied to the implant as desired. It will be appreciated by those of ordinary skill in the art that the above method may be varied according to the preferences of the attending surgeon while still being within the broad scope of the present invention. For example, the use of a guard may be omitted or used for only a portion of the procedure. The method may be performed without distracting the disc space or inducing lordosis between the adjacent vertebral bodies. The preparation of the disc space may be made with known bone drills or bone removal devices such as the Device for Preparing a Space Between Adjacent Vertebrae to Receive an Insert taught by Michelson referenced above. The implant may be loaded with bone growth promoting material before and/or after implantation. If bone growth promoting material is to be loaded into the implant after implantation, other instruments may be used in lieu of the expander driver to move the bone growth promoting material into the implant. Further steps may be included as needed, for example, when utilizing implants having bone screws and bone screw locks. In such instances, the surgeon may perform the steps of inserting a bone screw through the implant and into an adjacent vertebral body, and locking the bone screw with a bone screw lock. Additionally, further steps for correctly sizing the implant may be included such as using radiographs, CT scans, or MRIs to obtain a measurement of the disc space and thereafter treating the implant accordingly prior to insertion.

In an alternative method, both implants are placed into the disc space in a generally side-by-side configuration and aligned generally from a posterior aspect to an anterior aspect. Both implants may then be expanded simultaneously, or in close succession.

In this method, both implants may be inserted by implant holder 500 without expander driver 600 attached thereto. Instead, implant holder 500 may be adapted to have a handle to facilitate the insertion of implant 100. Once inserted, both implants receive expander drivers 600 that engage each of expanders 120 within the implants, but preferably without the presence of implant holder 500 during the expansion step. Because of the small cross sectional dimension of expander driver shafts 608 and their distance apart, the dural sac may safely run between them. As previously mentioned, it may be preferable to have each expander driver 600 comprising an "L" shaped handle so that both implants may be expanded simultaneously without the handles hitting each other. Other handles such as handles oriented in different planes, could also be used, and any combination of handles suitable for the purpose as would be readily apparent to one of ordinary skill in the art is within the scope of the present inventive teaching.

While it is preferable to have implant holder 500 in place while expanding implant 100, the invention is not so limited. Expander driver 600 may also expand implant 100 without implant holder 500. If the implants are expanded without implant holder 500 in place, then graft can be packed into the expander driver track and expansion cleft in the graft by freehand or preferably by an instrument that can align and preferably engage the trailing end of the implant distally, which is hollow, and terminates proximally in an opening formed to facilitate receiving the graft. A piston, plunger, press, or other instrument could then be used to drive the graft through the loading instrument and into implant 100.

In another alternative method, both implants may be implanted from an anterior approach to the spine. The surgeon first identifies the correct disc space to be operated upon by direct inspection or by radiographic means such as a radiopaque marker and an x-ray or image intensifier. The disc is then surgically accessed from a position anterior to the transverse processes of the vertebral bodies to be fused. Sufficient laminar bone is removed to allow sufficient access to the anterior aspect of the disc space while preserving the annulus fibrosis portion of the disc along at least both sides of the disc space.

The interspace so created is distracted and while not requisite, preferably to its optimal height, which height is determined by the known normal spatial relationships for that area the adjacent soft tissue structures. The interspace is then preferably measured for height, depth, and width. The width of the interspace may be determined in reference to the inferior portion of the vertebral endplate of the superior vertebrae, and this determines the selection of the appropriate width for a milling block or other protective guard if one is desired to be used. A preferred milling block is taught by Michelson in U.S. Pat. No. 6,159,214 entitled "Milling Instrumentation and Method for Preparing a Space Between Adjacent Vertebral Bodies," the disclosure of which is hereby incorporated by reference herein. The measured depth of the interspace, that is the distance between the front and back of vertebral body, will determine the selection of a distractor and milling means of slightly lesser depth. The height and depth of the interspace will determine the selection of the appropriate height and length of the distractor element, the shape of which is determined by both the need to either maintain or restore lordosis, as well as the shape of the implant which may or may not be wedged.

Next, the correct distractor element is selected, having either a known fixed length, or preferably is adjustable and its optimal fixed length adjusted using a calibration gauge, integral markings or similar means. The distractor apparatus is then attached to the milling block which has already been selected for the correct width.

The combined distractor apparatus and milling block assembly is then brought to the fusion site and the distractor element is introduced into the disc space. The distractor element may be introduced into the disc space turned on its side so as to facilitate introduction and then turned 90 degrees to distract the space or the distractor element may be introduced perpendicular to the plane of the disc space relying on its bullet-shaped leading edge portion to distract the vertebral bodies apart. The angular relationship of the two vertebral bodies adjacent that disc space will then be determined by the shape of the distractor element. It is appreciated that while not preferred, a distractor could be inserted into the disc space first, then the milling block assembly is brought into place relative to the spine thereafter.

The milling block is then secured to the anterior aspect of the spine preferably, by engaging each of the adjacent vertebral bodies. The width and depth of bone resection may then be easily confirmed visually prior to any actual bone resection. The distractor element and distractor apparatus are then removed from the disc space.

The surgeon may then remove disc material that is at least sufficient to create a portion of an implant receiving space.

Although a milling block is preferred for its use in restoring lordosis to adjacent vertebral bodies, it will be appreciated by those of ordinary skill in the art that other devices may be used to induce lordosis to the adjacent vertebral bodies in instances where it is desired to do so.

The disc space is then prepared by a bone removal instrument to receive a correctly sized implant. The proper dimensioned bone removal means, corresponding to the previously employed distractor element, is selected and using the receiving depth gauge, the bone removal means is adjusted for depth and locked. The bone removal means is secured to the milling port of the milling block, and the space is then milled to remove a portion of bone from the endplates adjacent to the disc space. The milling apparatus is removed and the prepared space may be irrigated and suctioned through the milling block, or alternatively the entire milling assembly including the milling block may first be removed and the prepared space then irrigated and suctioned.

The prepared space is distracted utilizing conventional means and the appropriate implant or implants are then inserted into the prepared space.

Preferably prior to insertion, the implant may be loaded with fusion promoting materials such as those described in relation to the method from the posterior approach to the spine. The fusion promoting materials may be loaded or preferably compressively loaded into the implant by use of an instrument such as, for example, a tamp, press, or piston at any time during the procedure as desired by the surgeon.

Thereafter, the method may be continued by inserting the implant into the implantation space and moving the expander to expand the implant. Alternatively, if the implant is inserted laproscopically, the method may include assembling the implant, implant holder, and expander driver together so that the expander driver is in the first locked position relative to the implant holder; inserting the implant into the implantation space; retracting the expander driver to the second locked position; rotating the expander driver to move the expander and expand implant. The procedure may be continued by removing the expander driver from the implant and implant holder; inserting fusion promoting material into the implant holder; using the expander driver as a piston to move bone growth promoting material into the interior of the implant; removing the expander driver from the implant holder; unlocking the implant holder from the implant; and removing the implant holder from the implant.

Figure 39:
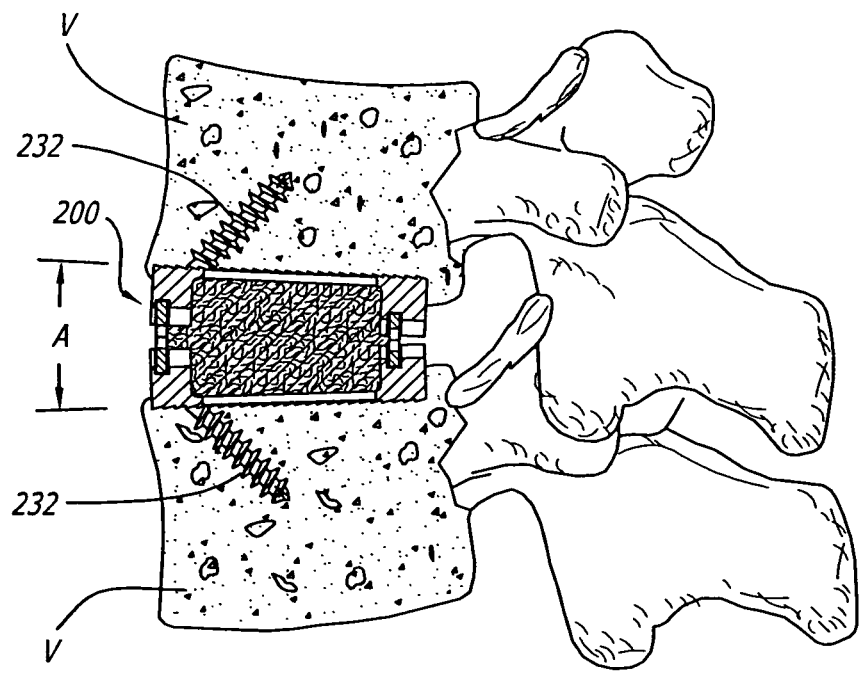
FIG. 39 is a cross-sectional side view of the implantation site formed across the disc space and two adjacent vertebral bodies from the anterior approach to the spine with the implant of FIG. 11 installed into the implantation site in the final deployed position with upper and lower surfaces in angular orientation to one another and bone screws installed to anchor the implant.
Figure 40:
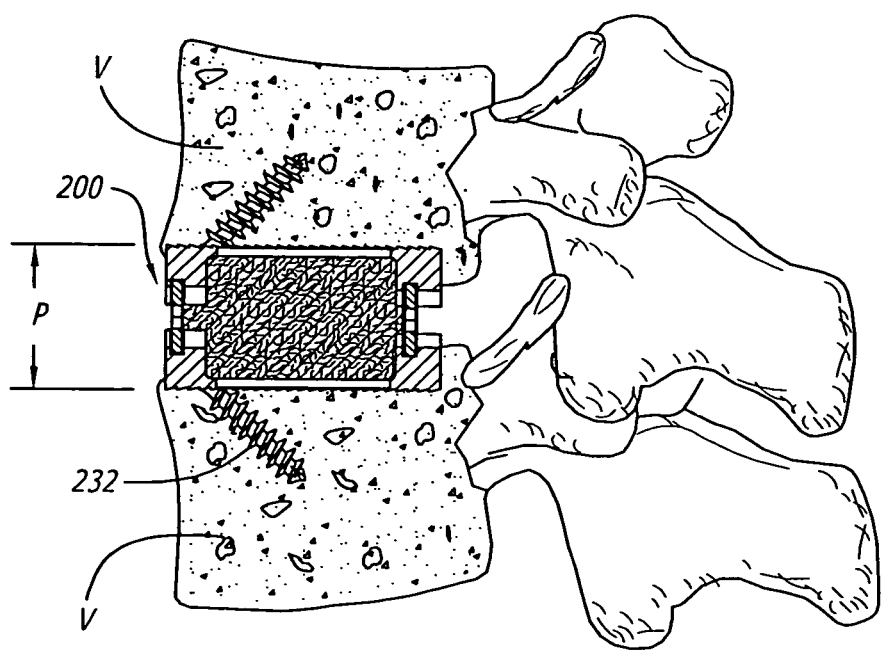
FIG. 40 is a cross-sectional side view of the implantation site formed across the disc space and two adjacent vertebral bodies with the implant of FIG. 11 installed into the implantation space in the final deployed position with upper and lower surfaces in parallel orientation to one another and bone screws installed to anchor the implant.

As shown in FIGS. 39 and 40, if implant 200 is used having expanders at its leading and trailing ends, either one or both expanders 220 may be used to expand implant 200 to create a desired angulation of the adjacent vertebral bodies. Additionally, bone screws 232 may be inserted into the adjacent vertebral bodies to better anchor implant 200 to the spine.

Thereafter, an end cap may be attached and scar tissue-inhibiting materials applied to the implant as desired though these are less of a consideration than in the spinal canal. The steps for the method from the anterior approach to the spine may be varied as already mentioned with regards to the method from the posterior approach to the spine.

FIGS. 41-68 show various views of embodiments of expandable arcuate interbody spinal fusion implants adapted for use with the instrumentation and methods of the present invention.

As used herein, the term "arcuate" is intended to describe the shape of an implant adapted to be inserted into a disc space between two adjacent vertebral bodies that each have a portion after preparation of the disc space that are arcs of the same circle. For example, for implants having a circular cross section such as threaded implants, the curvature of the upper and lower surfaces contacting the adjacent vertebral bodies is a radius of half the width of the implant.

As shown in FIGS. 41-48, implant 800 is similar to implant 100 except that upper and lower members 806, 808 are each preferably arcuate and adapted for placement toward and at least in part within the upper and lower of two adjacent vertebral bodies, respectively. Additionally, exterior surface 812 of each of opposed upper and lower members 806, 808 has at least one bone-engaging projection 814 in the form of a thread. Pin receiving holes 826 on trailing end 804 of implant 800 are adapted to receive an implant holder (described below).

Figure 41:
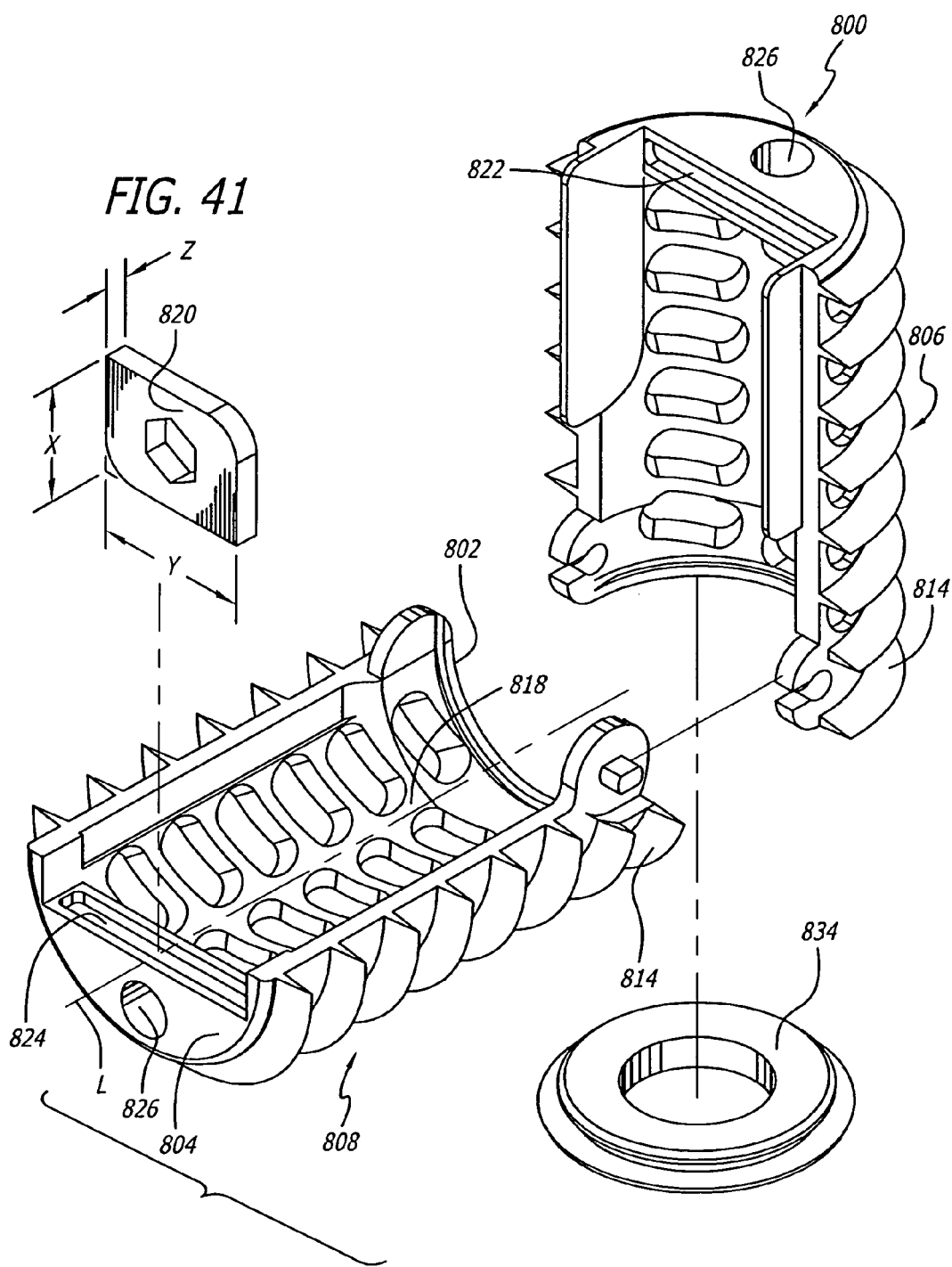
FIG. 41 is an exploded perspective view of an embodiment of an anterior lumbar expandable arcuate interbody spinal fusion implant for use with the instrumentation and method of the present invention.
Figure 47:
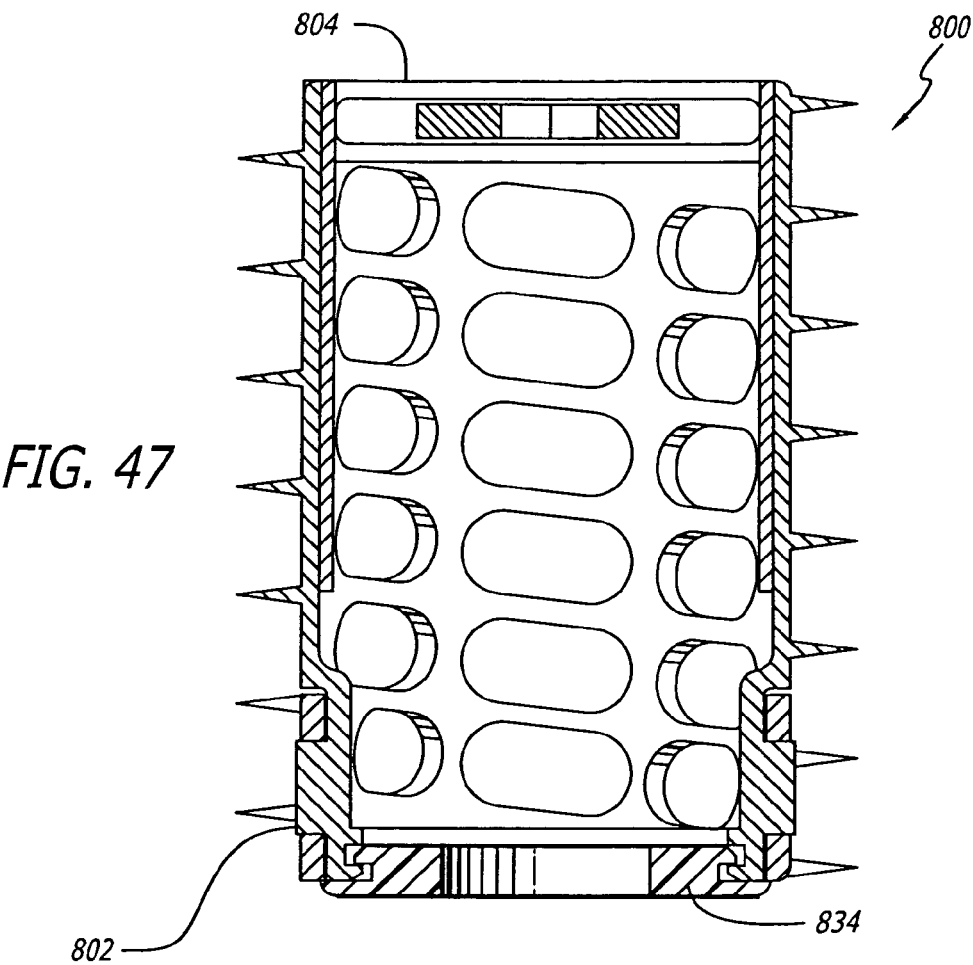
FIG. 47 is a cross-sectional view along line 47-47 of FIG. 45.
Figure 48:
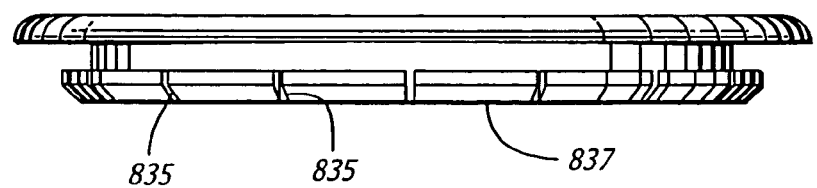
FIG. 48 is a side elevation view of an end cap for use with the implant of FIG. 41.

As shown in FIGS. 41 and 48, a cap 834 may be used to close leading end 802 of implant 800. As may be appreciated by those skilled in the art, cap 834 may be adapted for attachment to implant 800 in a number of ways. For example, the interior surface of cap 834 may have spaced slots 835 between flanges 837 about its circumference to facilitate a snap fit between cap 834 and the implant 800, or the rim of cap 834 may be threaded for rotational engagement with leading end 802 of implant 800. Further, cap 834 may be solid or perforate and made of a surgical quality plastic that may be resorbable or of any other suitable material.

FIGS. 49-54 show various steps of a preferred method for inserting implant 800 and using associated instrumentation disclosed herein from an anterior approach to the spine.

The surgeon first identifies the correct disc space to be operated upon by direct inspection or by radiographic means such as a radiopaque marker and an x-ray or image intensifier. The disc is then surgically accessed from a position anterior to the transverse processes of the vertebrae to be fused. The surgeon may then remove disc material that is at least sufficient to create a portion of an implant receiving space. Alternatively, the surgeon may first insert a guard such as the dynamic guard described above, and then with the use of the guard remove at least sufficient disc material to create the portion of an implant receiving space.

The disc space is then prepared by a bone removal instrument to receive a correctly sized implant 800. Where it is desirable to leave the guard for protecting adjacent delicate neurological structures in place after the preparation of the disc space, the described operation can be performed through the guard and be removed at its completion. The depth of insertion may be monitored by x-ray.

After the disc space has been prepared, fusion promoting materials may be loaded or preferably compressively loaded into implant 800 by use of an instrument such as, for example, a tamp, press, or piston at any time during the procedure as desired by the surgeon.

Figure 49:
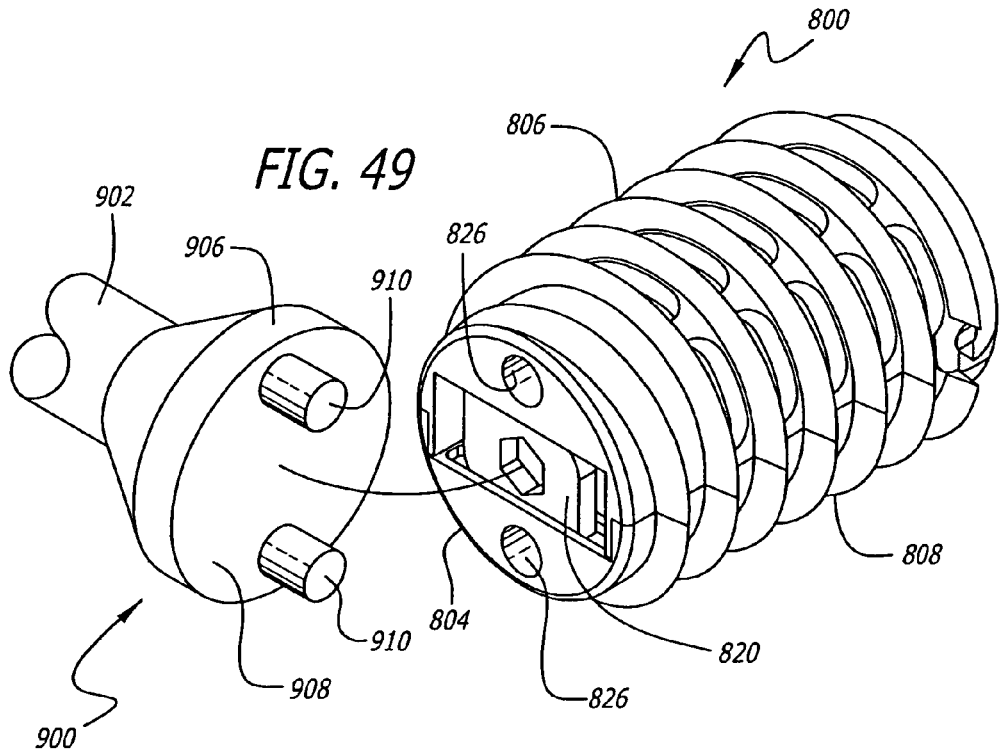
FIG. 49 is a perspective view of the implant of FIG. 41 and an implant inserter with a head configured to cooperatively engage the trailing end of the implant, the head having two projections for engagement with complementary receiving holes on the trailing end of the implant.

As shown in FIG. 49, a preferred embodiment of the working end of an implant holder 900 for holding implant 800 and for use in inserting implant 800 into the disc space has a shaft 902 and a distal end 904 with an enlarged head 906. Head 906 has an implant engagement area 908 with projections 910. Projections 910 may be formed as pins, pegs, or any other projection suitable for the intended purpose. Distal end 904 is configured to be inserted into trailing end 804 of implant 800 such that pins 910 are positioned for engagement with pin receiving holes 826 of implant 800. Pins 910 hold upper and lower members 806, 808 of implant 800 together during insertion thereof. A person of ordinary skill in the art will appreciate that other means of attaching implant holder 900 to implant 800 may be used and are within the broad scope of the present invention. Such means may include, for example only, flanges, screw threads, and magnetism.

Figure 50:
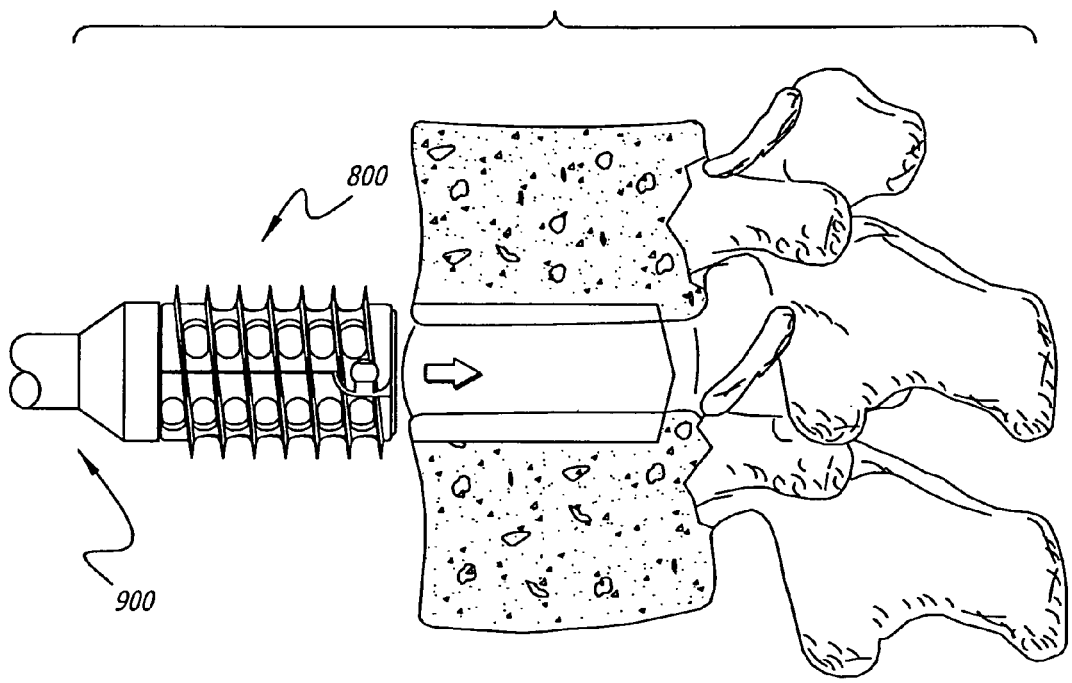
FIG. 50 is a side view of the implant of FIG. 41 being inserted by the implant inserter of FIG. 49 from a generally anterior approach to the spine into an implantation site formed across the height of a disc space and between two adjacent vertebral bodies of the spine shown in partial cross-section.
Figure 51:
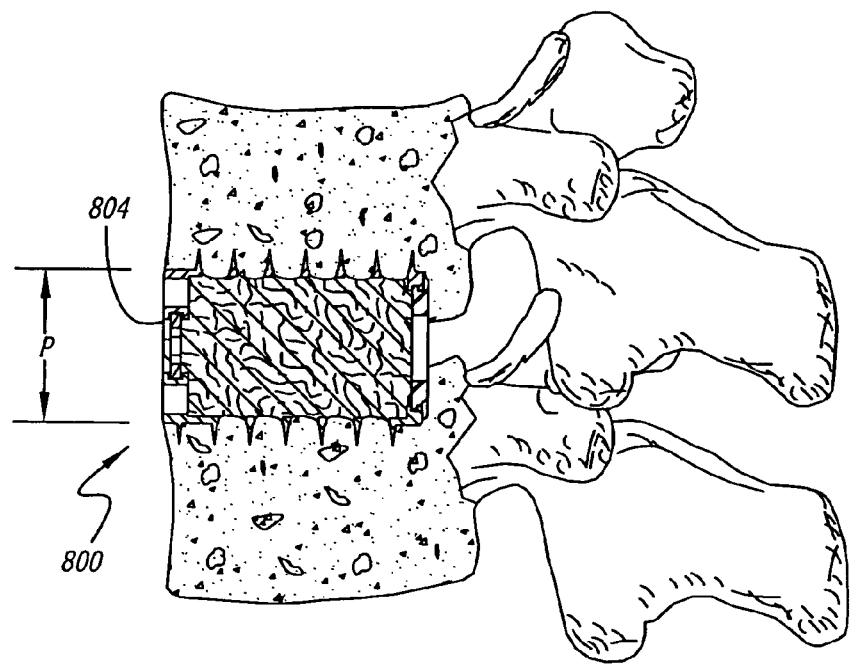
FIG. 51 is a cross-sectional view of the implant of FIG. 41 inserted in the implantation site of FIG. 50.

As shown in FIGS. 50 and 51, pins 910 are engaged with pin receiving holes 826 and implant 800 is inserted into the disc space in its unexpanded state. Pins 910 attach to implant 800 to preferably permit implant 800 to be rotated into the disc space. After implant 800 has been inserted into the disc space, implant holder 900 is removed from implant 800.

Figure 52:
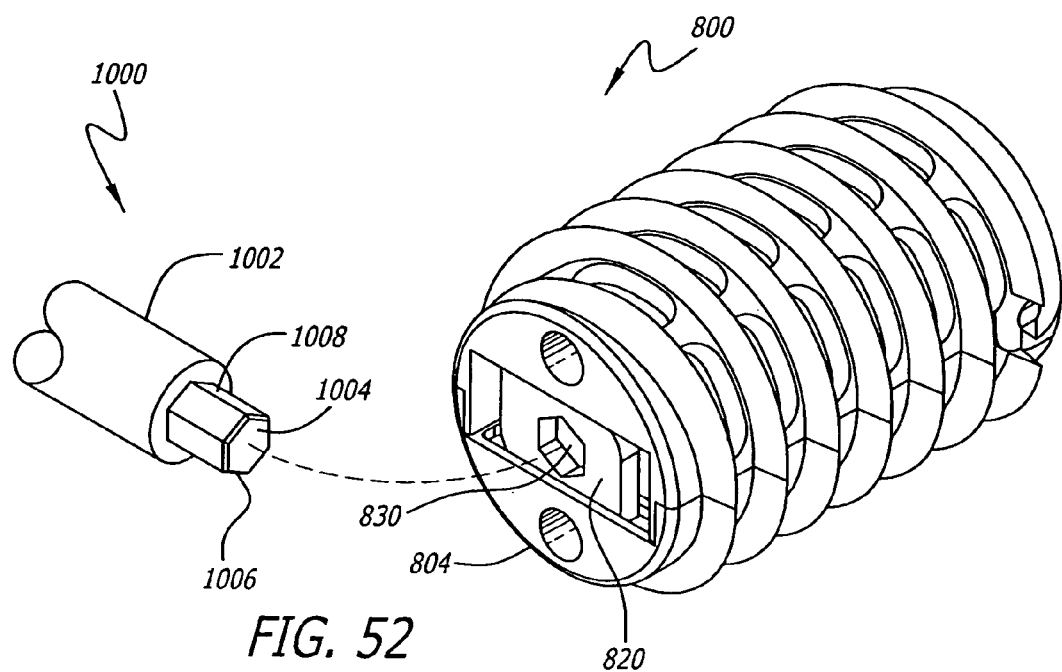
FIG. 52 is a trailing end perspective view of the implant of FIG. 41 with an expander driver instrument being positioned to engage the expander, the expander driver instrument having an end configured to cooperatively engage the expander.

As shown in FIG. 52, the procedure may be continued by aligning expander driver 1000 with trailing end 804 of implant 800. A preferred expander driver 1000 for engaging and rotating expander 820 has a shaft 1002 with a distal end 1004 having a tip 1006. Tip 1006 has an expander engagement area 1008 adapted to cooperatively engage opening 830 of expander 820. In a preferred embodiment, tip 1006 is hex-shaped, but may be of any shape suitable to engage expander 820.

Figure 53:
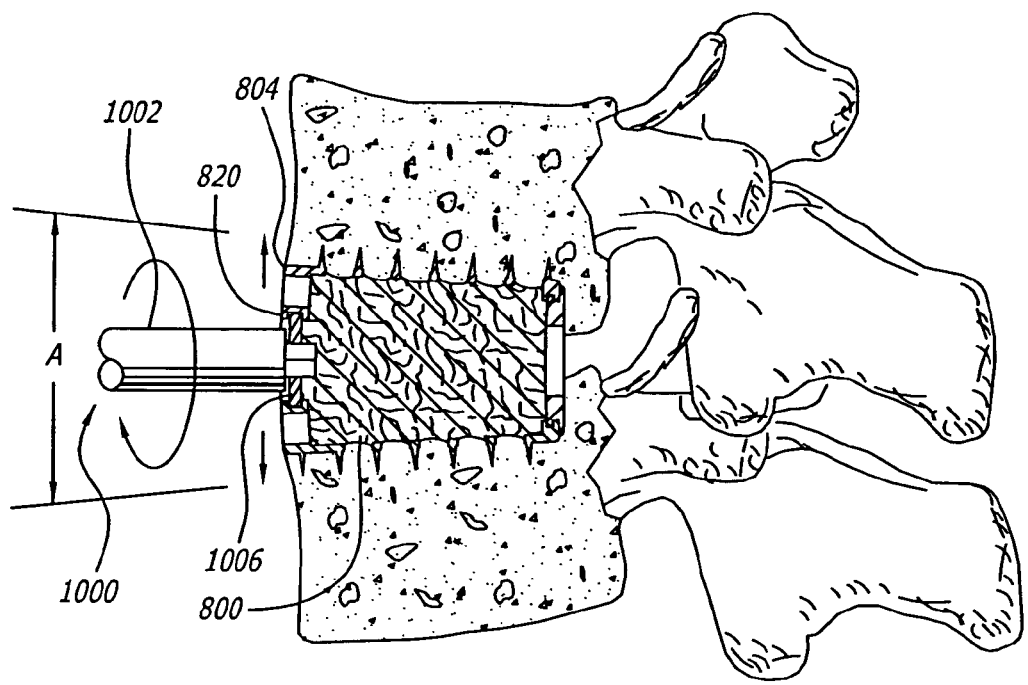
FIG. 53 is a cross-sectional view of the implant of FIG. 41 inserted from an anterior approach to the spine in an implantation site of FIG. 50 and expanded by the expander driver instrument of FIG. 52 to place the adjacent vertebral bodies in lordosis.

As shown in FIG. 53, tip 1006 of expander driver 1000 is introduced into and advanced through trailing end 804 of implant 800. The depth of penetration of expander driver 1000 into and through trailing end 804 is stopped out by the larger cross sectional dimension of shaft 1002.

Figure 54:
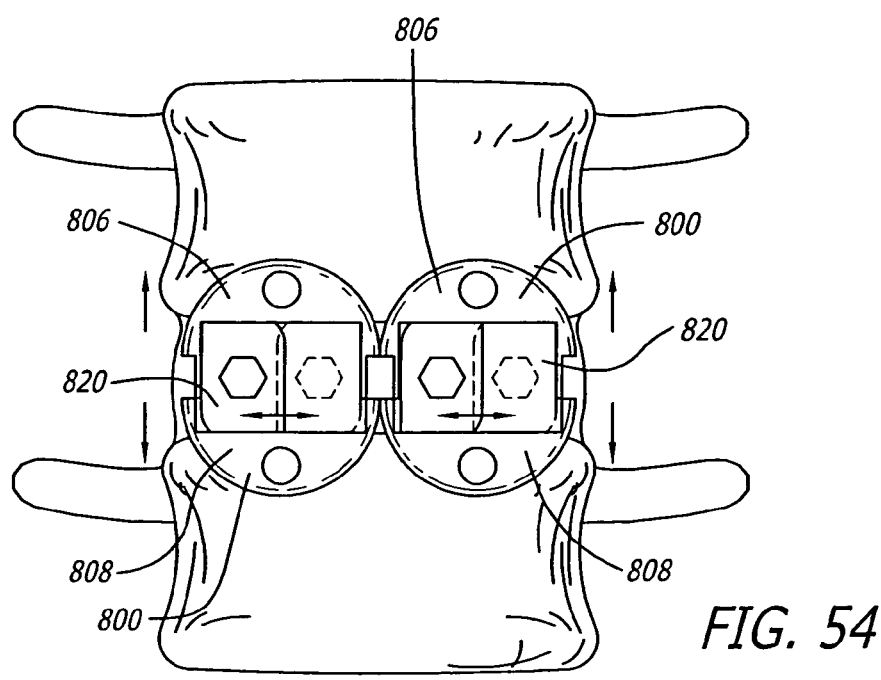
FIG. 54 is a trailing end view of the anterior aspect of two adjacent vertebral bodies and two implants of FIG. 41 implanted therebetween in a final position.

As shown in FIG. 54, expander driver 1000 is rotated to move expander 820 from its initial position to its final position to expand implant 800. During rotation of expander 820, upper and lower members 806, 808 move from parallel orientation P, as shown in FIG. 51 where implant 800 is in a first position, to an angled orientation A, as shown in FIG. 53 where implant 800 is in a second position. Implant 800 may be further packed with bone growth promoting materials to fill any spaces left behind by the withdrawal of expander driver 1000 from implant 800. As shown in FIGS. 41 and 54, tracks 822, 824 are configured to permit expander 820 to rotate therein and then to move from side to side within track 822, 824 as shown by arrows B to permit greater access to hollow interior 818.

As best seen in FIG. 54, for example, more than one implant 800 may be placed in a side-by-side configuration to beneficially occupy more disc space than would otherwise be possible with a single arcuate interbody spinal fusion implant.

Thereafter, at the surgeon's discretion, a cap may be installed to close off at least part of the implant's trailing end to prevent bone from growing into the spinal canal, or to limit adhesions of the neurological structures at the canal floor, or to otherwise protect the neurological structures. One of the purposes for a cap includes restricting the passage of fusion-promoting materials so that they remain loaded within the implant. Another purpose for a cap may be to add structural support to the implant.

FIGS. 55-60 show another embodiment of an expandable arcuate interbody spinal fusion implant adapted for use from the posterior approach with the instrumentation and methods of the present invention generally referred to by the number 1100. Implant 1100 is similar to implant 800 except that it is designed for insertion into the implantation site from a posterior approach to the spine. Implant 1100 preferably has an expander 1120 at leading end 1102 and a pivot 1116 at trailing end 1104. Thus, implant 1100 will get taller at leading end 1102 instead of trailing end 1104. Implant 1100 preferably includes a plurality of openings 1128 in trailing end 1104 to further enhance the growth of bone through implant 1100. Openings 1128 preferably have a smaller diameter than that of pin receiving holes 1126 so that pins 1210 of implant holder 1200 (described below) will not pass therethrough. A person skilled in the art will appreciate that openings 1128 may be shaped in a variety of ways without departing from the broad scope of the present invention.

Figure 55:
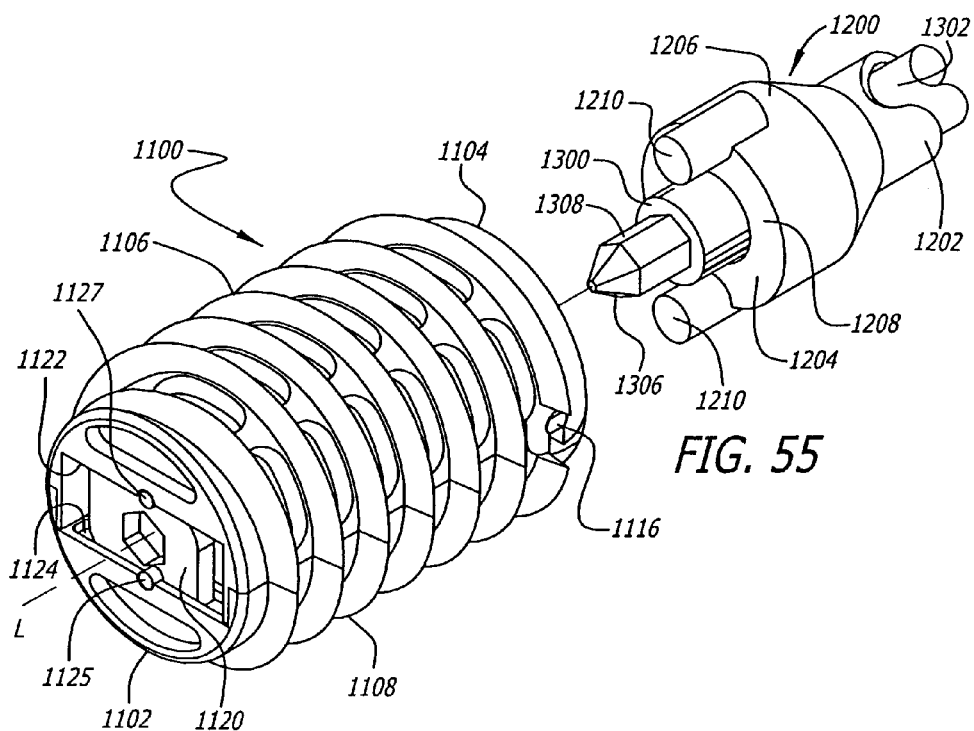
FIG. 55 is a leading end perspective view of an implant, an implant holder with a head configured to cooperatively engage the trailing end of the implant, the head having two projections for engagement with complementary receiving holes on the trailing end of the implant, the implant holder being hollow and adapted to accommodate the passage of an expander driver therethrough, the expander driver being shown in a retracted position within the implant holder.

As best shown in FIG. 55, tracks 1122, 1124 of upper and lower members 1106, 1108 of implant 1100 have a cooperating surface 1125, and expander 1120 has a corresponding cooperating surface 1127 that contacts cooperating surface 1125 of tracks 1122, 1124 to orient expander 1120 in a predetermined location. The cooperating surfaces orient expander 1120 within implant 1100 such that the axis of rotation of expander 1120 is parallel to the longitudinal axis of implant 1100 and more particularly center expander 1120 within implant 1100 such that the axis of rotation of expander 1120 coincides with longitudinal axis L of implant 1100.

As shown in FIGS. 55-57, implant holder 1200 includes a shaft 1202 having a distal end 1204 with an enlarged head 1206. Head 1206 includes an implant engagement area 1208 with pins 1210. Pins 1210 serve in a similar capacity as that described in relation to pins 910 above. Implant holder 1200 has a bore 1212 adapted to cooperatively receive an expander driver 1300 therethrough.

Expander driver 1300 has a shaft 1302 having a distal end 1304 with a tip 1306 having an expander engagement area 1308. The leading end of tip 1306 is shaped to facilitate the instrument being advanced by a rotational movement through the implant packing material in implant 1100 until it reaches and is advanced into engagement with expander 1120. Expander driver 1300 is adapted to extend into implant 1100 to move expander 1120 from an initial position to a final position to expand implant 1100, as will be described in more detail in the method below.

Figure 60:
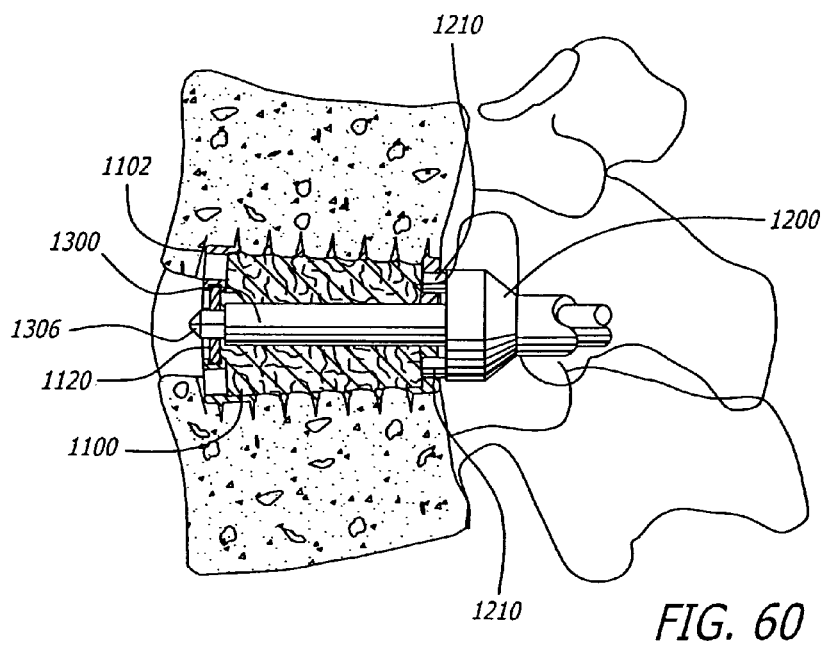
FIG. 60 is a cross-sectional view of the implant of FIG. 55 inserted from a posterior approach to the spine in the implantation site of FIG. 58 and expanded by the expander driver instrument of FIG. 55 shown in a fully extended state to place the adjacent vertebral bodies in lordosis.
Figure 58:
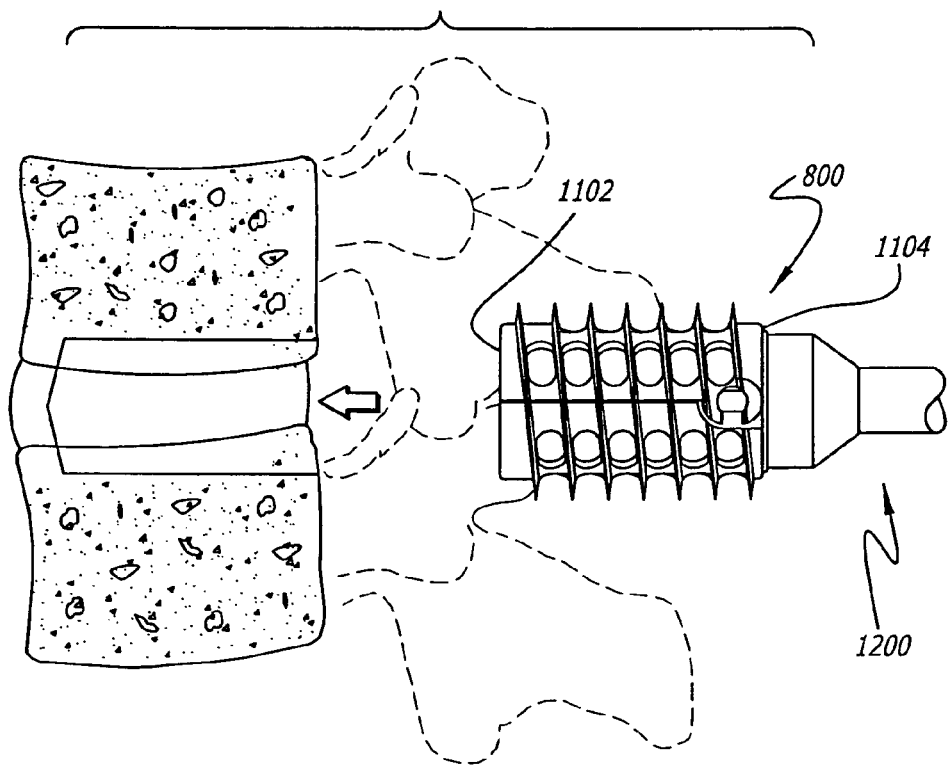
FIG. 58 is a side view of the implant of FIG. 55 being inserted by the implant inserter of FIG. 55 from a generally posterior approach to the spine into an implantation site formed across the height of a disc space and between two adjacent vertebral bodies of the spine shown in partial cross-section.
Figure 59:
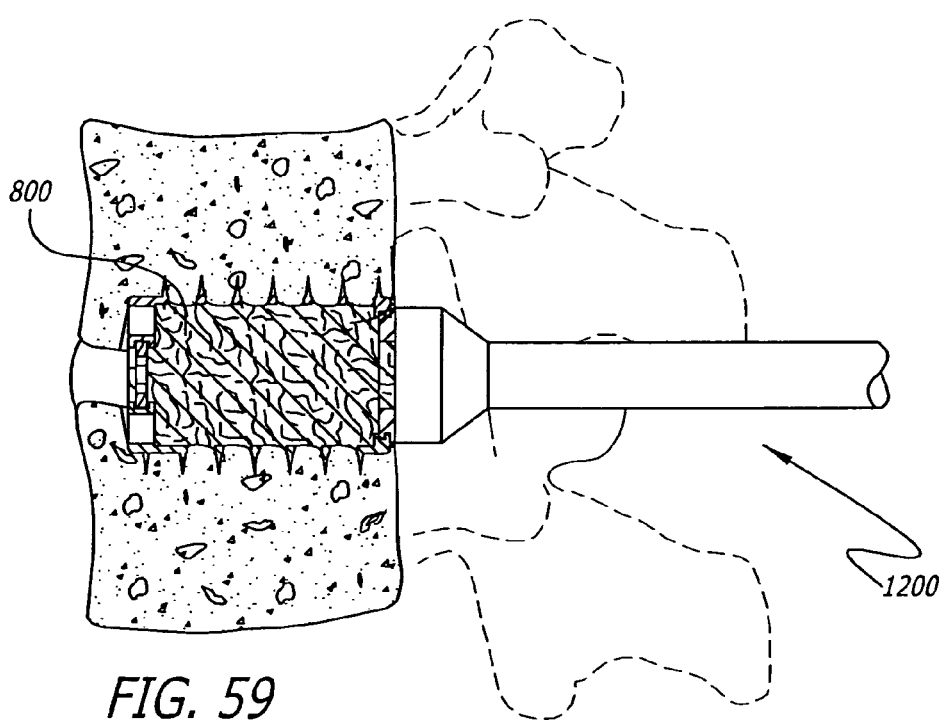
FIG. 59 is a cross-sectional view of the implant of FIG. 55 inserted in the implantation site of FIG. 58.

As shown in FIGS. 58-60, the method for inserting implant 1100 from a posterior approach to the spine is similar to that described in relation to FIGS. 19-38, except that pins 1210 of implant holder 1200 are engaged with pin receiving holes 1126 and implant 1100 is advanced into the prepared recipient disc space by a rotational force, pushing movement, an impaction force, or a combination thereof through a guard in its unexpanded state.

As shown in FIG. 60, after implant 1100 is properly seated in the disc space the procedure may be continued by preferably keeping implant holder 1200 attached to trailing end 1104 and extending expander driver 1300 through implant 1100 until tip 1306 cooperatively engages with expander 1120. Expander driver 1300 is rotated to move expander 1120 so that at least leading end 1102 of implant 1100 is expanded so as to increase the maximum implant height which is proximate leading end 1102.

It will be appreciated by those skilled in the art that many of the steps described in relation to the further packing of impacted implants with bone growth promoting materials are applicable to the further packing of arcuate implants with bone growth promoting materials and will not be repeated here.

Having completed the procedure on a first side, the procedure is then repeated as already described on the opposite side of the same disc space leading to the implantation of two implants 1100 in the same disc space.

A person skilled in the art will appreciate that although preferred, implant holder 1200 is not essential in order to expand the implant. For example, as shown in FIG. 61, an implant 1400 may be inserted into the implantation space by a variety of known implant insertion devices and then expanded with expander driver 1300.

FIGS. 62-66 show another preferred embodiment of an expandable arcuate interbody spinal fusion implant for use from the anterior approach with the instrumentation and methods of the present invention generally referred to by the number 1500.

Figure 62:
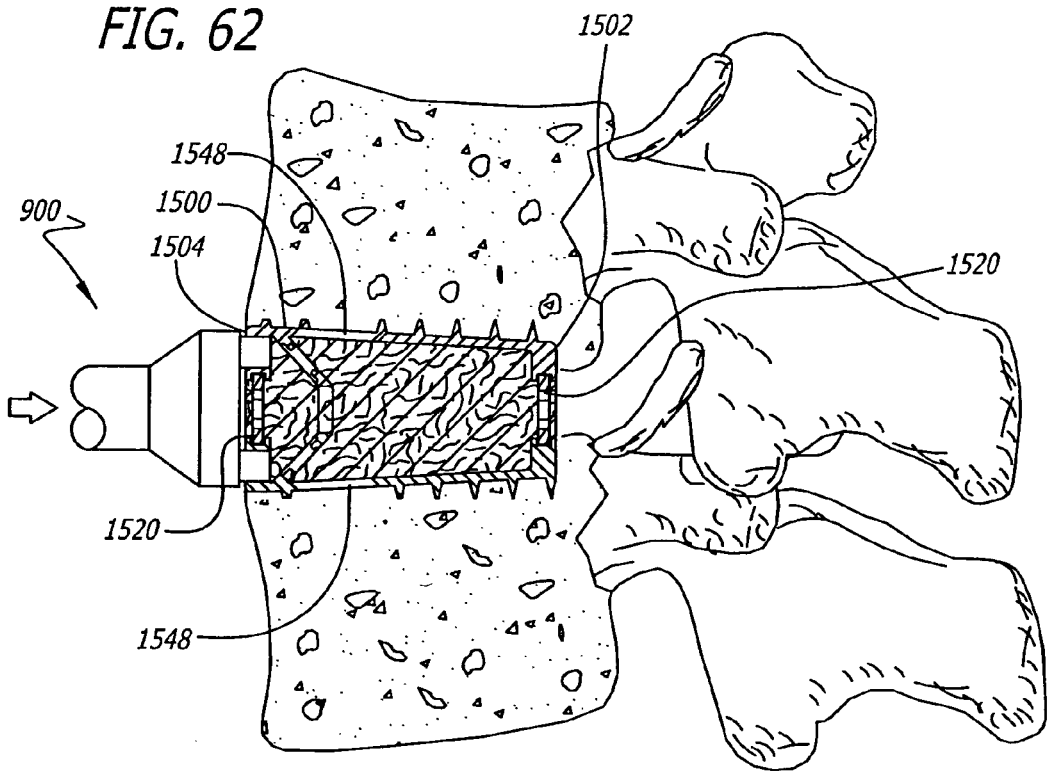
FIG. 62 is a side view of another embodiment of an implant being inserted by the implant holder of FIG. 49 from a generally anterior approach to the spine into an implantation site formed across the height of a disc space and two adjacent vertebral bodies of the spine shown in partial cross-section.

As shown in FIG. 62 implant 1500 is tapered from leading end 1502 towards trailing 1502 in an unexpanded position and preferably has a second expander 1520 at its leading end 1502 for moving at least a portion of the upper and lower members away from one another to increase the height of implant 1500. The advantages of using a second expander are described in relation to implant 200 of FIG. 11.

Figure 66:
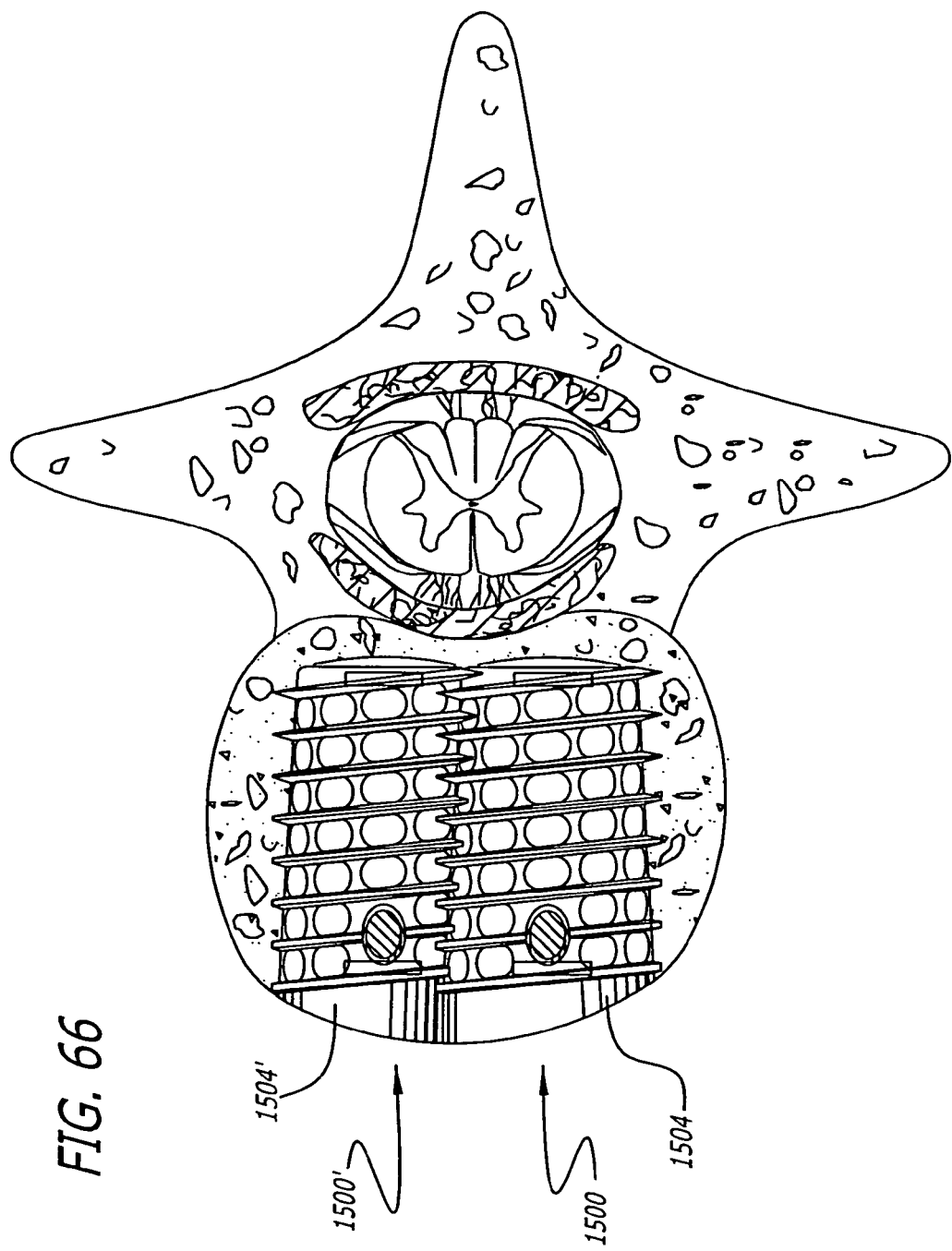
FIG. 66 is a top plan view of the implants of FIG. 65 inserted at least in part within the lower vertebral body of an implantation site formed anteriorly across a disc space with the vertebral body shown in partial cross-section, the implants having an expander at each of the leading and trailing ends of each implant.

As shown in FIGS. 64-66, another aspect of implant 1500 is that its upper and lower members 1506, 1508 have screw holes 1548 passing therethrough adapted to receive bone screws 1550 passing from the interior of implant 1500 into adjacent vertebral bodies to anchor implant 1500 to an adjacent vertebral body. A purpose of the opposed bone screws is to rigidly secure the implant within the vertebral segment. A further purpose is to pull each of the adjacent vertebral bodies toward the implant and towards each other. If the articulation device holds the upper and lower members together, as in the embodiment of posterior implant 100 of FIGS. 1-7, by closely encircling a post then the implant cannot expand at that location. Bone screws are not essential to the operation of the invention, but are preferable for providing added securement of the implant to the adjacent vertebral bodies.

As shown in FIG. 65, the side surface of implant 1500' facing implant 1500 is contoured in a C-shape to permit the central longitudinal axis of implants 1500, 1500' to be closer together. Examples of such implants are taught by Michelson in U.S. Pat. No. 5,593,409 entitled "Interbody Spinal Fusion Implants," and co-pending U.S. patent application Ser. No. 09/566,272 entitled "Nested Interbody Spinal Fusion Implants," the disclosures of which are hereby incorporated by reference herein.

As shown in FIG. 66, the trailing ends 1504, 1504' of implants 1500, 1500', respectively, are shaped to generally conform to the anatomical configuration of the anterior aspect of the vertebral body to prevent the anterior lateral aspect of the implant from protruding from the spine.

Figure 63:
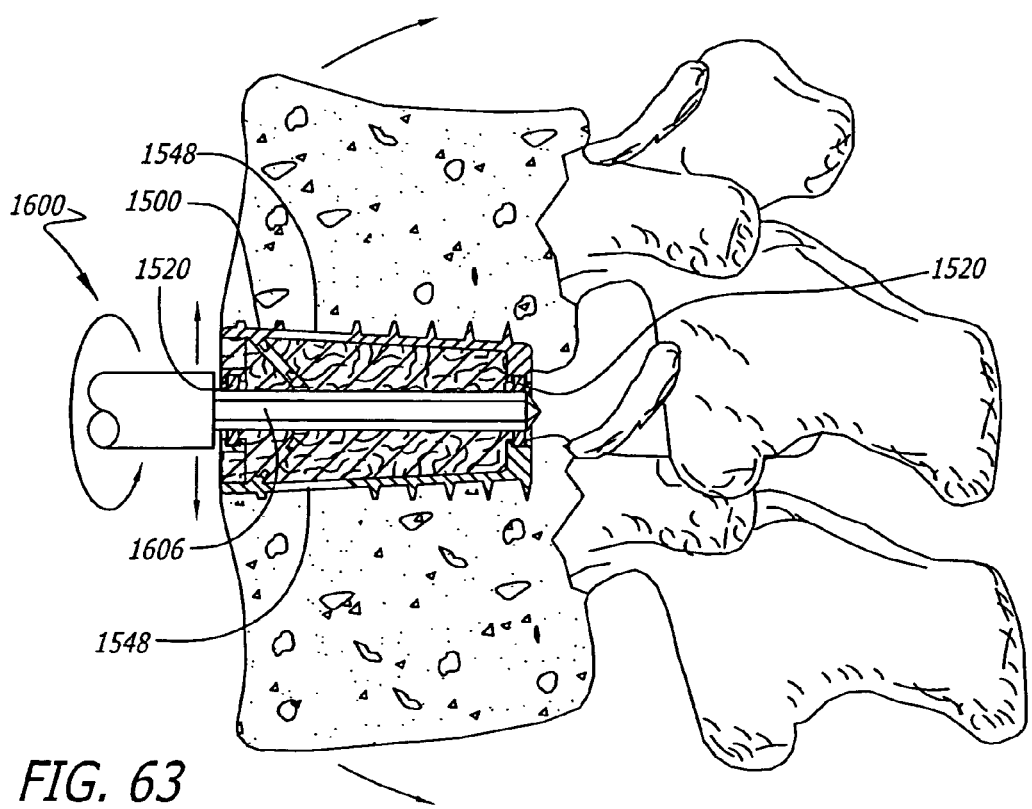
FIG. 63 is a cross-sectional view of the implant of FIG. 62 expanded from an anterior approach to the spine by an expander driver instrument having an extended shaft configured to engage more than one expander to place the adjacent vertebral bodies in lordosis.

As shown in FIGS. 62-64, a preferred method for installing and expanding an implant with multiple expanders is similar to that described in relation to an implant with one expander such as shown in FIGS. 49-54, except that an expander driver 1600 is utilized. Expander driver 1600 is similar to expander driver 1000 except that expander driver 1600 has an elongated tip 1606 adapted to extend through the openings of multiple expanders through implant 1500, as shown in FIG. 63. Tip 1606 permits multiple expanders 1520 to be moved simultaneously to expand implant 1500. After installation of implants 1500, bone screws 1550 may be inserted through bone screw holes 1548 using known methods.

Figure 67:
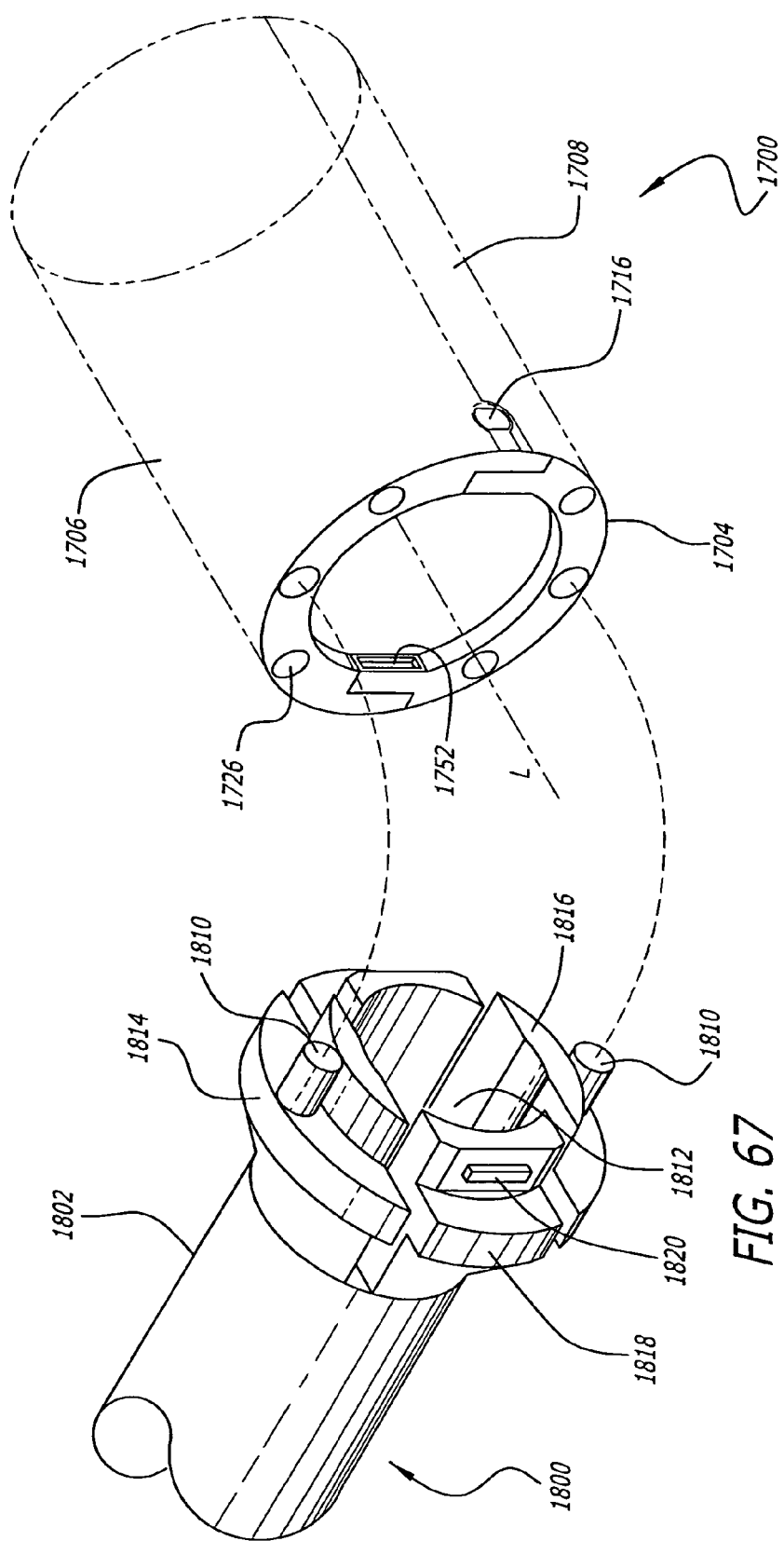
FIG. 67 is a perspective view of another embodiment of an implant inserter of the present invention having upper and lower projections and a pair of side extensions with flanges thereon to cooperatively engage complementary receiving holes and slots, respectively of a trailing end of a generally cylindrical implant adapted for insertion from the posterior aspect.

FIG. 67 shows a schematic drawing representing another embodiment of an expandable arcuate interbody spinal fusion implant generally referred to by the number 1700 having a trailing end adapted for use with another embodiment of the instrumentation and methods of the present invention. Implant 1700 is similar to implant 1100 described above, except that in addition to pin receiving holes 1726, trailing end 1704 also preferably includes opposed slots 1752 along the interior surface of trailing end 1704. Slots 1752 are adapted to lockably receive flanges 1820 of an implant holder 1800.

Implant holder 1800 includes a shaft 1802 having a distal end 1804. Distal end 1804 includes an implant engagement area 1808 having pins 1810 and a bore 1812. Preferably surrounding the perimeter of bore 1812 are upper and lower extensions 1814, 1816, respectively, and a pair of side extensions 1818. Side extensions 1818 each have a flange 1820 adapted to cooperatively engage slots 1752 of implant 1700 when in a locked configuration.

In use, side extensions 1818 are pushed in to force side extensions 1818 to move together and move flanges 1820 into slots 1752 of implant 1700, then released thereby locking implant holder 1800 to implant 1700. Thereafter, an expander driver such as taught in relation to FIG. 55 may be inserted through bore 1812 and into implant 1700 to move an expander (not shown) to expand implant 1700.

While implant 1700 is being expanded, the height of trailing end 1702 decreases as upper and lower members 1706, 1708, respectively, articulate about pivot point 1716. Upper and lower extensions 1814, 1816, respectively, are adapted to move inwardly toward the longitudinal axis of implant holder 1800 so that implant holder 1800 may remain engaged to implant 1700 while the implant is being expanded. It will be appreciated that other configurations of the implant holder are possible for permitting the implant holder to remain engaged to the implant during a change in the dimension of the implant and are within the broad scope of the present invention.

Figure 68:
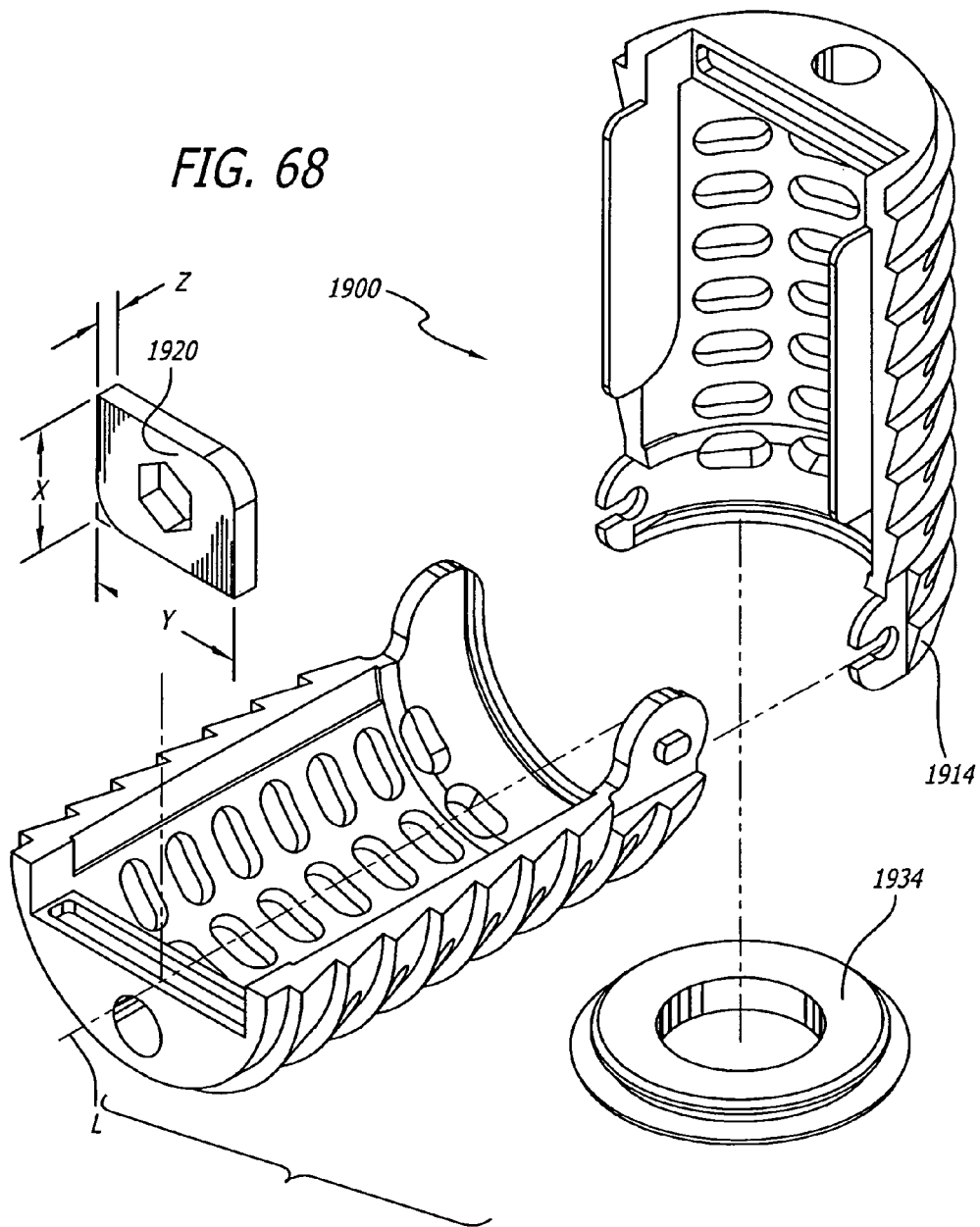
FIG. 68 is an exploded perspective view of another embodiment of a spinal fusion implant for use with the instrumentation and method of the present invention.

FIG. 68 shows another preferred embodiment of an expandable arcuate interbody spinal fusion implant for use from the anterior approach to the spine with the instrumentation and methods of the present invention generally referred to by the number 1900. Implant 1900 is similar to implant 800 except that bone engaging projections 1914 are in the form of forward-facing ratchets, thus facilitating linear insertion while resisting expulsion from the implantation space. Implant 1900 may be inserted using methods such as those described in relation to implant 100 and instruments such as those described in relation to implant 800.

While the instruments and methods of the present invention have been described relative to spinal fusion implants, it will be appreciated that the instruments and methods of the present invention may also be used with other implants such as inert spacers, artificial discs, bone grafts, and other inserts suitable for the intended purpose of substantially reducing or eliminating motion between two adjacent bone masses.

There is disclosed in the above description and the drawings implants and instruments and methods for use therewith, which fully and effectively accomplish the objectives of this invention. However, it will be apparent that variations and modifications of the disclosed embodiments may be made without departing from the principles of the invention.

What is claimed is:

1. A combination of an interbody spinal implant and an implant holder for use in human interbody spinal surgery comprising:
   said interbody spinal implant having a trailing end adapted to be engaged to said implant holder; and
   said implant holder having a body having a distal end, a proximal end, and a length therebetween, and at least two extensions extending from said distal end of said body, said extensions having an interior surface and an exterior surface opposite said interior surface, said extensions being adapted to be moved toward one another by an inward force applied by a user to said exterior surface to permit said extensions of said implant holder to pass into said trailing end of said implant and for said exterior surface to cooperatively engage said trailing end of said implant after the inward force is removed.

2. The combination of claim 1, wherein said body of said implant holder has a passage along at least a portion of the length of said body, said passage being configured to permit the passage of an instrument or fusion promoting substances therethrough.

3. The combination of claim 2, wherein said extensions include a projection adapted to cooperatively engage at least a portion of said trailing end of said implant.

4. The combination of claim 3, wherein said projection is adapted to cooperatively engage a recess in said trailing end of said implant.

5. The combination of claim 4, wherein said projection includes a flange and said recess is a slot.

6. The combination of claim 4, wherein said projection includes a pin and said recess is a pin receiving opening.

7. The combination of claim 3, wherein said implant is an expandable spinal implant, said projection being adapted to remain engaged to said expandable spinal implant while said implant is expanded from an unexpanded position to an expanded position.

8. The combination of claim 7, wherein said projection is a pin adapted to move within a recess in said trailing end while said expandable spinal implant is expanded from the unexpanded position to the expanded position.

9. The combination of claim 2, wherein said proximal end of said body is adapted to receive a handle.

10. The combination of claim 9, wherein said handle is detachable.

11. The combination of claim 2, wherein said implant is an expandable spinal implant, the combination further in combination with an expander driver adapted to expand said expandable implant.

12. The combination of claim 11, wherein said implant has an expander, said implant being adapted to increase in height with rotation of said expander, said expander driver having a distal end adapted to engage said expander of said expandable implant to permit rotation of said expander of said expandable implant.

13. The combination of claim 12, wherein said expander driver includes a handle to allow said expander driver to be rotated upon engagement with said expander of said expandable implant.

14. The combination of claim 12, wherein said distal end of said expander driver has a tip adapted to cooperatively engage an opening in said expander of said expandable implant.

15. The combination of claim 12, wherein said expandable implant has at least a second expander, said expander driver being adapted to engage at least two of said expanders.

16. The combination of claim 15, wherein said expander driver has an elongated tip adapted to cooperatively engage an opening in at least two of said expanders.

17. The combination of claim 11, wherein said expander driver has an implant holder engagement portion configured for lockable engagement with an expander driver engagement portion of said body of said implant holder.

18. The combination of claim 17, wherein said expander driver is movable within said passage of said body between a first locked position not permitting rotation relative to said implant holder and a second locked position permitting said expander driver to rotate relative to said implant holder.

19. The combination of claim 18, wherein said expander driver engagement portion limits the rotation of said expander driver to one direction in the second locked position.

20. The combination of claim 19, wherein said expander driver engagement portion limits the amount of rotation of said expander driver in the second locked position.

21. The combination of claim 17, wherein said implant holder engagement portion of said expander driver has at least one detent adapted for lockable engagement with a spring-biased ball in said expander driver engagement portion of said body of said implant holder.

22. The combination of claim 11, wherein said expander driver has an enlarged portion sized and shaped to fit into and rotate within said passage of said body.

23. The combination of claim 22, wherein said enlarged portion of said expander driver has a shoulder and a peg adapted to cooperate with said body of said implant holder, said body of said implant holder having a cutout and a slot adapted to cooperate with said shoulder and peg of said enlarged portion of said expander driver to limit the rotation of said expander driver while engaged with said body of said implant holder.

24. The combination of claim 1, wherein said spinal implant is a spinal fusion implant for promoting fusion between adjacent vertebral bodies, said implant having upper and lower surfaces for placement between and in contact with the adjacent vertebral bodies, each of said upper and lower surfaces having at least one opening adapted to permit bone from the adjacent vertebral bodies to grow through said implant.

25. The combination of claim 24, wherein said spinal fusion implant has a hollow between said upper and lower surfaces for holding fusion promoting substances.

26. The combination of claim 24, wherein said spinal fusion implant is an expandable implant having an expander adapted to increase the height of said implant upon movement from an insertion position to a final deployed position.

27. The combination of claim 26, wherein said spinal fusion implant is separable into an upper member and a lower member to permit the placement of said expander between said upper and lower members.

28. The combination of claim 27, wherein said upper and lower members are at least in part arcuate.

29. The combination of claim 28, wherein said spinal fusion implant includes a thread along at least a portion of said upper and lower surfaces of said spinal fusion implant.

30. The combination of claim 27, wherein said upper and lower members are configured for at least in part linear insertion into a prepared implantation space between the adjacent vertebral bodies.

31. The combination of claim 30, wherein said spinal fusion implant includes surface projections configured to resist expulsion of said implant from an implantation space into which said implant is adapted to be inserted.

32. The combination of claim 27, wherein said upper and lower members are angled relative to one another to induce an angulation of the adjacent vertebral bodies relative to one another.

33. The combination of claim 24, wherein said spinal fusion implant is in combination with a fusion promoting substance.

34. The combination of claim 33, wherein said fusion promoting substance is selected from one of bone, bone derived products, demineralized bone matrix, ossifying proteins, bone morphogenetic protein, hydroxyapatite, and genes coding for the production of bone.

35. The combination of claim 24, wherein said implant is treated with a fusion promoting substance.

36. The combination of claim 24, wherein said implant is in combination with a chemical substance adapted to inhibit scar formation.

37. The combination of claim 24, wherein said implant is in combination with an antimicrobial material.

38. The combination of claim 1, wherein said implant comprises at least in part of one of bone and bone growth promoting material.

39. The combination of claim 1, wherein said implant comprises at least one of the following materials: metal, titanium, plastic, and ceramic appropriate for implantation in the human body.

40. The combination of claim 1, wherein said implant is at least in part resorbable.

41. The combination of claim 1, wherein said implant is formed of a porous material.

42. The combination of claim 1, wherein said implant is an inert spacer.

43. The combination of claim 1, wherein said implant is an artificial disc.

44. The combination of claim 1, wherein said implant is a bone graft.

45. The combination of claim 1, wherein said implant has a hollow between said upper and lower surfaces, said hollow having a composite material therein.

46. The combination of claim 45, wherein said composite material is other than bone.

47. The combination of claim 1, wherein said exterior surface of said implant holder is adapted to linearly engage said implant.

48. The combination of claim 1, wherein said exterior surface of said implant holder is adapted to slideably engage said implant.

49. The combination of claim 1, wherein said exterior surface of said implant holder is adapted to lock to said implant.

* * * * *